United States Patent
Rogers et al.

(10) Patent No.: US 11,666,240 B2
(45) Date of Patent: *Jun. 6, 2023

(54) ULTRA-LOW POWER, MINIATURIZED ELECTRONIC SYSTEMS FOR MONITORING PHYSICAL PARAMETERS WITH WIRELESS COMMUNICATION CAPABILITIES AND APPLICATIONS OF SAME

(71) Applicant: NORTHWESTERN UNIVERSITY, Evanston, IL (US)

(72) Inventors: John A. Rogers, Wilmette, IL (US); Shuai Xu, Bala Cynwyd, PA (US); Seung Yun Heo, Evanston, IL (US); Kyeongha Kwon, Evanston, IL (US); Jong Yoon Lee, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/417,180

(22) PCT Filed: Jan. 3, 2020

(86) PCT No.: PCT/US2020/012241
§ 371 (c)(1),
(2) Date: Jun. 22, 2021

(87) PCT Pub. No.: WO2020/142728
PCT Pub. Date: Jul. 9, 2020

(65) Prior Publication Data
US 2022/0047178 A1  Feb. 17, 2022

Related U.S. Application Data

(60) Provisional application No. 62/787,964, filed on Jan. 3, 2019.

(51) Int. Cl.
*A61B 5/05* (2021.01)
*A61B 5/318* (2021.01)
(Continued)

(52) U.S. Cl.
CPC ............... *A61B 5/05* (2013.01); *A61B 5/002* (2013.01); *A61B 5/0006* (2013.01);
(Continued)

(58) Field of Classification Search
CPC ......... A61B 5/05; A61B 5/0006; A61B 5/002; A61B 5/0022; A61B 5/02055;
(Continued)

(56) References Cited

U.S. PATENT DOCUMENTS 9,618,635 B2 * 4/2017 Fechner ............ H01L 27/11517
10,132,680 B1 * 11/2018 Isikman ................... G01J 1/18
(Continued)

FOREIGN PATENT DOCUMENTS

WO   2016196673 A1   12/2016

OTHER PUBLICATIONS

Heo et al., Wireless, battery-free, flexible, miniaturized dosimeters monitor exposure to solar radiation and to light for phototherapy, Sci. Transl. Med., 10, 2018, 1-12.
(Continued)

*Primary Examiner* — Amine Benlagsir
(74) *Attorney, Agent, or Firm* — Locke Lord LLP; Tim Tingkang Xia, Esq.

(57) ABSTRACT

An electronic system for monitoring a physical parameter includes an ADM comprising an accumulation mode sensor for measuring the physical parameter by generating electrical energy associated with the physical parameter in response to a surrounding condition, and an energy storing device coupled to the accumulation mode sensor for accumulatively storing the generated electrical energy; a power
(Continued)

source; and an SoC coupling with the ADM and the power source, configured such that the stored electrical energy is monitored, and when the stored electrical energy is equal to or greater than a pre-defined threshold, a wake-up event is generated to trigger the SoC to operates in a run mode in which the physical parameter is wirelessly transmitted to a receiver and the stored electrical energy in the energy storing device is discharged, and then the SoC returns to a sleep mode in which a minimal power is consumed.

61 Claims, 38 Drawing Sheets

(51) Int. Cl.
  *A61B 5/389*    (2021.01)
  *A61B 5/00*     (2006.01)
  *A61B 5/0205*    (2006.01)
  *A61B 5/145*    (2006.01)
  *A61B 5/1455*    (2006.01)
  *G01J 1/44*     (2006.01)
  *H04Q 9/00*     (2006.01)

(52) U.S. Cl.
  CPC ........ *A61B 5/0022* (2013.01); *A61B 5/02055* (2013.01); *A61B 5/14517* (2013.01); *A61B 5/14552* (2013.01); *A61B 5/318* (2021.01); *A61B 5/389* (2021.01); *A61B 5/681* (2013.01); *A61B 5/6804* (2013.01); *A61B 5/742* (2013.01); *A61B 5/746* (2013.01); *A61B 5/7455* (2013.01); *G01J 1/44* (2013.01); *H04Q 9/00* (2013.01); *A61B 2560/0242* (2013.01); *A61B 2562/0204* (2013.01); *A61B 2562/029* (2013.01); *A61B 2562/0219* (2013.01); *A61B 2562/0247* (2013.01); *A61B 2562/0271* (2013.01); *G01J 2001/446* (2013.01); *H04Q 2209/43* (2013.01); *H04Q 2209/826* (2013.01)

(58) Field of Classification Search
  CPC . A61B 5/14517; A61B 5/14552; A61B 5/318; A61B 5/389; A61B 5/6804; A61B 5/681; A61B 5/742; A61B 5/7455; A61B 5/746; A61B 2560/0242; A61B 2562/0204; A61B 2562/0219; A61B 2562/0247; A61B 2562/0271; A61B 2562/029; G01J 1/44; G01J 2001/446; H04Q 9/00; H04Q 2209/43; H04Q 2209/826; Y02D 30/70; G16H 50/20; G16H 80/00; G16H 40/67; H04B 5/0043
  See application file for complete search history.

(56) References Cited

U.S. PATENT DOCUMENTS

| | | | |
|---|---|---|---|
| 10,835,126 B1* | 11/2020 | Cong | A61B 5/0075 |
| 11,029,198 B2* | 6/2021 | Rogers | G01J 5/10 |
| 2007/0012965 A1* | 1/2007 | Sandvik | H01L 27/14621 257/292 |
| 2009/0147215 A1* | 6/2009 | Howell | G01J 1/44 250/206 |
| 2009/0273444 A1* | 11/2009 | Brown | H04Q 9/00 340/10.1 |
| 2016/0042835 A1* | 2/2016 | Lustig | H05K 9/0084 174/105 R |
| 2018/0184035 A1* | 6/2018 | Kim | H04N 5/37452 |
| 2018/0224326 A1 | 8/2018 | Dumont et al. | |
| 2018/0271401 A1* | 9/2018 | Greene | A61B 5/0507 |
| 2018/0353770 A1* | 12/2018 | Moffat | A61N 5/0616 |
| 2019/0204146 A1* | 7/2019 | Wei | G01J 1/0219 |
| 2019/0357277 A1* | 11/2019 | Park | H04B 7/26 |
| 2020/0376152 A1* | 12/2020 | Krosney | A61L 9/20 |

OTHER PUBLICATIONS

Kwon et al., Miniaturized, light-adaptive, wireless dosimeters autonomously monitor exposure to electromagnetic radiation, Sci. Adv., 5, 2019, 1-9.
Korean Intellectual Property Office (ISR/KR), "International Search Report for PCT/US2020/012241", Korea dated May 6, 2020.
A. C. Green, S. C. Wallingford, P. McBride, Childhood exposure to ultraviolet radiation and harmful skin effects: epidemiological evidence. Progress in Biophysics and Molecular Biology 107, 349-355 (2011).
B. K. Armstrong, A. Kricker, The epidemiology of UV induced skin cancer. J. Photochemistry and Photobiology B: Biology 63, 8-18 (2001).
J. D'Orazio, S. Jarrett, A. Amaro-Ortiz, T. Scott, UV radiation and the skin. Int. J. Molecular Sci. 14, 12222-12248 (2013).
G. P. Guy Jr, S. R. Machlin, D. U. Ekwueme, K. R. Yabroff, Prevalence and costs of skin cancer treatment in the US, 2002-2006 and 2007-2011. American J. Preventive Med. 48, 183-187 (2015).
F. Liebel, S. Kaur, E. Ruvolo, N. Kollias, M. D. Southall, Irradiation of skin with visible light induces reactive oxygen species and matrix-degrading enzymes. J. Investigative Dermatology 132, 1901-1907 (2012).
Y. Nakashima, S. Ohta, A. M. Wolf, Blue light-induced oxidative stress in live skin. Free Radical Biology and Med. 108, 300-310 (2017).
C. Regazzetti, L. Sormani, D. Debayle, F. Bernerd, M. K. Tulic, G. M. De Donatis, B. Chignon-Sicard, S. Rocchi, T. Passeron, Melanocytes sense blue light and regulate pigmentation through opsin-3. J. Investigative Dermatology 138, 171-178 (2018).
W. Noell, W. Walker, B. Kang, S. Berman, Retinal damage by light in rats. Invest Ophthalmol 5, 450-473 (1966).
W. K. Noell, Possible mechanisms of photoreceptor damage by light in mammalian eyes. Vision Res. 20, 1163-1171 (1980).
F. Behar-Cohen, C. Martinsons, F. Viénot, G. Zissis, A. Barlier-Salsi, J. P. Cesarini, O. Enouf, M. Garcia, S. Picaud, D. Attia, Light-emitting diodes (LED) for domestic lighting: Any risks for the eye? Progress in Retinal and Eye Res. 30, 239-257 (2011).
A. King, E. Gottlieb, D. G. Brooks, M. P. Murphy, J. L. Dunaief, Mitochondria-derived reactive oxygen species mediate blue light-induced death of retinal pigment epithelial cells. Photochemistry and Photobiology 79, 470-475 (2004).
B. F. Godley, F. A. Shamsi, F. Q. Liang, S. G. Jarrett, S. Davies, M. Boulton, Blue light induces mitochondrial DNA damage and free radical production in epithelial cells. J. Biological Chemistry 280, 21061-21066 (2005).
C. I. Eastman, Natural summer and winter sunlight exposure patterns in seasonal affective disorder. Physiology & Behavior 48, 611-616 (1990).
Y. Shi, M. Manco, D. Moyal, G. Huppert, H. Araki, A. Banks, H. Joshi, R. McKenzie, A. Seewald, G. Griffin, E. Sen-Gupta, D. Wright, P. Bastien, F. Valceschini, S. Seité, J. A. Wright, R. Ghaffari, J. Rogers, G. Balooch, R. M. Pielak, Soft, stretchable, epidermal sensor with integrated electronics and photochemistry for measuring personal UV exposures. PloS one 13, e0190233 (2018).
J. Heydenreich, H. C. Wulf, Miniature personal electronic UVR dosimeter with erythema response and time-stamped readings in a wristwatch. Photochemistry and Photobiology 81, 1138-1144 (2005).
S. Y. Heo, J. Kim, P. Gutruf, A. Banks, P. Wei, R. Pielak, G. Balooch, Y. Shi, H. Araki, D. Rollo, C. Gaede, M. Patel, J. W. Kwak, A. E. Peña-Alcántara, K.-T. Lee, Y. Yun, J. K. Robinson, S. Xu, J. A. Rogers, Wireless, battery-free, flexible, miniaturized dosimeters monitor exposure to solar radiation and to light for phototherapy. Sci. Transl. Med. 10, eaau1643 (2018).
A. Magnusson, D. Boivin, Seasonal affective disorder: an overview. Chronobiology Int. 20, 189-207 (2003).

(56) References Cited

OTHER PUBLICATIONS

G. Glickman, B. Byrne, C. Pineda, W. W. Hauck, G. C. Brainard, Light therapy for seasonal affective disorder with blue narrow-band light-emitting diodes (LEDs). Biological Psychiatry 59, 502-507 (2006).

D. F. Kripke, Light treatment for nonseasonal depression: speed, efficacy, and combined treatment. J. Affective Disorders 49, 109-117 (1998).

C. E. Remé, A. Wirz-Justice, M. Terman, The visual input stage of the mammalian circadian pacemaking system: I. Is there a clock in the mammalian eye? J. Biological Rhythms 6, 5-29 (1991).

A. Wirz-Justice, P. Graw, K. Kräuchi, A. Sarrafzadeh, J. English, J. Arendt, L. Sand, 'Natural' light treatment of seasonal affective disorder. J. Affective Disorders 37, 109-120 (1996).

S. Banerjee, E. G. Hoch, P. D. Kaplan, E. L .P. Dumont, A comparative study of wearable ultraviolet radiometers, 2017 IEEE Life Sciences Conference (LSC), Sydney, NSW, Australia, Dec. 3-15, 2017.

W. Zou, A. González, D. Jampaiah, R. Ramanathan, M. Taha, S. Walia, S. Sriram, M. Bhaskaran, J. M. Dominguez-Vera, V. Bansal, Skin color-specific and spectrally-selective nakedeye dosimetry of UVA, B and C radiations, Nature Communications, 9:3743 (2018).

\* cited by examiner

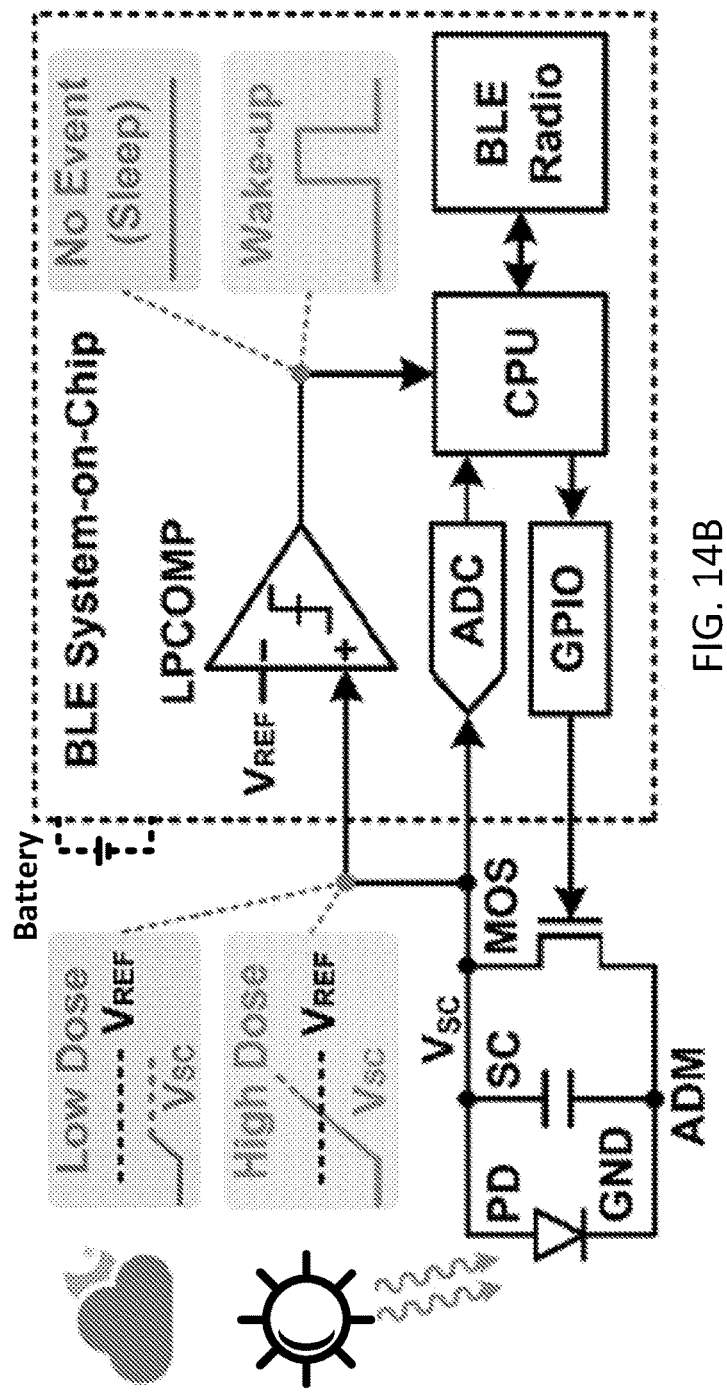
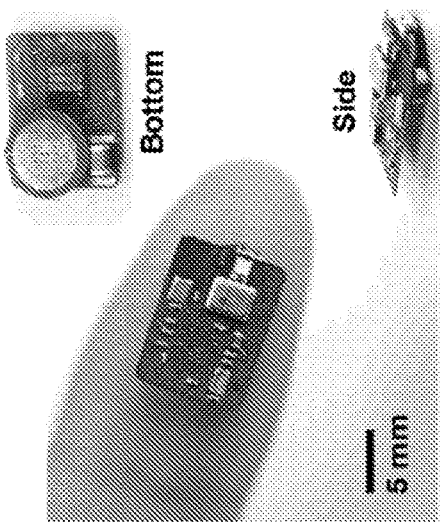
FIG. 14B
FIG. 14A

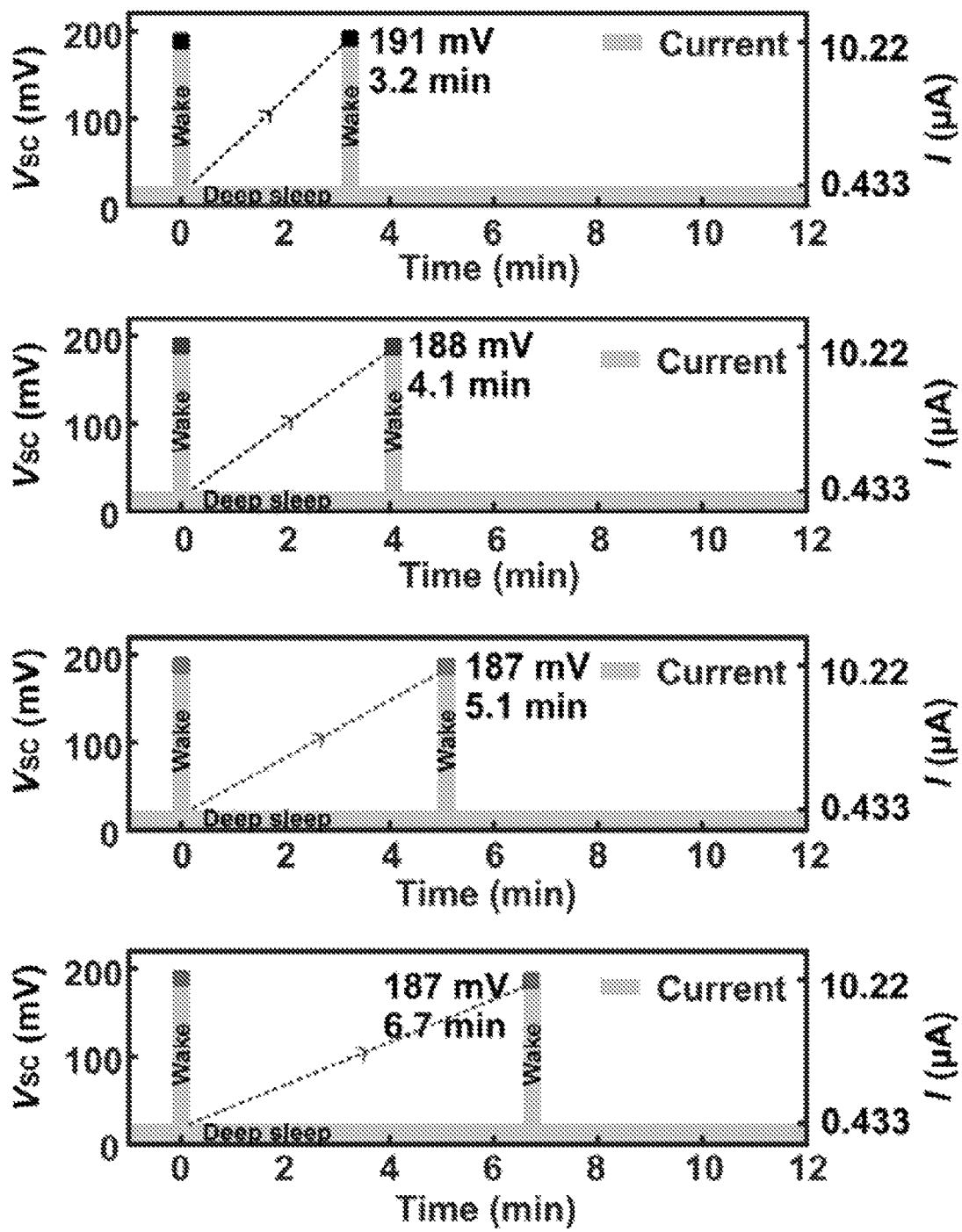

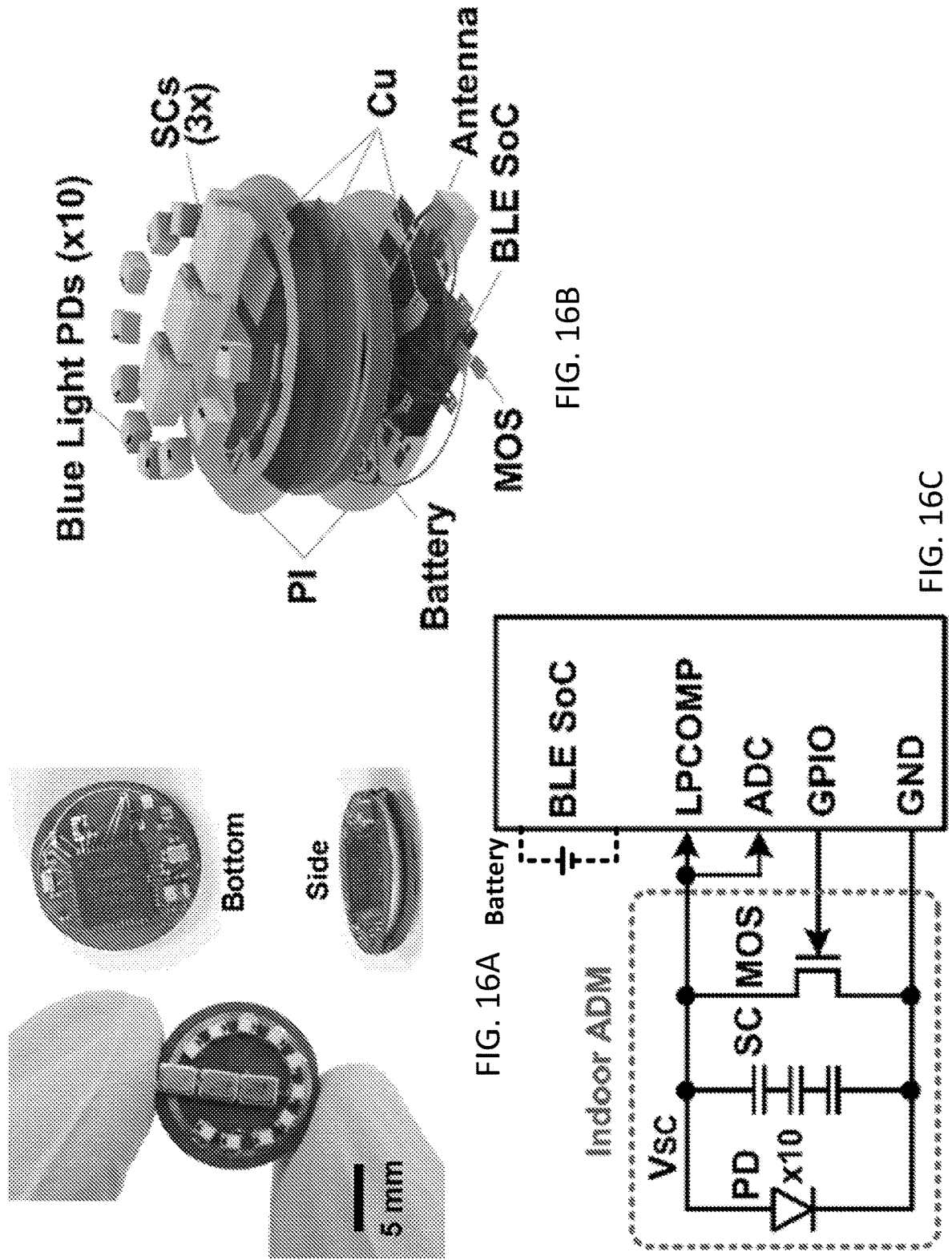

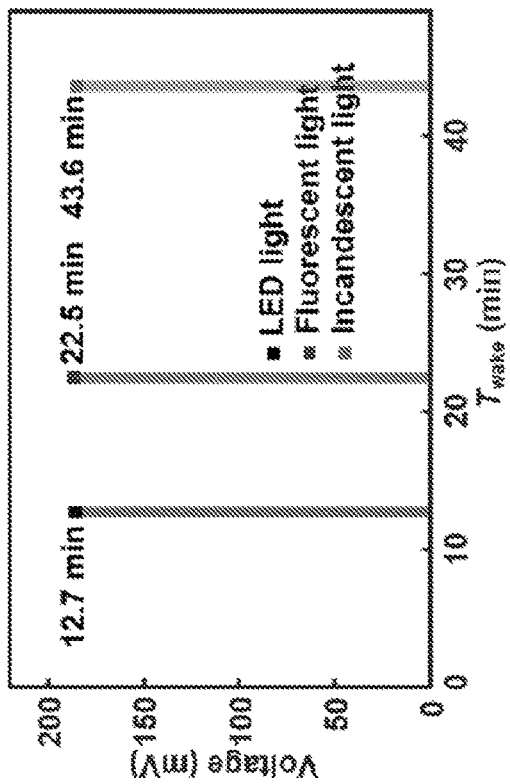
FIG. 16D
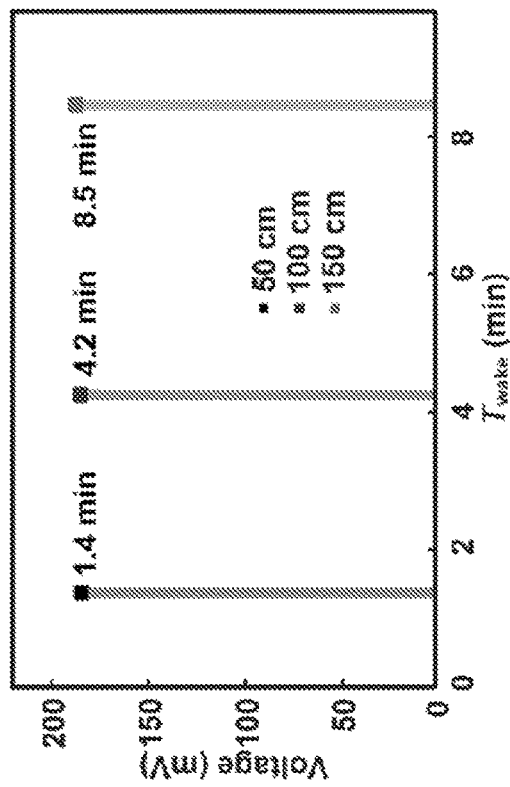
FIG. 16F
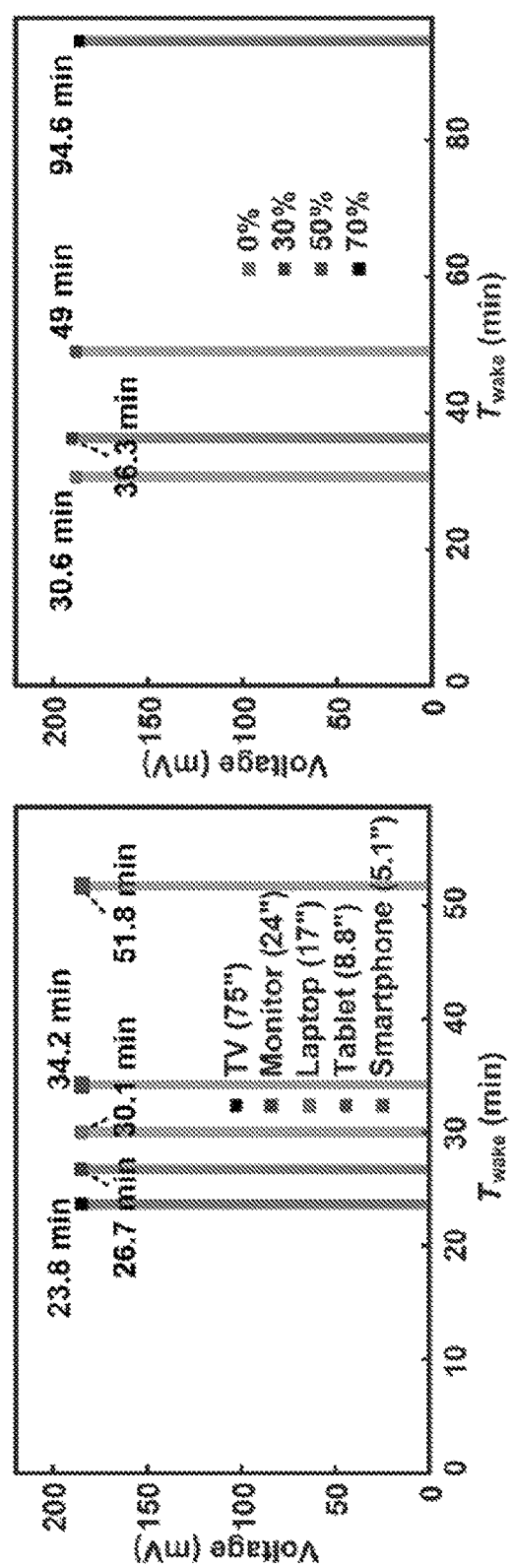
FIG. 16E
FIG. 16G

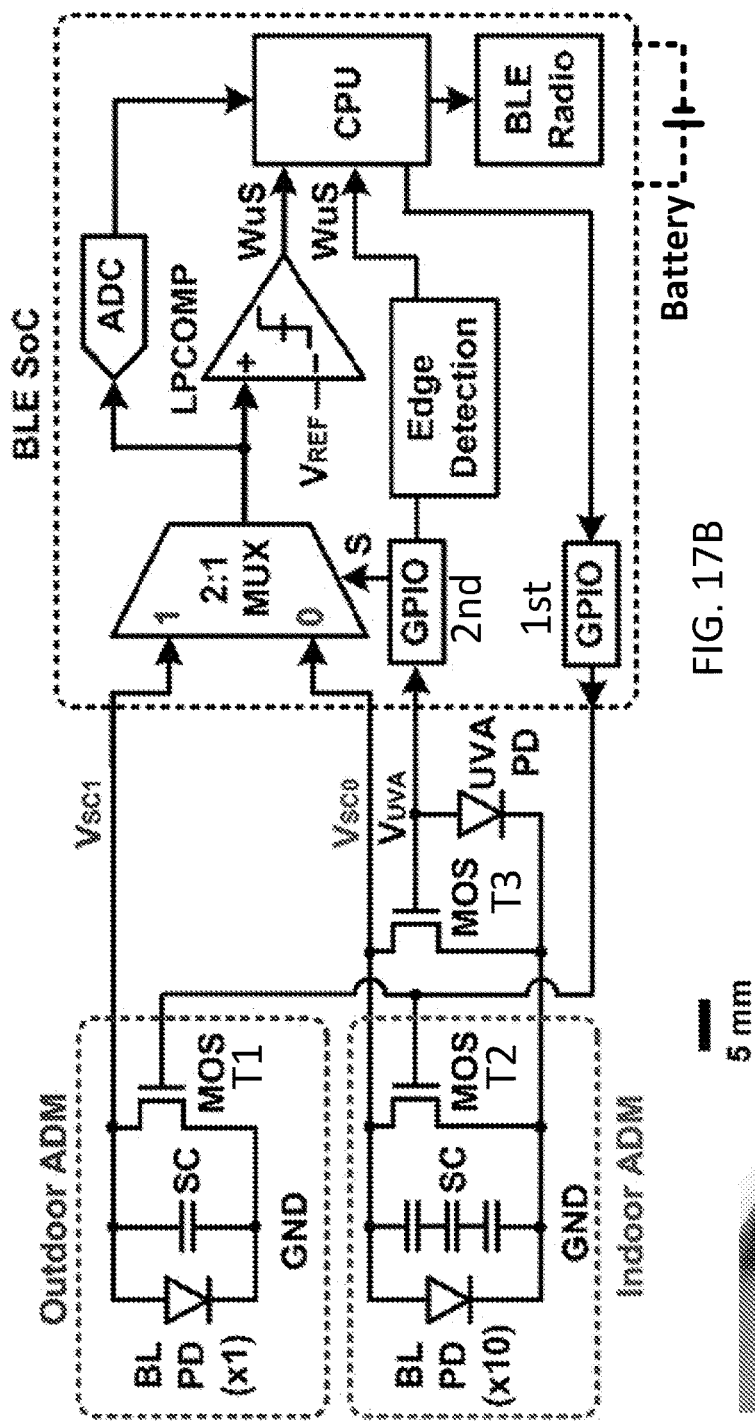
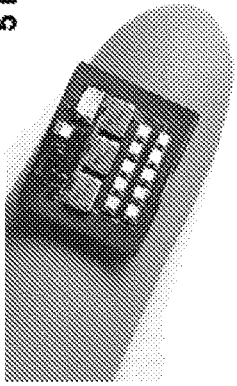
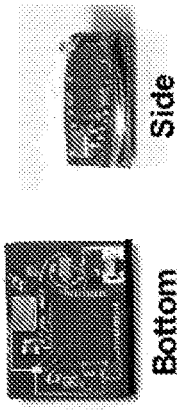
FIG. 17B
FIG. 17A

ULTRA-LOW POWER, MINIATURIZED ELECTRONIC SYSTEMS FOR MONITORING PHYSICAL PARAMETERS WITH WIRELESS COMMUNICATION CAPABILITIES AND APPLICATIONS OF SAME

CROSS-REFERENCE TO RELATED PATENT APPLICATION

This PCT application claims priority to and the benefit of U.S. Provisional Patent Application Ser. No. 62/787,964, filed Jan. 3, 2019, which is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

FIELD OF THE INVENTION

The invention relates generally to biosensors, and more particularly, to ultra-low power, miniaturized electronic systems for monitoring physical parameters with wireless communication capabilities and applications of the same.

BACKGROUND OF INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

Ultraviolet (UV) radiation is the primary driver of skin cancers, the most common human malignancy. Collectively, basal cell carcinoma and squamous cell carcinoma of the skin account for more than 5 million cases per year at a cost of US$8.1 billion yearly. Skin cancer is reaching epidemic proportions in the United States. Currently, there is a critical need for technologies that can accurately measure and promote safe UV exposure at a personalized level in naturalistic environments. This is particularly relevant in high risk groups including kidney transplant survivors who have a 65 times increased risk of certain skin cancers, the one million melanoma survivors in the United States who have a nine fold increased risk of developing a second melanoma, and people living with rare photosensitizing skin conditions (oculocutaneous albinism, cutaneous lupus erythematosus, and porphyria cutanea *tarda*).

UVB (280 to 315 nm) and UVA (315 to 400 nm) are the most relevant spectral ranges in the solar UV spectrum. Although both UVB and UVA are carcinogenic and contribute to skin aging, UVB is 1000 times more erythrogenic, with distinct biological effects to the skin compared to UVA irradiation, suggesting the need for differentiation of irradiances across the UV radiation spectrum. Beyond UVB and UVA, visible and infrared (IR) radiation in sunlight can lead to oxidative stresses that potentiate UV injury, skin darkening, and skin redness. Recent studies suggest that human circadian rhythm is highly sensitive to blue light exposure, affecting sleep cycle and alertness. These collective effects motivate the need for technologies that enable the precise quantification of natural sunlight exposure not only broadly across the UV range but also with wavelength specific resolution that extends into the visible and IR regimes at a personal and actionable level. Devices of this type could allow consumers to modulate their sun exposure based on individual activities, geographic locations, time of day, skin type, and medical conditions. The result would enable informed engagement in sun protective behaviors specific to the individual and their microenvironment before the development of clinically evident skin erythema, such as increasing sunscreen use or seeking shade.

Current approaches to individualized monitoring focus only on UV, typically including both UVA and UVB in a single combined measurement, and require wearables in the form of badges or wrist bands. Conventional, battery powered electronics in these systems facilitate wireless operation and digital data collection using photo detectors and memory modules, where collective costs can be excessive. Furthermore, the limited lifetimes of the batteries, their need for recharging, and their susceptibility to heat, water, and other environmental conditions hinder usability, typically leading to device abandonment. Certain traditional wearables designed primarily for other purposes offer UV sensing as additional functionality with incremental costs but with the same drawbacks as specialized dosimeters. The devices adopt form factors that require straps to the wrist, chest, or waist or that require clips that affix to clothing or personal accessories. In all cases, the necessary protective pack aging for the complex assembly of electronics provides only modest protection against water immersion and physical impact. Robust functionality during water recreation and outdoor sports is critical because of the increased risks of sunburn and excessive UV expo sure. The shortcomings of these devices lead to improper or discontinued use by consumers or prevent adoption. Devices in practice have limited utility in minimizing risks of overexposure, sunburn, and skin cancer.

As an alternative that addresses some of these deficiencies, recent research demonstrated capabilities in quantitative, continuous exposure monitoring using thin, skin like patches that incorporate colorimetric chemical reagents for UV dosimetry. Although these systems overcome certain drawbacks of conventional digital devices, their accuracy is limited by the colorimetric nature of the measurement, and they are restricted to single use operation. A critical unmet need is a broadly adoptable, low cost, miniaturized, and accurate system to enable informed protection from the sun, ideally with a continuous and accumulative mode of digital measurement at multiple discrete wavelength bands, with data analysis algorithms and user responsive software interfaces capable of influencing healthy behavior that can be deployed on multiple parts of the body.

Therefore, a heretofore unaddressed need exists in the art to address the aforementioned deficiencies and inadequacies.

SUMMARY OF THE INVENTION

In one aspect, the invention relates to an electronic system for monitoring a physical parameter. In one embodiment, the electronic system includes an accumulation detection module (ADM) for continuously measuring the physical parameter in terms of exposure dose in an accumulation mode. The ADM is a light-powered sensing system comprising at least one photodiode (PD) for continuously generating photocurrent with a magnitude that is proportional to an intensity of electromagnetic radiation in response to exposure to the electromagnetic radiation (EMR), at least one capacitor coupled to the at least one PD in parallel for storing charges accumulated from the generated photocurrent of the at least one PD, and at least one transistor having a source and a drain coupled to the at least one capacitor.

The electronic system also includes a power source for operably providing power; and a system on a chip (SoC) coupling with the ADM and the power source and operably in a sleep mode in which a minimal power is consumed, or in a run mode. The SoC comprises a wireless communication module, at least one analog-to-digital converter (ADC) and a low-power comparator (LPCOMP) coupled to the source of the at least one transistor, and a controller coupled to the at least one ADC, the LPCOMP and the wireless communication module, and is configured such that in operation, the LPCOMP monitors a voltage across the at least one capacitor when the SoC operates in the sleep mode, and when the voltage is equal to or greater than a pre-defined threshold, generates a wake-up event that triggers the SoC to operate in the run mode in which the controller wirelessly transmits a signal of the voltage converted by the at least one ADC to a receiver through the wireless communication module, activates the at least one transistor to discharge the at least one capacitor and then returns the SoC to the sleep mode.

In one embodiment, the SoC further comprises at least one general-purpose input/output (GPIO) coupled between a gate of the at least one transistor and the controller for operably activating the at least one transistor to discharge the at least one capacitor.

In one embodiment, the at least one PD comprises a plurality of PDs, and each PD is responsive to a respective wavelength region of the electromagnetic radiation. The ADM is characterized with a plurality of channels, and each channel has a respective one of the plurality of PDs, one of the at least one capacitor coupled to said respective PD and one of the at least one transistor coupled to said capacitor, for measuring the exposure dose of said respective wavelength region of the electromagnetic radiation.

In one embodiment, the plurality of PDs comprises an UVA PD, a blue PD, and an infrared (IR) PD.

In one embodiment, the at least one ADC comprises a plurality of ADCs, and each ADC is electrically couple to a respective one of the plurality of channels. The LPCOMP is configured to monitor the voltage in one of the plurality of channels, such that when the voltage is equal to or greater than the pre-defined threshold, the SoC enters the run mode and wirelessly transmits signals output from all the plurality of ADCs and simultaneously discharges said capacitors of all the plurality of channels.

In one embodiment, the at least one PD comprises a plurality of PDs, the at least one capacitor comprises a plurality of capacitors and the at least one transistor comprise a first and second transistors, where the ADM is characterized with an outdoor ADM and an indoor ADM for monitoring the exposure outdoors and indoors, respectively. The outdoor ADM has one of the plurality of PDs, one of the plurality of capacitors coupled to said PD and the first transistor coupled to said capacitor. The indoor ADM has the remaining PDs arranged in parallel, the remaining capacitors arranged in parallel and coupled to the remaining PDs and the second transistor coupled to the remaining capacitors.

In one embodiment, the indoor ADM and the outdoor ADM are paired with a UVA PD and a third transistor and operably switchable based on the presence or absence of UVA radiation, where the presence or absence of UVA radiation results in a high or low value of a voltage, $V_{UVA}$, output from the UVA PD, respectively.

In one embodiment, the SoC is configured to automatically switch between the indoor ADM and the outdoor ADM through a two-to-one multiplexer, where the two-to-one multiplexer is configured to switch the ADM to the outdoor ADM when the voltage $V_{UVA}$ is in a high value, and to the indoor ADM when the voltage $V_{UVA}$ is in a low value.

In one embodiment, a source and a drain of the third transistor are coupled to a source and a drain of the second transistor, respectively, and the UVA PD is coupled between a gate and the drain of the third transistor, such that in the outdoor ADM, the third transistor continuously discharges the indoor ADM to prevent excessive charge buildup on the corresponding capacitors. In one embodiment, the SoC further comprises an edge detector coupled between the controller and the UVA PD for monitoring the value of the voltage $V_{UVA}$ and generating a wake-up signal upon a rising edge when the value goes from low to high, or a falling edge when the value goes from high to low, corresponding to indoor-to-outdoor or outdoor-to-indoor switches, respectively. At each and every indoor/outdoor switching, the wake-up signal causes the controller to discharge both the indoor and outdoor ADMs, to update a 1-bit flag value with '0' for indoor and '1' for outdoor that is passed to an user interface as an indicator of activation of the indoor or outdoor ADM, and then to enter the sleep mode.

In another aspect, the invention relates to an electronic system for monitoring a physical parameter. In one embodiment, the electronic system includes an ADM comprising at least one accumulation mode sensor for measuring the physical parameter by generating electrical energy associated with the physical parameter in response to a surrounding condition, and at least one energy storing device coupled to the at least one accumulation mode sensor for accumulatively storing the generated electrical energy; a power source for operably providing power; and an SoC coupling with the ADM and the power source, configured such that the stored electrical energy is monitored, and when the stored electrical energy is equal to or greater than a pre-defined threshold, a wake-up event is generated to trigger the SoC to operates in a run mode in which the physical parameter associated with the stored electrical energy is wirelessly transmitted to a receiver and the stored electrical energy in the energy storing device is discharged, and then the SoC returns to a sleep mode in which a minimal power is consumed.

In one embodiment, the electronic system is a dosimeter for monitoring exposure dose indoors, a dosimeter for adaptively monitoring exposure dose both outdoors and indoors, or a multichannel dosimeter for simultaneously monitoring exposure dose in different wavelength regions of electromagnetic radiation.

In one embodiment, the ADM further comprises at least one transistor coupled to the at least one energy storing device for operably discharging the at least one energy storing device.

In one embodiment, the SoC comprises a wireless communication module, a low-power comparator coupled to the at least one transistor, and a controller coupled to the low-power comparator and the wireless communication module, such that in operation, the low-power comparator monitors the stored electrical energy, and when the stored electrical energy is equal to or greater than the pre-defined electrical energy, generates a wake-up event that triggers the SoC to operate in the run mode in which the controller wirelessly transmits a signal associated with the stored electrical energy to a receiver through the wireless communication module, activates the at least one transistor to discharge the he at least one energy storing device and then returns the SoC to the sleep mode.

In one embodiment, the ADM operably measures exposure dose in a continuous fashion, without power consumption from the power source.

Certain aspects of the invention further provide an electronic system for monitoring one or more physical parameters. In one embodiment, the electronic system includes at least one accumulation detection module (ADM) for sensing the one or more physical parameters that are accumulatively stored in the form of electrical energy based on a magnitude of the physical parameters; a wireless communication module electronically coupled to the at least one ADM; a controller electronically couple to the at least one ADM module and the wireless communication module; and a power source electronically coupled to the wireless communication system, the controller and/or the at least one ADM to power the wireless communication module, the controller, and/or the at least one ADM. They are configured such that the stored electrical energy is monitored, and when the stored electrical energy is equal to or greater than a pre-defined threshold, a wake-up event is generated to trigger the electronic system to transmit the physical parameters wirelessly to a receiver and discharge the stored electrical energy, and then return to a sleep mode in which a minimal power is consumed. In one embodiment, at least one ADM comprises at least one accumulation mode sensor, and at least one energy storing device electrically coupled to the at least one accumulation mode sensor, and wherein the electrical energy is stored in the at least one energy storing device.

In one embodiment, the controller is a central processing unit (CPU) or a microcontroller.

In one embodiment, the wireless communication module comprises at least one of a Bluetooth® low energy (BLE) module and a near-field communication (NFC) module.

In one embodiment, the wireless communication module automatically and periodically transmits a measured dose of the physical parameter to the receiver without an active user intervention.

In one embodiment, the at least one accumulation mode sensor comprises one or more of optical sensors, piezoelectric crystals, triboelectric sensors, acoustic sensors, mechanical sensors, pressure sensors, thermoelectric sensors, temperature sensors, temperature gradient sensors, humidity sensors, air pollution sensors, sweat or fluid sensors, electrocardiogram (ECG), Electromyography (EMG), pulse oximetry, accelerometers, and electromagnetic energy sensors for selected wavelengths including from radio wavelengths to gamma ray wavelengths.

In one embodiment, the at least one energy storing device comprises one or more of capacitors, accumulators, and rechargeable and dischargeable batteries.

In one embodiment, the surrounding condition includes one or more of electromagnetic radiation from the sun and/or artificial sources, air quality, weather, sounds, movements, and environmental changes.

In one embodiment, the sleep mode is characterized with a deep sleep mode and a shallow sleep mode, where when the voltage or the stored electrical energy is less than the pre-defined threshold, the SoC operates in the deep sleep mode in which only the low-power comparator is energized a deep sleep sampling interval, and when the voltage or the stored electrical energy is sampled with a shallow sleep sampling interval and compared to the pre-defined threshold, and a wake-up event is generated when the voltage or the stored electrical energy is equal to or greater than the pre-defined threshold, the SoC operates in the shallow sleep mode in which the low-power comparator, an ADC sampler and a processer timer are energized. In one embodiment, the deep sleep mode has an average deep sleep current in the electronic system that is less than or equal to 10 µA. In one embodiment, the deep sleep sampling interval is greater than the shallow sleep sampling interval, where the shallow sleep sampling interval is less than or equal 5 minutes.

In one embodiment, the deep sleep sampling interval and the shallow sleep sampling interval are dynamically controllable and changeable depending on operating parameters including a geographic location of the electronic system, time of day, magnitude of the physical parameter being measured and/or a user characteristic. In one embodiment, the user characteristic is one or more of skin type, sun protection parameter, age of user, ingestion of a sensitizing agent, and user sensitivity. In one embodiment, the geographic location is a field of agriculture, a museum, a beach, an outdoor venue, a sporting competition, adjacent to an industrial plant, energy plant, an agricultural grow region, UV water purification, UV sterilization, a sauna, a spa, a workout facility, a gymnasium, a gameroom, a hospital, or a rehabilitation facility.

In one embodiment, the pre-defined threshold that triggers the SoC to operate from the sleep mode to the run mode is hard programmed on the SoC, or remotely set through the receiver.

In one embodiment, the receiver is configured to receive an input of the user characteristic to dynamically vary the pre-defined threshold that controls a switch between the deep sleep mode and the shallow sleep mode.

In one embodiment, the receiver is one or more of a mobile device including a smart phone and a laptop or tablet, and a fixed receiver including a BLE system or beacon, cellular data transmission stations, a computer and a data center. The data center can be a database, data server, and/or cloud data center.

In one embodiment, the SoC further comprises a memory for storing the physical parameter to avoid unexpected data loss due to disruption of the wireless communication to the receiver.

In one embodiment, the electronic system further comprises a user-controllable switch to switch the electronic system to a power-off state, where the user-controllable switch is a mechanical switch or a wirelessly-controllable switch.

In one embodiment, the electronic system further comprises an on board actuator to alert a user to a risk condition, where the actuator is one or more of a mechanical vibrator, an electric stimulator, and an optical light source. In one embodiment, the alert is communicated to the receiver.

In one embodiment, the electronic system has an instantaneous mode for short term monitoring of the physical parameter. In one embodiment, the electronic system has a form factor that allows for a surface area profile of less than 3 cm. In one embodiment, the electronic system has an effective diameter less than 2.5 cm and a thickness less than 1 cm.

In one embodiment, the electronic system is partially or completely encapsulated by one or more encapsulation layers for thermal isolation, pressure isolation, pollutant isolation, electrical isolation and/or high external radiation isolation.

In one embodiment, the electronic system further comprises means for awaking an electronic system from a deep sleep mode. The awaking means may include at least one light emitting diode (LED) or capacitor. Example is long term shelf life prior to being opened/taken out of the package.

In one embodiment, the electronic system is configured to operate for 2 months or more without replacing or recharging the power source, preferably, 1 year or more without replacing or recharging the power source.

In one embodiment, the electronic system is configured to operate with a power consumption that is at least 25% lower than that of a comparable system that incorporates a sensor that does not offer the accumulation mode of operation; and/or with an accuracy that is at least 25% better than that of a comparable system that incorporates a sensor that does not offer the accumulation mode of operation.

In one embodiment, the electronic system is configured to be wearable by a person and/or affixed to a skin surface.

In one embodiment, the electronic system is incorporated into a piece of jewelry, an accessory, a watch, a piece of clothing, and/or to be worn underneath a piece of clothing.

In one embodiment, the physical parameter is one or more of exposure to UV radiation, physical motion, temperature, heat index, thermoregulation, skin hydration, sweat loss, electrolyte level, humidity, air pollution, chemical exposure, acoustic level, magnetic exposure, radiation exposure, visible light, heat, heat flux, metabolic expenditure, vibratory motion, mechanical shock, and rates of change thereof.

In yet another aspect, the invention relates to a system for monitoring one or more physical parameters, comprising a plurality of electronic systems deployed in a plurality of spatial-apart locations of interest. In one embodiment, the plurality of electronic systems is worn on or connected to skin of a user at plurality of distinct skin locations. Each electronic system can be any one disclosed above.

In another embodiment, the plurality of spatial-apart locations of interest is in a field of agriculture, a museum, a beach, an outdoor venue, a sporting competition, adjacent to an industrial plant, energy plant, an agricultural grow region, UV water purification, UV sterilization, a sauna, a spa, a workout facility, a gymnasium, a gameroom, a hospital, or a rehabilitation facility.

In a further aspect, the invention relates to a method of monitoring a physical parameter with an electronic system. In one embodiment, the method comprises the steps of continuously measuring a physical parameter with at least accumulation mode sensor by generating electrical energy associated with the physical parameter in response to a surrounding condition, and accumulatively storing the generated electrical energy in at least one energy storing device that is coupled to the at least one accumulation mode sensor; periodically comparing the stored electrical energy to a pre-defined threshold; and entering the electronic system in an deep sleep mode when the stored electrical energy is less than the pre-defined threshold; otherwise generating a wake-up event to trigger the electronic system to wirelessly transmit the physical parameter associated with the stored electrical energy to a receiver and to discharge the stored electrical energy in the energy storing device, and then to return to the deep sleep mode.

In one embodiment, when the stored electrical energy is equal to or greater than the pre-defined threshold, the electronic system is in a shallow-sleep mode in which all electronic components in the electronic system, except for an ADC and a timer, wait in a halt status.

In one embodiment, the method further comprises the steps of evaluating from the ADC a ready interrupt condition, thereby waking a controller to read a value, $V_{SC}$, of the ADC and compare $V_{SC}$ to the pre-defined threshold $V_{REF}$ and for $V_{SC} \geq V_{REF}$ send the physical parameter to the receiver, reset the at least accumulation mode sensor by discharging the at least one energy storing device, trigger the shallow sleep mode and provide a shallow sleep sampling interval; for $V_{SC} < V_{REF}$ enter in the deep sleep mode in which only a low power comparator is energized with a deep sleep sampling interval that is greater than a shallow sleep sampling interval.

In one embodiment, the method also includes the step of providing an instantaneous monitoring mode in which sensor output is continuously and instantaneously communicated to the receiver for short-term monitoring.

In one embodiment, the short-term monitoring is manually triggered by a user or is automatically triggered by a measured physical parameter that is greater than or equal to a user-selected reference level physical parameter.

In one embodiment, the electronic system is a dosimeter for monitoring exposure dose indoors, a dosimeter for adaptively monitoring exposure dose both outdoors and indoors, or a multichannel dosimeter for simultaneously monitoring exposure dose in different wavelength regions of electromagnetic radiation.

In one embodiment, the electronic system is attached on a skin surface or incorporated into an article of clothing or an accessory worn on a body.

In one embodiment, the method also includes the step of alerting a user wearing the electronic system as to exceeding a safe physical parameter exposure.

In one embodiment, the user wears a plurality of electronic systems over specific distinct skin locations.

In one embodiment, the method also includes the step of providing a user-characteristic to the receiver, where the user-characteristic is used to automatically determine the pre-defined threshold $V_{REF}$ tailored to the user.

In yet a further aspect, the invention relates to a non-transitory tangible computer-readable medium storing instructions which, when executed by one or more processors, cause the above-disclosed method to be performed.

These and other aspects of the invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein. The drawings described below are for illustration purposes only. The drawings are not intended to limit the scope of the present teachings in any way.

FIG. 13B describes how wireless communication protocols beyond BLE and NFC might work for a multiplex of sensors transmitting to an external remote processor via a cellular link, according to embodiments of the invention. This leads to actuation of an external system (e.g. grow lights for agriculture) where it is brightened or darkened—leading to continued sensing by the sensors creating a closed feedback loop. In addition, it can also be used for UV sensing in areas of ozone degradation, and IR sensing in geographically isolated locations or thermally active locations, and so on.

FIGS. 14A-14H show ultra-low power, light-adaptive, wireless blue light dosimeters, according to embodiments of the invention. FIG. 14A: Photograph of a blue light dosimeter with BLE communication capabilities on the tip of an index finger. The insets show bottom and side views. FIG. 14B: Circuit and block diagrams that illustrate accumulation mode, adaptive operation and wireless interface to smartphones (BLE radio). The accumulation detection module, photodiode, supercapacitor, MOSFET, and low-power comparator are labeled ADM, PD, SC, MOS, and LPCOMP, respectively. $V_{SC}$ and $V_{REF}$ denotes the accumulated voltage on SC and the reference voltage of LPCOMP, respectively. FIG. 14C: Illustration of $V_{SC}$ as a function of time during no light, weak light, and intense light exposure conditions, and activity of CPU and BLE radio at corresponding times. FIG. 14D: Schematic, exploded view illustration of the constituent layers and components: BLE System-on-Chip (SoC), battery, MOSFET (MOS), supercapacitor (SC), blue light photodetector (PD), copper interconnects (Cu/Pi/Cu), and chip antenna. FIG. 14E: Photographic image of three ultra-low power blue light dosimeters, next to respective batteries of capacities 140 mAh, 40 mAh, and 5.5 mAh (left to right). FIGS. 14F-14H: Photographs of encapsulated sensors mounted on a pair of glasses, an earring and a smart watch. Insets in FIG. 14H shows top and bottom views of the unencapsulated device.

FIGS. 15A-15C shows outdoor characterization and power consumption of blue light dosimeters, according to embodiments of the invention. FIG. 15A: Voltage outputs and current consumptions of an ultra-low power, blue light dosimeter (n=1) exposed to blue light over time with constant intensity at four different intensities corresponding to low and moderate blue light conditions outdoors. The time intervals ($T_{wake}$) to 'wake' the devices from a 'sleep' state when exposed to blue light with constant intensity of different levels are indicated. FIG. 15B: Average current consumption assuming continuous use ($I_{avg}$) and average current consumption assuming use corresponding to 50% of available daylight ($I_{avg,50\%}$) as a function of $T_{wake}$. FIG. 15C: Projected lifetime as a function of $T_{wake}$ for batteries of capacities 140 mAh, 40 mAh, and 5.5 mAh assuming use corresponding to 50% of available daylight: lifetime=battery capacity/$I_{avg,\ 50\%}$.

FIGS. 16A-16G show indoor characterization of light-powered, accumulation mode detection blue light dosimeters, according to embodiments of the invention. FIG. 16A: Photograph of an indoor blue light dosimeter held between the fingertips. FIG. 16B: Schematic, exploded view illustration of the constituent layers and components: BLE SoC, battery, a MOSFET (MOS), SCs (×3), blue light PDs (×10), copper interconnects (Cu/Pi/Cu), and chip antenna. FIG. 16C: Circuit and block diagrams of the system and its wireless interface to BLE-enabled devices for blue light monitoring indoors. FIGS. 16D-16G: Voltage output and wake-up time interval of an indoor blue light dosimeter (n=1) placed at a distance of 50 cm, 100 cm, and 150 cm from a white light phototherapy lamp (FIG. 16D), at a distance of 50 cm from artificial light sources (FIG. 16E), at a distance of 10 cm from display screens (FIG. 16F), and at a distance of 5 cm away from a tablet display equipped with 0%, 30%, 50%, and 70% blue light blocking filter (FIG. 16G). The $T_{wake}$ values are labeled.

FIGS. 17A-17D show outdoor/indoor dual use blue light dosimeters with an automated, wireless sensitivity-switching scheme, according to embodiments of the invention. FIG. 17A: Photographic image of a blue light dosimeter with an automated sensitivity switching scheme to allow monitoring of low intensity blue light indoors and high intensity blue light outdoors. FIG. 17B: Circuit and block diagrams of the system with wireless switching scheme between outdoor and indoor sensing circuits based on the presence or absence of UVA radiation. Blue light photodiode, MOSFET, supercapacitor, multiplexer, selection signal, the anode voltage of a UVA PD, and wake-up signal are labeled BL PD, MOS, SC, MUX, S, $V_{UVA}$, and WuS, respectively. FIG. 17C: Voltage and 1-bit flag (0' for indoor and '1' for outdoor) outputs as a function of time without UVA exposure (blue) and with UVA exposure (yellow). FIG. 17D: Voltage and 1-bit flag outputs as a function of time with daylight outdoors (yellow) and with a 60-LED ring light source (blue).

FIG. 18A: Photograph of an ultra-low power, 3-channel, UVA/blue/IR light dosimeter held between the finger-tips. FIG. 18B: Schematic, exploded view illustration of the constituent layers and components: the BLE system on a chip (BLE SoC), battery, MOSFETs (3×MOS), supercapacitors (3×SC), UVA photodetector (UVA PD), blue light PD, IR PD, copper interconnects (Cu/Pi/Cu), and chip antenna. FIG. 18C: Circuit and block diagrams of the adaptive, accumulation mode of detection and wireless interface to a remote BLE radio (i.e. smart phones). FIG. 18D: Photographs of a multichannel sensor mounted on ear phones. FIGS. 18E-18G: Measurements obtained from a UVA/blue/IR light dosimeter (n=1) as a function of time during morning (FIG. 18E), noon (FIG. 18F), and afternoon (FIG. 18G) hours in Evanston, Ill. on April, 2019.

FIG. 22A: Experimental setup for real-time current measurements on BLE blue light dosimeter. FIG. 22B-22D: Screenshots of Power Profiler Kits (PPK) application for the real-time current measurements on blue light dosimeter in 'run' mode (FIG. 22B), 'sleep' mode (FIG. 22C), and 'idle' mode (FIG. 22D).

FIG. 23A: Average current consumption assuming continuous use ($I_{avg}$) and average current consumption assuming use corresponding to 50% of available daylight ($I_{avg,50\%}$) in connected and advertising modes, as a function of $T_{wake}$. FIG. 23B: Projected lifetime as a function of $T_{wake}$ for batteries of capacities 5.5 mAh assuming use corresponding to 50% of available daylight in connected and advertising modes: lifetime=battery capacity/$I_{avg,50\%}$. Advertising-mode devices in the 50% exposure to the available daylight at a constant intensity of 7.8 mW/cm² achieves×3.0 lifetime compared to connected mode devices with an expected lifetime of 0.4 years.

FIG. 24A: Voltage output of Indoor ADM with 1 SC and 3 SCs in series separately arranged in parallel to 10 blue PDs over time with constant intensity of blue light exposure. FIG. 24B: System-level leakage current of two dosimeters that incorporates 1 SC and 3 SCs in series. The leakage current is defined as measured current necessary to maintain applied SC voltage bias of 50 mV, 100 mV, 150 mV, 200 mV, 250 mV, and 300 mV. The error bars represent the standard deviation. FIG. 24C: Photographic image of a subject in front of a white light phototherapy lamp wearing an indoor blue light dosimeter. The inset shows device mounted on the nose bridge of glasses. FIG. 24D: Measured time intervals ($T_{wake}$) between 'wake-up' events as a function of exposure distance (d) away from a white light phototherapy lamp. Fit to a functional form for (d, $T_{wake}$ [d]): $T_{wake}$ [d]=$T_{wake}$ [50 cm]×(d/50 cm)$^2$. FIG. 24E: Measured time intervals ($T_{wake}$) between 'wake-up' events as a function of % attenuation associated with a blue light blocking filter on a digital display. A tablet screen with blue light blocking filter with attenuation of 0%, 30%, 50%, and 70% as a source of exposure to an indoor blue light dosimeter placed 5 cm away from the screen to extrapolate $T_{wake}$. Fit to a functional form for (%, $T_{wake}$ [%]): $T_{wake}$ [%]=$T_{wake}$ [0]/(100−%)*100. FIG. 24F: Measured time intervals ($T_{wake}$) between 'wake-up' events with and without anti-blue light film. Here, a smartphone screen with and without anti-blue light film as a source of exposure to an indoor blue light dosimeter placed 5 cm away from the screen.

DETAILED DESCRIPTION OF THE INVENTION

Figure 1:
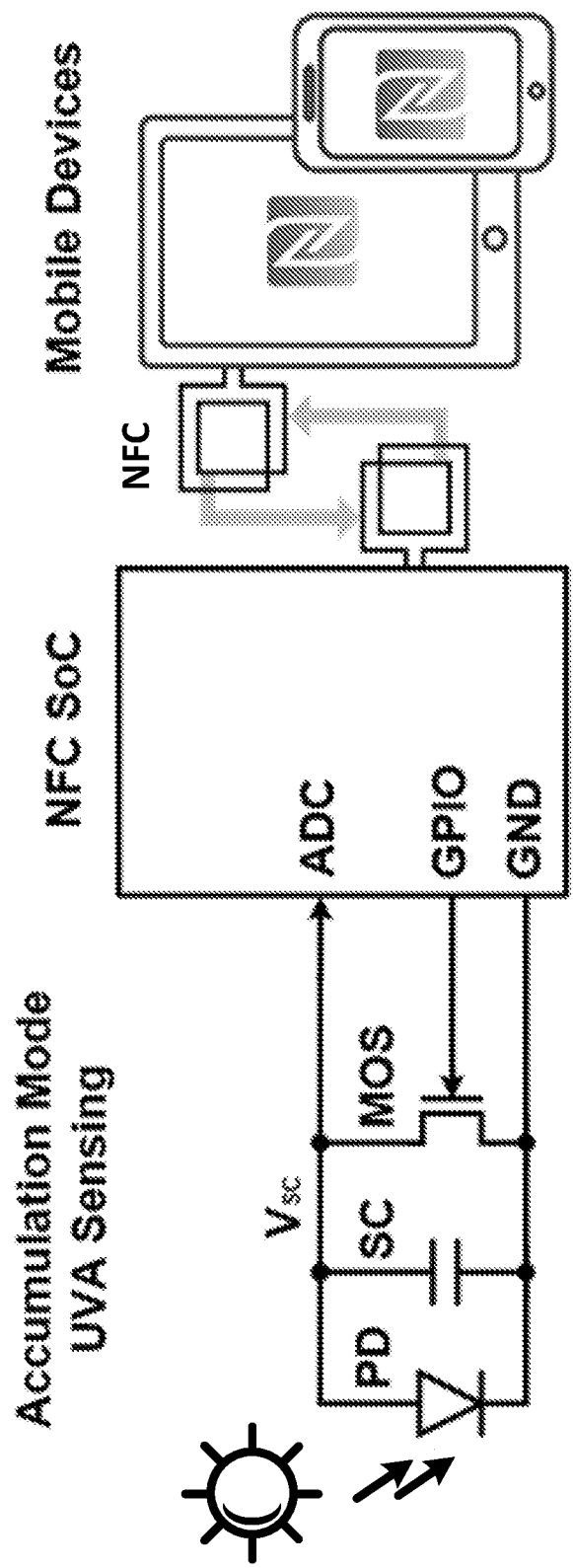
FIG. 1 shows circuit schematic of a battery-free dosimeter that includes a fully passive sensing circuit and near field communication (NFC) protocol to enable continuous exposure dose monitoring without power.

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present invention.

It will be understood that, as used in the description herein and throughout the claims that follow, the meaning of "a", "an", and "the" includes plural reference unless the context clearly dictates otherwise. Also, it will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used in this disclosure, "around", "about", "approximately" or "substantially" shall generally mean within 20 percent, preferably within 10 percent, and more preferably within 5 percent of a given value or range. Numerical quantities given herein are approximate, meaning that the term "around", "about", "approximately" or "substantially" can be inferred if not expressly stated.

As used in this disclosure, the phrase "at least one of A, B, and C" should be construed to mean a logical (A or B or C), using a non-exclusive logical OR. As used herein, the term "and/or" includes any and all combinations of one or more of the associated listed items.

As used in this disclosure, the term "long-term monitoring" refers to a wireless electronic system that can function reliably for a life time that is at least 6 months or longer, without any active maintenance, including battery recharge or replacement. As described herein, such long-term monitoring is provided herein using small form factor batteries by specially configured electronic configurations and sampling in a manner that maintains accuracy, while minimizing average power requirements.

Of course, any of the devices provided herein are compatible with short-term monitoring. "Short-term monitoring" may refer to a limited period of high frequency sampling, including ongoing and continuous transmission of sensor output to a receiver. Short-term monitoring also refers to the system entering into an instantaneous mode wherein there is real-time monitoring of the sensor output in a non-accumulating mode, such as for time-derivative parameters, including intensity. In this manner, the sensor output is not stored in the capacitor, but instead is monitored and output to the receiver. This also referred to as "instantaneous mode" sensing. Due to the increased power requirements of such instantaneous sensing, there is a power drain on the power source and so preferably there is an automated switch off of the instantaneous mode sensing, such as after a period that is not longer than 1 hour, 30 minutes, or 10 minutes. In this manner, unwanted shortening of battery lifetime is avoided. The different modes can be overridden, if desired, by a user.

As used in this disclosure, the term "accumulation mode" refers to the arrangement of a sensor whose electronic output is stored in a capacitor, thereby avoiding the need for frequent monitoring of sensor output, as well as advantageously being "self-powered." Instead, the electric potential across the supercapacitor can be less frequently monitored and, as required, the supercapacitor discharged so as to avoid over-storage and attendant leakage out of the supercapacitor. This combination of sensors and capacitors is also referred herein as a "self-powered transducer", reflecting the change of the magnitude of the physical parameter into an electrical output from the sensor, which is subsequently stored in the capacitor (or supercapacitor). The accumulation mode measures time-integral parameters, like dose, in contrast to the time-derivative parameters like intensity measured in an instantaneous mode.

As used in this disclosure, the term "instantaneous mode", in contrast, refers to the constant or at least very high frequency monitoring, of the real-time sensor output directly.

As used in this disclosure, the term "sleep mode" refers to the different states the system can have so as to maximize battery lifetime and, therefore, overall system lifetime. The different modes have different power requirements, with the instantaneous mode being highest, with a much lower power requirement in a sleep mode, such as shallow sleep, and an ultra-low power requirement for deep sleep modes. Of course, the lowest power requirement is for when the system is completely turned off.

As used in this disclosure, the term "deep sleep mode" refers to most of the system, including the communications module, being in an unenergized state, with only minimal low power requirements for the comparator and processor clock. In contrast, "shallow sleep mode" does have a higher power requirement reflecting the more active nature of the electronic system and communication with the receiver and sensor reset, as well as higher frequency sampling. Examples of various parameters, including sampling frequency and average current requirements, are summarized in Tables 1 and 2.

As used in this disclosure, the term "data package" refers to transmission of information relevant to the measurement of the physical parameter, such as magnitude and time, and may be used for further calculations, including rate of change, total exposure, flux and the like.

As used in this disclosure, the term "capacitor" refers to a material that can store charge and is typically formed from two conductive materials separated by a dielectric medium. A capacitor, as used herein, stores electrical charge and is capable of discharging as required, including when the stored charge is sufficiently high that there is a risk of substantial unwanted charge leakage. The term capacitor may be used interchangeably with the term "supercapacitor". "Supercapacitor", as used herein, refers to a high-capacity capacitor having a capacitance value that is much higher than conventional capacitors, such as the ability to store 10 to 100 times more energy per unit mass or volume, and can rapidly accept and deliver charge, while accommodating many charge and discharge cycles. Exemplary capacitors include those having a solid dielectric, an electrostatic double-layer capacitance (EDLC) (carbon or carbon-derivative electrodes), electrochemical pseudocapacitance (metal oxide or conducting polymer electrodes), hybrid capacitors that have electrodes with differing characteristics, such as lithium-ion capacitors. An advantage of the systems and methods provided herein is that they can readily incorporate a wide range of capacitors/supercapacitors, depending on the application of interest and corresponding energy storage characteristics, cycling number and lifetime.

As used in this disclosure, the term "sensing" refers to detecting the presence, absence, amount, magnitude or intensity of a physical and/or chemical property. Useful device components for sensing include, but are not limited to, electrode elements, chemical or biological sensor elements, pH sensors, temperature sensors, strain sensors, mechanical sensors, position sensors, optical sensors and capacitive sensors.

As used in this disclosure, the term "encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50%, or optionally 90% of the external surface of the structure is surrounded by one or more structures. "Completely encapsulated" refers to the orientation of one structure such that it is completely surrounded by one or more other structures.

As used in this disclosure, the term "physical parameter" is used broadly herein, and may be one or more of exposure to UV radiation, physical motion, temperature, heat index, thermoregulation, skin hydration, sweat loss, electrolyte level, humidity, air pollution, chemical exposure, acoustic level, magnetic exposure, radiation exposure, visible light, heat, heat flux, metabolic expenditure, vibratory motion, mechanical shock, and rates of change thereof.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

According to this invention, the combined use of adaptive circuit designs and accumulation detection schemes provide the foundations for compact, wireless digital platforms capable of continuous monitoring of exposure to the electromagnetic radiation (EMR) at a personalized level, across one or multiple wavelengths in an autonomous mode that adjusts continuously to surrounding conditions. These highly accurate, millimeter-scale systems function in an always-on state, with multi-year lifetimes that can be considered, in a practical sense, to be everlasting for most envisioned applications. Automatic reporting of exposure data via far-field wireless links to standard consumer electronic devices serves as the basis for information that can be used to guide healthy behaviors. These technical capabilities, taken together with a negligible user burden associated with data acquisition, power management, battery replenishment and wearability, represent an ideal collection of features. Alignment with low-cost, volume manufacturing suggest a potential for scaled deployment to help prevent risks of skin cancer, mood disorders, ocular damage and other conditions associated with EMR exposure.

One aspect of the invention provides an electronic system for monitoring a physical parameter. In some embodiments, as shown in FIGS. 1, 3, 5-10, 14A-14H, 16A-16C, 17A-17B, and 18A-18C, and particularly in FIGS. 5A-5B, the electronic system 100/200 includes an accumulation detection module (ADM) 120 for continuously measuring the physical parameter in terms of exposure dose in an accumulation mode. The ADM is a light-powered sensing system comprising at least one photodiode (PD) for continuously generating photocurrent with a magnitude that is proportional to an intensity of electromagnetic radiation in response to exposure to the electromagnetic radiation (EMR), e.g., emitted from a light surface 180, at least one capacitor (i.e., SC) coupled to the at least one PD in parallel for storing charges accumulated from the generated photocurrent of the at least one PD, and at least one transistor (i.e., MOS) having a source and a drain coupled to the at least one capacitor.

The electronic system 100/200 also includes a power source 130 for operably providing power; and a system on a chip (SoC) 110/210 coupling with the ADM 120 and the power source 130 and operably in a sleep mode in which a minimal power is consumed, or in a run mode. The SoC 110/210 comprises a wireless communication module, at least one analog-to-digital converter (ADC) and a low-power comparator (LPCOMP) coupled to the source of the at least one transistor, and a controller coupled to the at least one ADC, the LPCOMP and the wireless communication module, and is configured such that in operation, the LPCOMP monitors a voltage across the at least one capacitor when the SoC 110/210 operates in the sleep mode, and when the voltage is equal to or greater than a pre-defined threshold, generates a wake-up event that triggers the SoC 110/210 to operate in the run mode in which the controller wirelessly transmits a signal of the voltage converted by the at least one ADC to a receiver through the wireless communication module, activates the at least one transistor to discharge the at least one capacitor and then returns the SoC 110/210 to the sleep mode. The SoC 110/210 further comprises at least one general-purpose input/output (GPIO) coupled between a gate of the at least one transistor and the controller for operably activating the at least one transistor to discharge the at least one capacitor.

In one embodiment, the controller is a central processing unit (CPU) or a microcontroller.

Figure 5A:
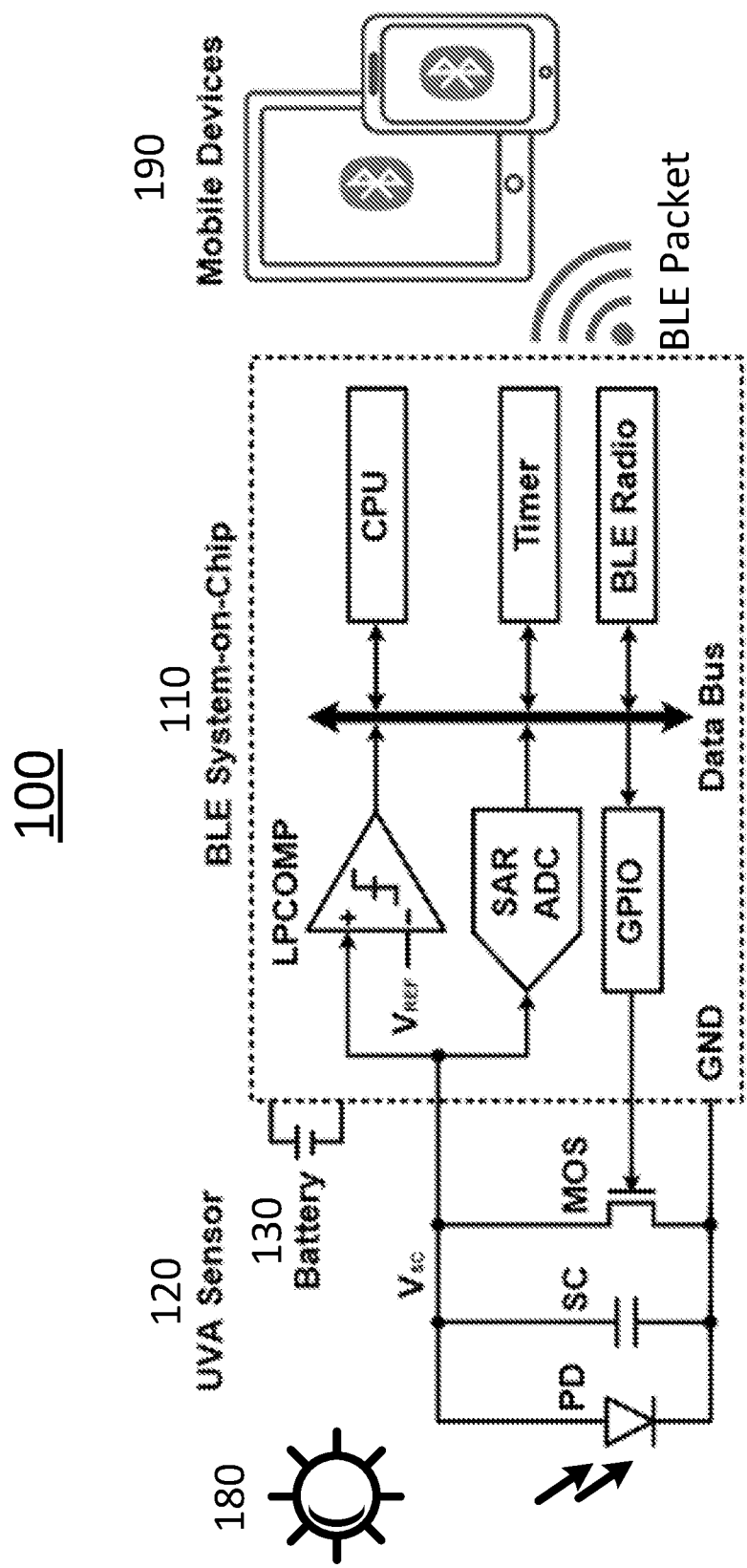
FIG. 5A shows a circuit diagram of an electronic system that is an 'accumulation mode' dosimeter, with a BLE radio, a power source, and a controller/receiver in wireless communication with the electronic system, according to embodiments of the invention.
Figure 5B:
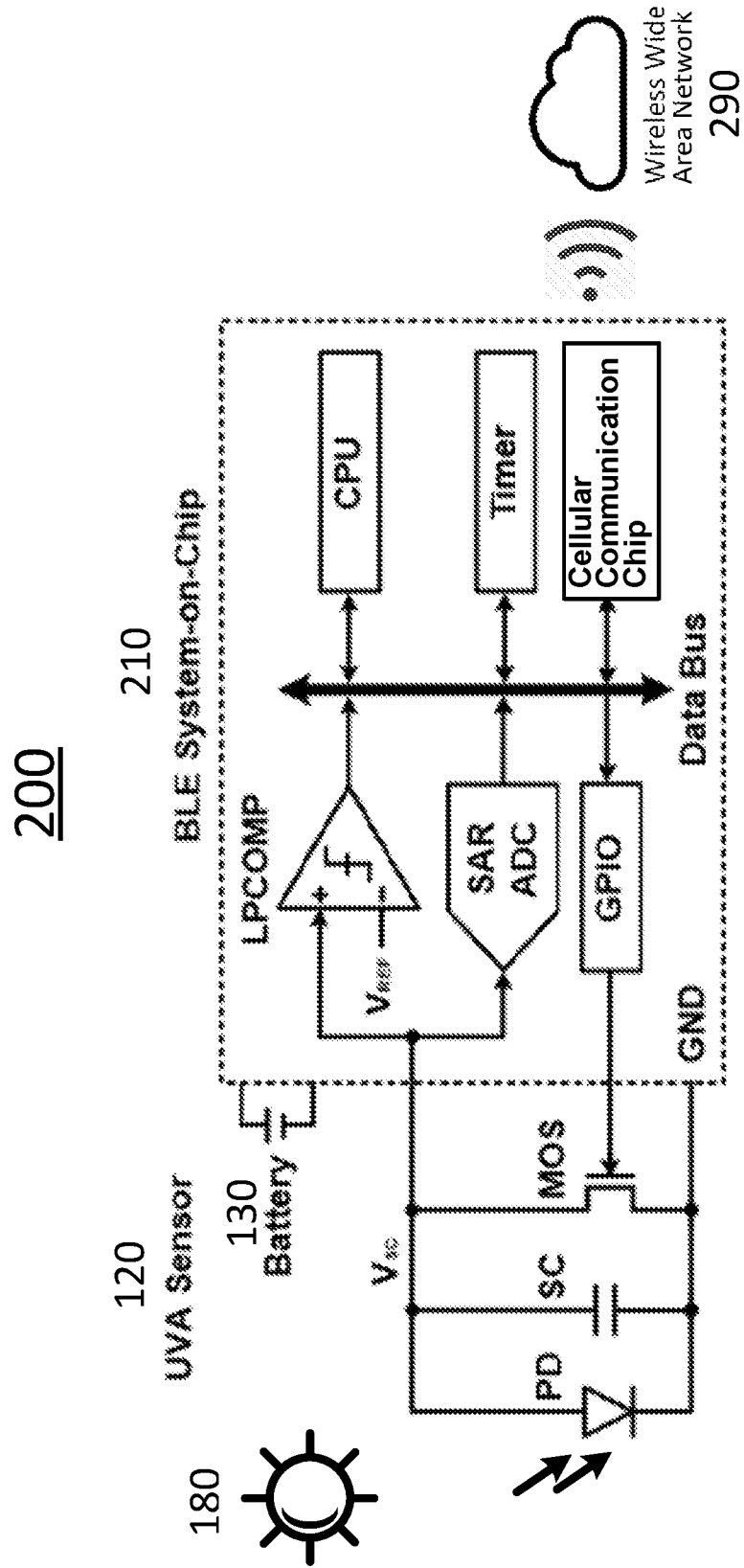
FIG. 5B shows a circuit diagram of an electronic system that is an 'accumulation mode' dosimeter, with a cellular communication chip, a power source, and a controller/receiver in wireless communication with the electronic system, according to embodiments of the invention

In one embodiment, the wireless communication module comprises a Bluetooth® low energy (BLE) module, for example, as shown in FIG. 5A. In some embodiments, the wireless communication module comprises a cellular communication module/chip having a direct cellular communication link with a wireless wide area network. Such cellular communication can be accomplished with, but not limited to, 2G, 3G, NB IoT, LTE-M, LTE Cat 1, 4G LTE, 5G, and/or modules, embedded into the electronic system/sensor. Accordingly, the measured physical parameter is transmitted to the receiver through wireless wide area network 290 as shown in FIG. 5B. In another embodiment, the wireless communication module may further comprise a near-field communication (NFC) module, for example, as shown in FIG. 1.

In one embodiment shown in 18A-18C, the at least one PD comprises a plurality of PDs, and each PD is responsive to a respective wavelength region of the electromagnetic radiation. The ADM includes a plurality of channels, and each channel has a respective one of the plurality of PDs, one of the at least one capacitor coupled to said respective PD and one of the at least one transistor coupled to said capacitor, for measuring the exposure dose of said respective wavelength region of the electromagnetic radiation. In this exemplary embodiment, the plurality of PDs comprises an UVA PD, a blue PD, and an infrared (IR) PD. In addition, the at least one ADC comprises a plurality of ADCs, and each ADC is electrically couple to a respective one of the plurality of channels, and wherein the LPCOMP is configured to monitor the voltage in one of the plurality of channels, such that when the voltage is equal to or greater than the pre-defined threshold, the SoC enters the run mode and wirelessly transmits signals output from all the plurality of ADCs and simultaneously discharges said capacitors of all the plurality of channels.

In one embodiment shown in FIGS. 17A-17B, the at least one PD comprises a plurality of PDs, the at least one capacitor comprises a plurality of capacitors and the at least one transistor comprise a first and second transistors. The ADM includes an outdoor ADM and an indoor ADM for monitoring the exposure outdoors and indoors, respectively. The outdoor ADM has one of the plurality of PDs, one of the plurality of capacitors coupled to said PD and the first transistor coupled to said capacitor. The indoor ADM has the remaining PDs arranged in parallel, the remaining capacitors arranged in parallel and coupled to the remaining PDs and the second transistor coupled to the remaining capacitors. In the exemplary embodiment, the indoor ADM and the outdoor ADM are paired with a UVA PD and a third transistor and operably switchable based on the presence or absence of UVA radiation. The presence or absence of UVA radiation results in a high or low value of a voltage, $V_{UVA}$, output from the UVA PD, respectively. Furthermore, the SoC is configured to automatically switch between the indoor ADM and the outdoor ADM through a two-to-one multiplexer, where the two-to-one multiplexer is configured to switch the ADM to the outdoor ADM when the voltage $V_{UVA}$ is in a high value, and to the indoor ADM when the voltage $V_{UVA}$ is in a low value. In addition, a source and a drain of the third transistor are coupled to a source and a drain of the second transistor, respectively, and the UVA PD is coupled between a gate and the drain of the third transistor, such that in the outdoor ADM, the third transistor continuously discharges the indoor ADM to prevent excessive charge buildup on the corresponding capacitors. In the exemplary embodiment, the SoC further comprises an edge detector coupled between the controller and the UVA PD for monitoring the value of the voltage $V_{UVA}$ and generating a wake-up signal upon a rising edge when the value goes from low to high, or a falling edge when the value goes from high to low, corresponding to indoor-to-outdoor or outdoor-to-indoor switches, respectively, and wherein at each and every indoor/outdoor switching, the wake-up signal causes the controller to discharge both the indoor and outdoor ADMs, to update a 1-bit flag value with '0' for indoor and '1' for outdoor that is passed to an user interface as an indicator of activation of the indoor or outdoor ADM, and then to enter the sleep mode.

In the exemplary embodiments discussed above, for illustration of the principle of the invention, the invented electronic system or accommodation mode sensor is applied to measure/monitor the exposure dose of UV light. It is noted that, according to the invention, the electronic system or accommodation mode sensor can also be applied to measure/monitor exposure of any environment condition to human, animals, agriculture, other objects such as artwork, paint plastics, and so on. The environment condition includes, but is not limited to, electromagnetic radiation from the sun and/or artificial sources such as welding, screens, lamps, machines and/or equipment, and industrial plants, fires, air pollution, and so on. The exposure dose can be used to determine/evaluate effects to the exposed human, animals, and other objects, air quality, weather, sounds, movements, and other environmental changes. In some embodiments, the electronic system or accommodation mode sensor also be used in healthcare, therapy, agriculture, museums, manufactories, labs, coal-fired power stations, gas-fired power stations, and nuclear plants, and so on.

Another aspect of the invention also provides an electronic system for monitoring a physical parameter. In one embodiment, the electronic system includes an ADM comprising at least one accumulation mode sensor for measuring the physical parameter by generating electrical energy associated with the physical parameter in response to a surrounding condition, and at least one energy storing device coupled to the at least one accumulation mode sensor for accumulatively storing the generated electrical energy; a power source for operably providing power; and an SoC coupling with the ADM and the power source, configured such that the stored electrical energy is monitored, and when the stored electrical energy is equal to or greater than a pre-defined threshold, a wake-up event is generated to trigger the SoC to operates in a run mode in which the physical parameter associated with the stored electrical energy is wirelessly transmitted to a receiver and the stored electrical energy in the energy storing device is discharged, and then the SoC returns to a sleep mode in which a minimal power is consumed.

The electronic system can be a dosimeter for monitoring exposure dose indoors, a dosimeter for adaptively monitoring exposure dose both outdoors and indoors, or a multi-channel dosimeter for simultaneously monitoring exposure dose in different wavelength regions of electromagnetic radiation.

In one embodiment, the ADM further comprises at least one transistor coupled to the at least one energy storing device for operably discharging the at least one energy storing device.

In one embodiment, the SoC comprises a wireless communication module, a low-power comparator coupled to the at least one transistor, and a controller coupled to the low-power comparator and the wireless communication module, such that in operation, the low-power comparator monitors the stored electrical energy, and when the stored electrical energy is equal to or greater than the pre-defined electrical energy, generates a wake-up event that triggers the SoC to operate in the run mode in which the controller wirelessly transmits a signal associated with the stored electrical energy to a receiver through the wireless communication module, activates the at least one transistor to discharge the he at least one energy storing device and then returns the SoC to the sleep mode.

In one embodiment, the ADM operably measures exposure dose in a continuous fashion, without power consumption from the power source.

Certain aspects of the invention further provide an electronic system for monitoring one or more physical parameters. In one embodiment, the electronic system includes at least one accumulation detection module (ADM) for sensing the one or more physical parameters that are accumulatively stored in the form of electrical energy based on a magnitude of the physical parameters; a wireless communication module electronically coupled to the at least one ADM; a controller electronically couple to the at least one ADM module and the wireless communication module; and a power source electronically coupled to the wireless communication system, the controller and/or the at least one ADM to power the wireless communication module, the controller, and/or the at least one ADM. They are configured such that the stored electrical energy is monitored, and when the stored electrical energy is equal to or greater than a pre-defined threshold, a wake-up event is generated to trigger the electronic system to transmit the physical parameters wirelessly to a receiver and discharge the stored electrical energy, and then return to a sleep mode in which a minimal power is consumed. In one embodiment, at least one ADM comprises at least one accumulation mode sensor, and at least one energy storing device electrically coupled to the at least one accumulation mode sensor, and wherein the electrical energy is stored in the at least one energy storing device. In one embodiment, the controller is a CPU or a microcontroller.

In one embodiment, the wireless communication module comprises at least one of a BLE module, a cellular commutation module, and a NFC module.

In one embodiment, the wireless communication module automatically and periodically transmits a measured dose of the physical parameter to the receiver without an active user intervention.

In one embodiment, the at least one accumulation mode sensor comprises one or more of optical sensors, piezoelectric crystals, triboelectric sensors, acoustic sensors, mechanical sensors, pressure sensors, thermoelectric sensors, temperature sensors, temperature gradient sensors, humidity sensors, air pollution sensors, sweat or fluid sensors, electrocardiogram (ECG), Electromyography (EMG), pulse oximetry, accelerometers, and electromagnetic energy sensors for selected wavelengths including from radio wavelengths to gamma ray wavelengths.

In one embodiment, the at least one energy storing device comprises one or more of capacitors, accumulators, and rechargeable and dischargeable batteries.

In one embodiment, the surrounding condition includes one or more of electromagnetic radiation from the sun and/or artificial sources, air quality, weather, sounds, movements, and environmental changes.

In one embodiment, the sleep mode is characterized with a deep sleep mode and a shallow sleep mode, wherein when the voltage or the stored electrical energy is less than the pre-defined threshold, the SoC operates in the deep sleep mode in which only the low-power comparator is energized a deep sleep sampling interval, and when the voltage or the stored electrical energy is sampled with a shallow sleep sampling interval and compared to the pre-defined threshold, and a wake-up event is generated when the voltage or the stored electrical energy is equal to or greater than the pre-defined threshold, the SoC operates in the shallow sleep mode in which the low-power comparator, an ADC sampler and a processer timer are energized. In one embodiment, the deep sleep mode has an average deep sleep current in the electronic system that is less than or equal to 10 µA. In one embodiment, the deep sleep sampling interval is greater than the shallow sleep sampling interval, wherein the shallow sleep sampling interval is less than or equal 5 minutes.

In one embodiment, the deep sleep sampling interval and the shallow sleep sampling interval are dynamically controllable and changeable depending on operating parameters including a geographic location of the electronic system, time of day, magnitude of the physical parameter being measured and/or a user characteristic. In one embodiment, the user characteristic is one or more of skin type, sun protection parameter, age of user, ingestion of a sensitizing agent, and user sensitivity. In one embodiment, the geographic location is a field of agriculture, a museum, a beach, an outdoor venue, a sporting competition, adjacent to an industrial plant, energy plant, an agricultural grow region, UV water purification, UV sterilization, a sauna, a spa, a workout facility, a gymnasium, a gameroom, a hospital, or a rehabilitation facility.

Figure 10:
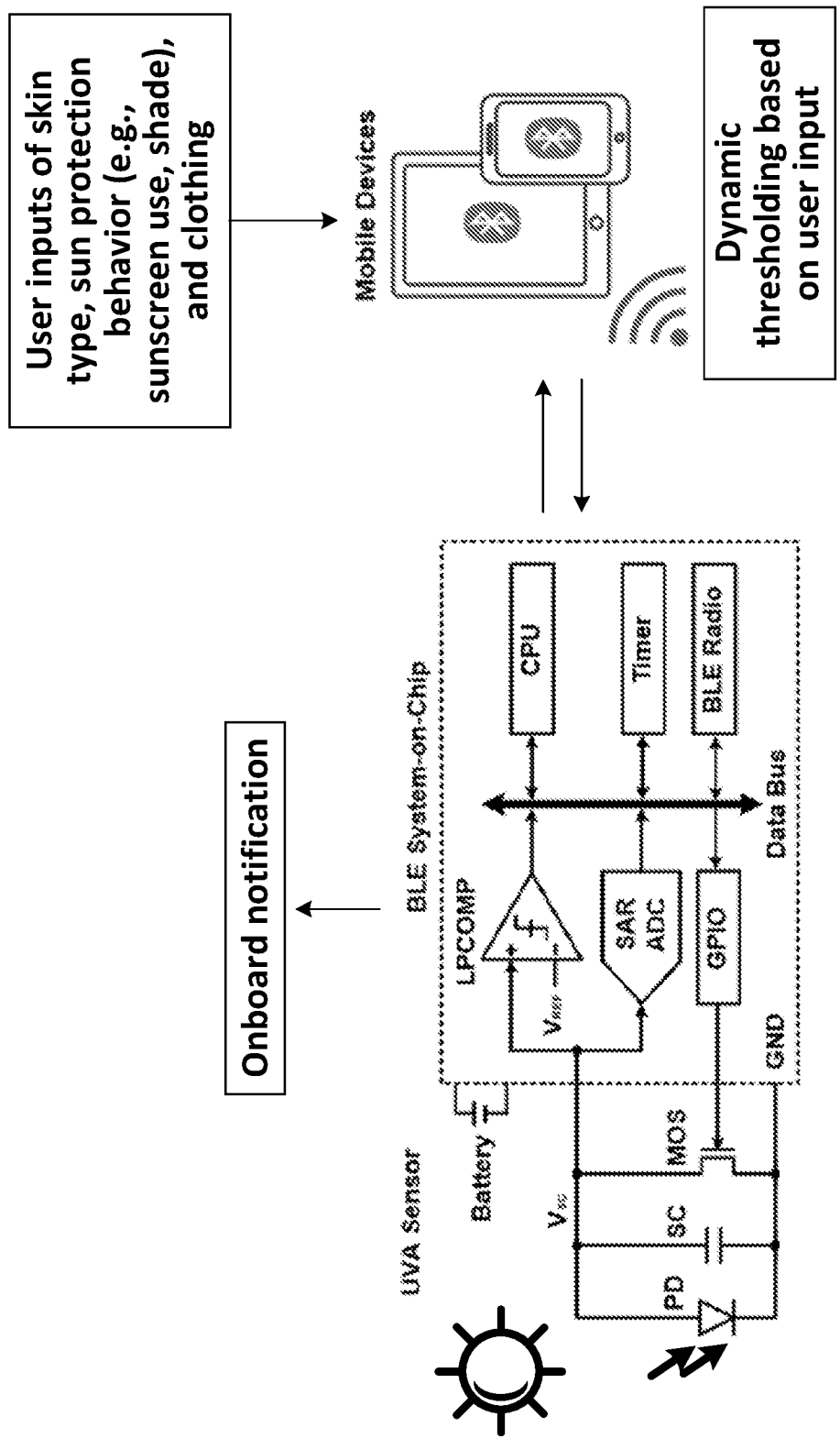
FIG. 10 shows threshold that triggers activation of the sensor from deep sleep to read the values on the supercapacitor can be hard programmed on the sensor or set through software on a mobile device, according to embodiments of the invention. The threshold can also be adaptive and personalized based on user inputs, such as on their skin type, behavior and other factors.

In one embodiment, the pre-defined threshold that triggers the SoC to operate from the sleep mode to the run mode is hard programmed on the SoC, or remotely set through the receiver, as shown in FIG. 10.

In one embodiment, the receiver is configured to receive an input of the user characteristic to dynamically vary the pre-defined threshold that controls a switch between the deep sleep mode and the shallow sleep mode.

In one embodiment, the receiver is one or more of a mobile device including a smart phone and a laptop or tablet, and a fixed receiver including a Bluetooth® low energy (BLE) system or beacon, cellular data transmission stations, a computer and a data center. The data center can be a database, data server, and/or cloud data center.

In one embodiment, the SoC further comprises a memory for storing the physical parameter to avoid unexpected data loss due to disruption of the wireless communication to the receiver.

In one embodiment, the electronic system further comprises a user-controllable switch to switch the electronic system to a power-off state, wherein the user-controllable switch is a mechanical switch or a wirelessly-controllable switch.

In one embodiment, the electronic system further comprises an on board actuator to alert a user to a risk condition, wherein the actuator is one or more of a mechanical vibrator, an electric stimulator, and an optical light source. In one embodiment, the alert is communicated to the receiver.

In one embodiment, the electronic system has an instantaneous mode for short term monitoring of the physical parameter. In one embodiment, the electronic system has a form factor that allows for a surface area profile of less than 3 cm. In one embodiment, the electronic system has an effective diameter less than 2.5 cm and a thickness less than 1 cm.

In one embodiment, the electronic system is partially or completely encapsulated by one or more encapsulation layers for thermal isolation, pressure isolation, pollutant isolation, electrical isolation and/or high external radiation isolation.

In one embodiment, the electronic system further comprises means for awaking an electronic system from a deep sleep mode. The awaking means may include at least one light emitting diode (LED) or capacitor. Example is long term shelf life prior to being opened/taken out of the package.

In one embodiment, the electronic system is configured to operate for 2 months or more without replacing or recharging the power source, preferably, 1 year or more without replacing or recharging the power source.

In one embodiment, the electronic system is configured to operate with a power consumption that is at least 25% lower than that of a comparable system that incorporates a sensor that does not offer the accumulation mode of operation; and/or with an accuracy that is at least 25% better than that of a comparable system that incorporates a sensor that does not offer the accumulation mode of operation.

In one embodiment, the electronic system is configured to be wearable by a person and/or affixed to a skin surface.

In one embodiment, the electronic system is incorporated into a piece of jewelry, an accessory, a watch, a piece of clothing, and/or to be worn underneath a piece of clothing.

Figure 11:
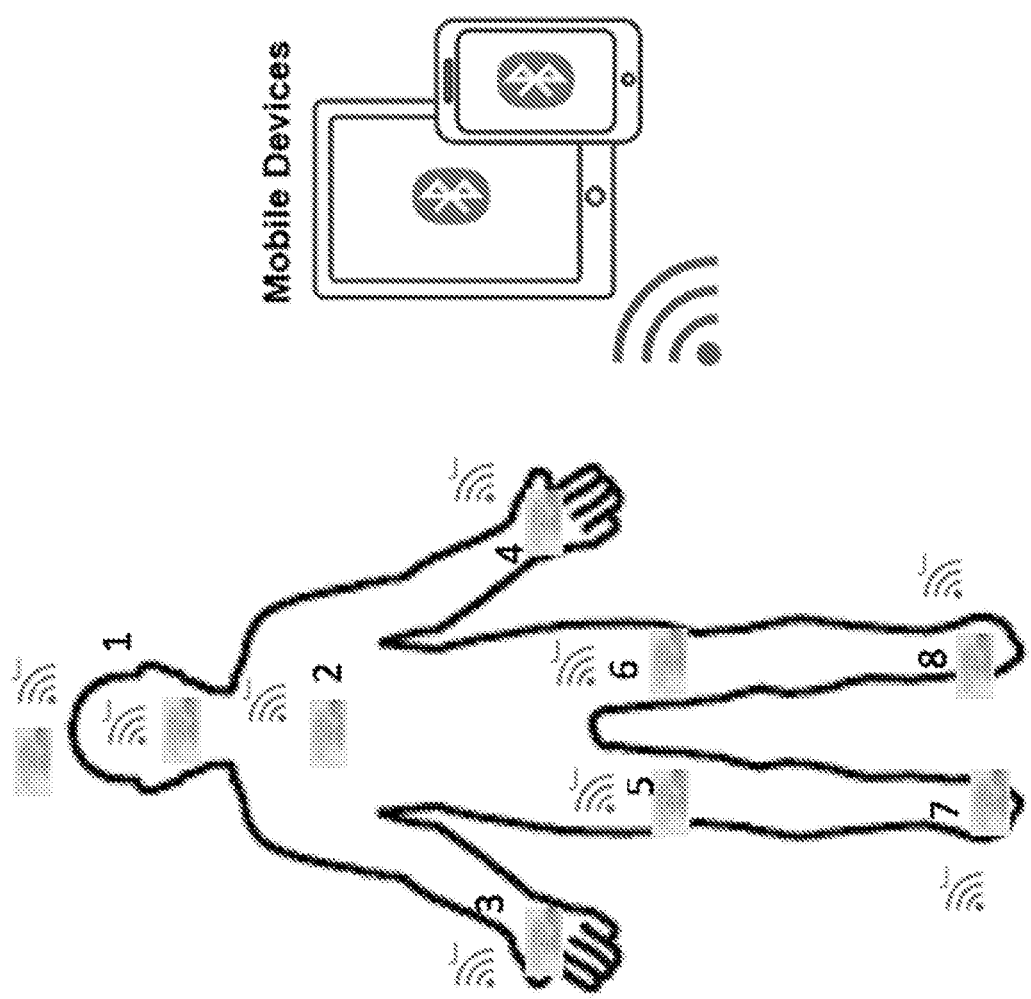
FIG. 11 shows the small form factor and passive nature of sensing allows for on-body, anatomical specific sensing, according to embodiments of the invention. This serves utility in research settings as well consumer health settings. The identification of high risk locations (e.g., face, hands, neck) can be identified by sensors placed strategically as jewelry (e.g., earrings, rings, necklaces). Sensors placed on the trunk, arms, or legs of a user can be located underneath clothing to identify instances where users may need to apply sunscreen or seek shade even with clothing on—clothing has variable amounts of UV protection. This embodiment allows a continuous stream of multi-sensor data which can then be displayed on the user interface of a mobile phone, such as a user's mobile phone or another person's handheld interested in the user (e.g., a parent, medical caregiver, or headquarter supervisor).

In addition, as shown in FIG. 11, a system for monitoring one or more physical parameters may have a plurality of electronic systems, for example, seven electronic systems, configured to be worn on or connected to skin of a user at plurality of distinct skin locations. Each electronic system can be any one disclosed above.

In another embodiment, the electronic systems may be deployed in a plurality of spatial-apart locations of interest in a field of agriculture, a museum, a beach, an outdoor venue, a sporting competition, adjacent to an industrial plant, energy plant, an agricultural grow region, UV water purification, UV sterilization, a sauna, a spa, a workout facility, a gymnasium, a gameroom, a hospital, or a rehabilitation facility.

One aspect of the invention also discloses a method of monitoring a physical parameter with an electronic system. In one embodiment, the method comprises the steps of continuously measuring a physical parameter with at least accumulation mode sensor by generating electrical energy associated with the physical parameter in response to a surrounding condition, and accumulatively storing the generated electrical energy in at least one energy storing device that is coupled to the at least one accumulation mode sensor;

periodically comparing the stored electrical energy to a pre-defined threshold; and entering the electronic system in an deep sleep mode when the stored electrical energy is less than the pre-defined threshold; otherwise generating a wake-up event to trigger the electronic system to wirelessly transmit the physical parameter associated with the stored electrical energy to a receiver and to discharge the stored electrical energy in the energy storing device, and then to return to the deep sleep mode.

In one embodiment, when the stored electrical energy is equal to or greater than the pre-defined threshold, the electronic system is in a shallow-sleep mode in which all electronic components in the electronic system, except for an analog-to-digital convertor (ADC) and a timer, wait in a halt status.

In one embodiment, the method further comprises the steps of evaluating from the ADC a ready interrupt condition, thereby waking a controller to read a value, $V_{SC}$, of the ADC and compare $V_{SC}$ to the pre-defined threshold $V_{REF}$ and for $V_{SC} \geq V_{REF}$ send the physical parameter to the receiver, reset the at least accumulation mode sensor by discharging the at least one energy storing device, trigger the shallow sleep mode and provide a shallow sleep sampling interval; for $V_{SC} < V_{REF}$ enter in the deep sleep mode in which only a low power comparator is energized with a deep sleep sampling interval that is greater than a shallow sleep sampling interval.

In one embodiment, the method also includes the step of providing an instantaneous monitoring mode in which sensor output is continuously and instantaneously communicated to the receiver for short-term monitoring.

In one embodiment, the short-term monitoring is manually triggered by a user or is automatically triggered by a measured physical parameter that is greater than or equal to a user-selected reference level physical parameter.

In one embodiment, the electronic system is a dosimeter for monitoring exposure dose indoors, a dosimeter for adaptively monitoring exposure dose both outdoors and indoors, or a multichannel dosimeter for simultaneously monitoring exposure dose in different wavelength regions of electromagnetic radiation.

In one embodiment, the electronic system is attached on a skin surface or incorporated into an article of clothing or an accessory worn on a body.

In one embodiment, the method also includes the step of alerting a user wearing the electronic system as to exceeding a safe physical parameter exposure.

In one embodiment, the user wears a plurality of electronic systems over specific distinct skin locations.

In one embodiment, the method also includes the step of providing a user-characteristic to the receiver, wherein the user-characteristic is used to automatically determine the pre-defined threshold $V_{REF}$ tailored to the user.

Certain aspects of the invention also provide systems and methods for long-term monitoring of a physical parameter with a miniaturized electronic system configured to have low power requirements. In this manner, a miniature battery is sufficient to provide all the power needs, so that the system can monitor the physical parameter for a device lifetime that can exceed one year or more. Such long-lived sensors mean the systems need not have power source intervention, such as battery re-charging or replacement. The ability to provide a truly automated electronic monitoring system that can be worn on or connected to the body with fully wireless communication to a receiver, such as a hand-held portable device, is an important and fundamental contribution. Any need for user intervention, control, or readout is avoided in a safe, unobtrusive and reliable manner.

The systems and methods provided herein have a range of capabilities as they are compatible with a range of sensor platforms, depending on the to-be-measured physical parameter. One relevant parameter is radiation exposure, including exposure to unhealthy ultraviolet (UV) radiation, which adversely impacts skin health. UV sensors are known in the art. See, e.g., "Wireless, battery-free, flexible, miniaturized dosimeters monitor exposure to solar radiation and to light for phototherapy." Heo et al. Sci. Transl. Med. 10(470), eaau1643 (Dec. 5, 2018), which is incorporated herein by reference in its entirety. That system, while providing wireless dosimetry monitoring at multiple wavelengths, describes a battery-free, near-field communication (NFC) system with a continuous accumulation mechanism for measurement. Those systems, however, suffer from a limitation in that the NFC configuration require users to take action by scanning a smartphone to actively collect data and reset the sensor. That can be a fundamental limitation, particularly for uninvolved or forgetful users, where the lack of scanning can lead to low frequency data collection and attendant low quality data. The systems, devices and methods provided herein address this problem by providing an accumulation mode blue-tooth low energy dosimeter platform with a multi-year lifespan and fully automated data collection and reset capability. This reduces user burden while ensuring dense and accurate measurements.

Provided herein are systems and methods that provide automated and reliable monitoring of a physical parameter, thereby reducing user burden on managing the monitoring. This is achieved by providing a self-contained system that is powered by an on-board power source, such as a miniature battery, and a communication module that does not require user action, including by scanning of a hand-held device, including a smart-phone. Specially configured electronic components significantly reduce power requirements, so that the on-board power source can power the associated processors, chips and communications module over a time course of a year or more.

Conventional systems, in contrast, can suffer from being either semi-quantitative paper-based or photosensitive dye-based. Commercially available radiometers are highly expensive and not practical for consumer use. The unique ultra-low power cumulative sensing allows for extended battery life even with small, low profile batteries. The ultra-low power Blue-tooth operation scheme coupled with a self-powered, "accumulation" mode sensing platform allows it to function for a single, extended period of time before disposal. The systems provided herein are particularly useful as the next step for UV dosimetry applications.

The benefits are achieved in part by sensors and associated electrical and electronic components that are described herein as "accumulation" mode sensors or self-powered transducers. These sensors utilize self-powered transducers that provide an electrical output that is proportional to the magnitude of the physical parameter being sensed. A capacitor, also referred herein as a "supercapacitor", is used to "store" the current generated by the sensor. In this manner, the sensor need not be read out in a continuous mode, but instead the potential across the capacitor may be monitored in a periodic fashion, thereby reducing power requirements. Use of an onboard battery facilitates use of BLE communication module that avoids the need for scanning with a smartphone as required for battery-free systems with NFC communications.

Provided herein are electronic systems for long-term monitoring of a physical parameter. The system, in a basic configuration, comprises: an accumulation mode sensor (e.g., a self-powered transducer operating in an accumulation mode) for sensing the physical parameter; a wireless communication module electronically connected to the sensor; a power source electronically connected to the wireless communication system and/or the sensor to power the wireless communication system and/or the sensor; wherein the system has a sleep mode to provide the long-term monitoring. Long-term monitoring may refer to monitoring that occurs for at least 3 months or more, such as greater than one year, without power source replacement or re-charge.

The sleep mode may comprise at least two states, such as a deep sleep mode and a shallow sleep mode. An automated sleep mode scheme reduces user burden and improves power source longevity and corresponding electronic system lifetime.

The wireless communication module may comprise a Bluetooth module, such as a BLE chip.

Any of the systems herein may be characterized as wearable, including configured to be worn by a person and/or affixed to a skin surface. This is a reflection, in part, of the presented form factors and ability to fully encapsulate the system to provide waterproof characteristics and platform to mount directly to a skin surface or to be incorporated in clothing, jewelry, or other accessory associated with a user in a low-obtrusive manner.

Any the systems herein may further comprise a user-controllable power switch to switch the system to a power-off state, wherein the user-controllable power switch is a mechanical switch or a wirelessly-controllable power switch.

Any of the systems herein may have an instantaneous mode for real-time monitoring of the physical parameter in a manner that is non-accumulating and time-derivative physical parameter (e.g., intensity). Preferably, the real-time monitoring is for a relatively short duration so as to avoid undue drain on the battery.

The systems may be further described as having a deep and/or shallow sleep mode, thereby further improving system power characteristics and system lifetime. This is particularly beneficial for those systems that are completely encapsulated and where the power source is not configured for replacement. Instead, the power source is intended to provide sufficient power over the system lifetime, including for more than 6 months, more than one year, and more than two years.

The system is compatible with any number of electronic circuits that reliably and quickly switches between deep and shallow sleep modes. On example is an operational-amplifier (op-amp) comparator to switch to and from the sleep mode depending on a sensor output value compared to a reference voltage. For example, an output from the sensor generates a sensor voltage ($V_{SEN}$), wherein for a sensor voltage less than a reference voltage ($V_{REF}$) condition, the system is in the deep sleep mode; and for a sensor voltage greater than or equal to $V_{REF}$ condition, the system is in the shallow sleep mode. $V_{REF}$ can be any user-selected value, with the specific value selected depending on the circuit and sensor characteristics, the sensitivity of a user to the monitored physical parameter, and the application of interest.

The deep sleep mode may be characterized as having an average deep sleep current in the electronic system that is less than or equal to 5 µA, 8 µA, or 10 µA. The shallow sleep mode may be characterized as having an average shallow sleep current that, while being very low, is, on average, greater than the average deep sleep current, such as greater than 5 µA, 8 µA or 10 µA. The ratio of deep to shallow sleep mode currents may be greater than or equal to 5, greater than or equal to 10, or greater than or equal to 20. In this manner, the overall system current may be substantially reduced, thereby increasing device longevity or lifetime.

The system may be described as having a physical parameter sampling interval. For example, in the deep sleep mode the sampling interval ($T_{wake}$) is greater than or equal to 5 minutes; and in the shallow sleep mode $T_{wake}$ is less than or equal 30 seconds.

The shallow and deep sleep modes may provide an operating lifetime that is greater than or equal on 1 year without charging or replacement of the power source, including a power source that is non-rechargeable a battery.

Any of the systems provided herein have an output from the sensor that is characterized as a sensor voltage ($V_{SEN}$), such as a $V_{SEN}$ that is proportional to the magnitude of the physical parameter, and wherein for $V_{SEN}$ less than a reference voltage ($V_{REF}$) condition, the system is in the sleep mode, including a deep sleep mode.

The systems described herein are compatible with a range of sensors, depending on the application of interest. For example, the accumulation mode sensor may be one or more of: an optical sensor; an acoustic sensor; a mechanical sensor (such as one using a piezoelectric or a triboelectric sensor) a temperature sensor; a temperature gradient sensor; a humidity sensor; an air pollution sensor; a sweat or fluid sensor; and an electromagnetic energy sensor for selected wavelengths, including from radio wavelengths to gamma ray wavelengths.

The sensor may comprise a sensing unit that generates a current whose magnitude is based on a magnitude of the physical parameter and a capacitor that stores the generated current.

The sensor may comprise a photodiode, a piezoelectric crystal, thermoelectric device, and/or a triboelectric (contact electrification) device. The accumulation mode sensor may comprise a photodiode and a capacitor in electronic contact with the photodiode to monitor UV radiation. In this manner, the capacitor stores the current, and is periodically monitored and discharged, thereby providing the accumulation mode sensing.

Any of the systems may be used to monitor exposure to a selected range of the electromagnetic spectrum. For example, the system may monitor exposure to UV radiation, such as UVA and/or UVB, and at least one additional physical parameter.

The system may further comprise an on board actuator to alert a user to a risk condition, wherein the actuator is one or more of: a mechanical vibrator, an electric stimulator, or an optical light source.

Any of the systems provided herein may have a wireless communication module to automatically and periodically transmit a measured dose of the physical parameter to a remote reader without an active user intervention. The period between automatic transmissions may be dependent on the magnitude of the physical parameter, such that for larger magnitudes, the period is shorter, and for smaller magnitudes, the period is relatively longer.

The system may further comprise a receiver that collects and stores the transmitted data. The receiver may be an electronic hand-held device, such as a smart phone, laptop or tablet, or a fixed receiver such as a beacon positioned in a potential high physical parameter region. The receiver may be in two-way communication with the system, wherein a user input may, in turn, be used to govern system behavior, including $V_{REF}$, and frequency of monitoring.

The potential high physical parameter region may be a field of agriculture, a museum, a beach, an outdoor venue, a sporting competition, adjacent to an industrial plant, energy plant, an agricultural grow region, UV water purification, UV sterilization, a sauna, a spa, a workout facility, a gymnasium, a gameroom, a hospital, or a rehabilitation facility. Basically, wherever a long term monitoring capability is desired, the systems and methods described herein are compatible.

The systems provided herein may be described in terms of a form-factor, including having an effective diameter less than 2.5 cm and a thickness less than 1 cm.

The system may further comprise one or more encapsulation layers to completely encapsulate the sensor, module and power source to thereby waterproof the system.

The materials, physical dimensions and mechanical properties of the encapsulation layer, are selected in some embodiments to provide complete or partial electronic, optical, chemical and/or thermal isolation of the device from the surrounding environment during use during use. For example, the encapsulation layer may limit net leakage current, heat transfer, physical forces such as pressure and force, chemicals such as air pollution, thereby improving system longevity and accuracy. For example, the encapsulation layer may provide total isolation from the relevant parameter, or may be quantifiably define in terms of a conductivity or insulative barrier, such as thermal conductivity less than or equal to 0.3 W/m K, or leakage current less than 0.1 μA/cm².

The system may have a multi-year lifetime without external power or recharge of the power source.

The system may comprise a plurality of the systems configured to be worn on or connected to skin of a user at plurality of distinct skin locations. Multiple sensors at different locations may be in communication with a single receiver. In addition, the plurality of systems may be deployed in a field of agriculture, a museum, a beach, an outdoor venue, a sporting competition, adjacent to an industrial plant, energy plant, an agricultural grow region, UV water purification, UV sterilization, a sauna, a spa, a workout facility, a gymnasium, a gameroom, a hospital, or a rehabilitation facility.

Any of the systems may further comprise an additional sensor that is an instantaneous and/or continuous sensor to measure an additional physical parameter.

The remote receiver is configured to receive an input of a user characteristic to dynamically vary a reference level that controls a switch between deep sleep and shallow sleep mode. The user characteristic may be one or more of skin type, sun protection parameter (sunscreen, shade, clothing), age of user, ingestion of a sensitizing agent, and user sensitivity. For example, many pharmaceuticals have a side-effect of increased sensitivity to sunlight and corresponding increased sunburn risk. For those individuals, it is advisable to adjust $V_{REF}$ to obtain increased sensitivity for relatively lower UV exposure than individuals that are not similarly susceptible.

Any of the systems herein may be incorporated into a piece of jewelry, an accessory, a shoe, a watch, a piece of clothing, and/or to be worn underneath a piece of clothing.

An alert may be communicated from the system to a remote electronic device such as a hand-held cell phone or tablet, such as a warning of the physical parameter level.

Also provided herein are methods of monitoring a physical parameter using any of the systems provided herein. For example, the method may comprise the steps of: continuously measuring a physical parameter with a sensor that is a self-powered transducer; continuously providing an electrical output of the sensor to a capacitor, wherein the capacitor accumulates and stores the electrical output of the sensor; engaging a computer processor to automatically compare an electric potential across the capacitor ($V_{SC}$) with a reference voltage ($V_{REF}$) and: entering an ultra-low power deep sleep mode for $V_{SC} < V_{REF}$, and for $V_{SC} \geq V_{REF}$, a data package is communicated to a receiver and the capacitor discharged. The system periodically compares $V_{SC}$ to $V_{REF}$ and the communicating of the data package and discharging of the capacitor repeated until $V_{SC} < V_{REF}$ and the ultra-low power deep sleep mode is entered.

For $V_{SC} \geq V_{REF}$ the electronic system may be characterized as being in a shallow-sleep mode, where all electronic components in the system, except for an analog-to-digital (ADC) component and a timer, wait in a halt status. In this manner, even when the system is on, there is a relatively modest power requirement. The method may further comprise the steps of: evaluating from the ADC a ready interrupt condition, thereby waking the CPU to read the ADC value and compare $V_{SC}$ to $V_{Ref}$. For $V_{SC} \geq V_{Ref}$, the system sends the data package to the receiver, resets the sensor by discharging the supercapacitor, triggers the shallow sleep mode and provides a shallow sleep sampling interval; for $V_{SEN} < V_{Ref}$ entering into the deep sleep mode wherein only a low power comparator is energized with a deep sleep sampling interval that is greater than a shallow sleep sampling interval. For example, the deep sleep sampling interval can range on the order of minutes, such as between 1 minute and 30 minutes, and any subranges thereof. In contrast, the shallow sleep mode may sample on the order of seconds to minutes, such as between one second and 5 minutes. The sampling rate may be dynamically controlled, such that the rate changes depending on operating parameters, including the geographic location of the system, time of day, magnitude of the physical parameter being measured and/or a user characteristic.

Any of the electronic systems may comprise a UV sensor with a photodiode.

Any of the systems and methods may further comprise providing an instantaneous monitoring mode where sensor output is continuously and instantaneously communicated to the receiver for short-term monitoring. The short-term monitoring may be manually triggered by a user or may be automatically triggered by a measured physical parameter that is greater than or equal to a user-selected reference level physical parameter.

The electronic system may be mounted on a skin surface or incorporated into an article of clothing or an accessory worn by an individual, such as a watch, jewelry, a shoe, a piece of clothing or the like, and/or to be worn underneath a piece of clothing The electronic system may be reliably powered by a small battery for a long period of time. For example, the power source may be primary battery having a volume less than 0.5 cm³, while still providing sufficient power over a system lifetime that is greater than or equal to two years.

The method may further comprise the step of a user wearing the electronic system and providing an automated warning as to exceeding a safe physical parameter exposure. The warning may be directed to the user, or to an individual having interest in the user's wellbeing, such as a family member, medical caregiver, or a person having responsibility over the safety and well-being of the user, such as an employer (in commercial applications) or commander (for military applications).

A user may wear a plurality of electronic systems over specific distinct skin locations. For example, to provide an automated warning such as a time to burn on different skin locations for systems that monitor UV exposure.

The method may further comprise the step of: providing a user-characteristic to the receiver, wherein the user-characteristic is used to automatically determine a $V_{REF}$ tailored to the user and/or application of interest. Exemplary user-characteristics include one or more of skin type, sun protection parameter (sunscreen, shade, and clothing), age of user, ingestion of a sensitizing agent, and user sensitivity, wherein the sensor is a UV sensor.

Examples of electronic systems for monitoring a physical parameter further include those having an accumulation mode sensor for sensing the physical parameter, wherein the sensor generates electrical current based on a magnitude of the physical parameter and the generated electrical current is stored in a capacitor electronically connected to the sensor. A wireless communication module is electronically connected to the sensor. A power source is electronically connected to the wireless communication system and/or the sensor to power the wireless communication system and/or the sensor. A receiver in wireless communication with the wireless communication module is configured to receive data packet transmission for the wireless communication and/or input from the sensor, including so as to adjust $V_{REF}$ (two-way communication); a processor is incorporated into the electronic system, wherein the processor is configured to cause the electronic system to at least perform operations comprising: periodically sampling an electric potential across the supercapacitor ($V_{SC}$) and wirelessly transmitting data to a receiver; comparing $V_{SC}$ to a reference voltage ($V_{REF}$) such that: for $V_{SC} < V_{REF}$ causing the system to enter into a power-conserving mode wherein sampling frequency is reduced and the system is powered down except for the comparing of $V_{SC}$ to $V_{REF}$ to provide for continuous ultra-low power operation; for $V_{SC} \geq V_{REF}$ causing the system to enter into an active mode that discharges the supercapacitor to reset the accumulation mode sensor and wirelessly transmit data from the wireless communication module to the receiver.

The processor may be further described as having a component, or controlling a component, to compare $V_{SC}$ to a reference voltage ($V_{REF}$) to provide a deep sleep mode and a shallow sleep mode by triggering an ADC sampling to compare $V_{SC}$ to $V_{REF}$ in the shallow sleep mode where the ADC sampler and a processer timer are energized and for the ADC sampler reporting a ready interrupt state, the processer is energized to compare $V_{SC}$ to $V_{REF}$ and for $V_{SC} \geq V_{REF}$ a communication packet is sent to the receiver and $V_{SC}$ discharged, wherein the triggering is periodically repeated at a shallow sleep state frequency, including a frequency between about 1 second to 1 minute; for $V_{SC} < V_{REF}$ the system enters a deep sleep mode, wherein an average current in the shallow sleep mode is at least two times greater than an average current in the deep sleep mode. In the deep sleep mode, the sampling period may be further reduced. The processor may also receive active commands from a user to switch-off (e.g., power down), enter a deep sleep mode, a shallow sleep mode, or an active wake mode, where data is more frequently sent to a reader, and discharge of the capacitor may be more frequent, or bypassed in favor a continuous and relatively instantaneous ongoing read-out.

Any of the systems provided herein may, in a general configuration, be described as comprising: an accumulation mode sensor for sensing a physical parameter; a wireless communication module electronically connected to the sensor; and a power source electronically connected to the wireless communication system and/or the sensor to power the wireless communication system and/or the sensor. This configuration provide various functional benefits, including one or more of: operation for 3 months or more without power source replacement or re-charge; a power consumption that is at least 25% lower than that of a comparable system that incorporates a sensor that does not offer the accumulation mode of operation; and/or an accuracy in dosimetry that is at least 25% better than that of a comparable system that incorporates a sensor that does not offer the accumulation mode of operation. "Comparable system" refers to an equivalent system but without a capacitor that stores electrical output from the sensor and that facilitates the accumulation mode sensing.

It should be noted that all or a part of the methods according to the embodiments of the invention is implemented by hardware or a program instructing relevant hardware.

Yet another aspect of the invention provides a non-transitory computer readable storage medium/memory which stores computer executable instructions or program codes. The computer executable instructions or program codes enable a computer or a similar computing apparatus to complete various operations in the above disclosed methods of measuring physical parameters. The storage medium/memory may include, but is not limited to, high-speed random access medium/memory such as DRAM, SRAM, DDR RAM or other random access solid state memory devices, and non-volatile memory such as one or more magnetic disk storage devices, optical disk storage devices, flash memory devices, or other non-volatile solid state storage devices.

These and other aspects of the present invention are further described below. Without intent to limit the scope of the invention, examples according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Ultra-Low Power, Miniaturized Electronics with Wireless Communication Capabilities UV wearables are designed to monitor personalized exposure to UV outdoors and modulate sunburn risks. Despite recent rise of wearables such as fitness bands in the consumer market, the adoption of UV wearables among the general consumers is low. Typical barriers to adoption applicable to conventional UV dosimeters include limited battery life ranging from lifespan of 6 days to 6 weeks, bulky form factor, and moderate to low water protection. Those UV wearables operate in an 'instantaneous mode' and intermittently measure intensity of exposure at a selected frequency.

Integration of intensities over exposure time yields exposure dosage, a critical variable of interest for predicting sunburns. We have previously demonstrated a battery-free, miniaturized wireless UV dosimeter (mm-NFC), including as described in "Wireless, Battery-Free, Flexible, Miniaturized Dosimeters Monitor Exposure to Solar Radiation and to Light for Phototherapy", Heo et al., *Sci. Transl. Med.* 10(470), eaau1643, (Dec. 5, 2018), and "Alternative Approach for UV Sensing", Rogers et al., PCT Publication No. WO2016196673, (Dec. 8, 2016), which are incorporated herein by reference in their entireties. That NFC-based, battery free sensor required user intervention to scan and read the device to obtain accurate measurements and reset the devices.

Certain aspects of the invention as shown in this exemplary example present fundamental improvements and a new sensor based, in part, on that previous technology. Specifically, we implement a small onboard battery with a BLE functionality. The electronic systems provided herein are able to operate in an ultra-low power mode enabling long term operation (months to years). In addition, the system allows for periodic transmission of UV dose and an automatic reset without the need for user intervention. The transmission frequency can be adaptable for higher frequency sampling during high UV scenarios (e.g., vacation in a location close to the Equator) or lower frequency sampling during low-UV scenarios (e.g., during winter or when inside a closed building). The data can be sent to any mobile device to trigger alerts when certain thresholds of UV is sensed to the user in case of impending sunburn.

Such accumulation mode BLE UV dosimeter with multiyear lifespan removes user burden by elimination of battery recharging needs and automation of data collection. To allow use during heavy sweating or water immersive scenarios, an encapsulation layer, such as PDMS (polydimethylsiloxane), hermetically seals the entire system including the battery. General consumer adoption of UV wearables for use during outdoor or aquatic activities to accurately monitor personalized exposure can prevent excessive UV exposure and sunburn, thereby reducing the incidence of skin cancer.

Accordingly, provided herein is an electronic system that is an ultra-low power, cumulative mode sensing for miniaturized, fully encapsulated electronics with Bluetooth communication.

Operation is compatible with ultra-austere environments: underwater, boiling hot water (e.g., thermal springs), space, or within the human body (e.g., in stomach acid).

Anatomically specific UV sensing: skin cancer have anatomical predilections. For instance, melanoma is most commonly found on the upper backs of men and the posterior aspects of women—with the prevailing hypothesis that intermittent high UV exposure is particularly carcinogenic. The face, specifically, the nose is an area of high frequency for non-melanocytic skin cancers. Thus, the ability for miniaturized UV dosimeters to be placed in anatomically specific locations allows for a more stratified assessment of UV exposure.

Other applications include UV sensing for consumer health, beauty and skin aging. The systems provided herein can also sense UV in aquatic scenarios/water sports, for clinical medicine, for sunburn prevention, skin cancer prevention.

The systems provided herein are useful for UV sensing for phototherapy optimization (e.g., narrow band UV phototherapy optimization for psoriasis), for photosensitivity related to medications, connective tissue disease (e.g., systemic lupus erythematosus), and in the setting of dermatological conditions that increase photosensitivity (e.g., oculocutaneous albinism).

The cumulative configuration provided herein has a number of applications, including physical activity sensing for physical activity monitoring, sensing for sleep restlessness, sensing for air pollution, sensing for ionizing radiation, sensing for thermal flux, and sensing for visible light for agriculture. The sensors can be used to optimize LED illumination of plants in hydroponics. This can create feedback loops where low light sensing can lead to brighter power being driven to LEDs or lowering of the LED lights closer to the plant source. This can be useful in grow applications where LED lights are used to supplement natural light, such as in greenhouses.

Any of the systems provided herein may use multimodal sensing between UV and any of the above measurement modalities. These combination systems may utilize the cumulative sensing modality or an active sensing component or vice versa (e.g., UV is collected in an ultra low power cumulative mode, but physical activity is sensed with traditional modalities).

Accelerometer—for the purposes of assessing physical activity. Physical activity is almost universally beneficial to health except in the context of UV exposure, which increases the risk of skin cancer. Thus, the ability to sense physical activity and UV is of benefit for professional, amateur and recreational athletes.

Thermal flux—ability to assess thermoregulatory and heat dissipation function of the skin as a method to assess risk of heat stroke.

Ambient temperature—for the purpose of assessing ambient heat index along with UV index.

Humidity sensor—for the purpose of assessing ambient heat index along with UV index.

Air pollution—for the purpose of assessing ambient conditions whereas air pollution and UV can both cause skin damage and photo-aging.

Sweat—for the purpose of assessing physical activity, physical workload and thermal load on the body concurrently with UV exposure and physical activity.

UV sensing in combination of other relevant sensors: ECG, EMG, pulse oximetry.

The electronic systems provided herein have a number of advantages including, a form factor that allows for a surface area profile of less than 2 cm; fully encapsulated with no ports, peripherals, mechanical discontinuities, or mechanical parts allow for complete encapsulation for water proofing, and robustness. The systems provide an important extension of previously reported accumulative UV sensing with a photodiode and supercapacitor, by including with Bluetooth® modality and an onboard battery. This avoids the need for scanning and resets by the user.

The systems also provide a convenient platform for including additional sensing functions with the onboard battery to include physical activity sensing concurrently with UV sensing.

Figure 2:
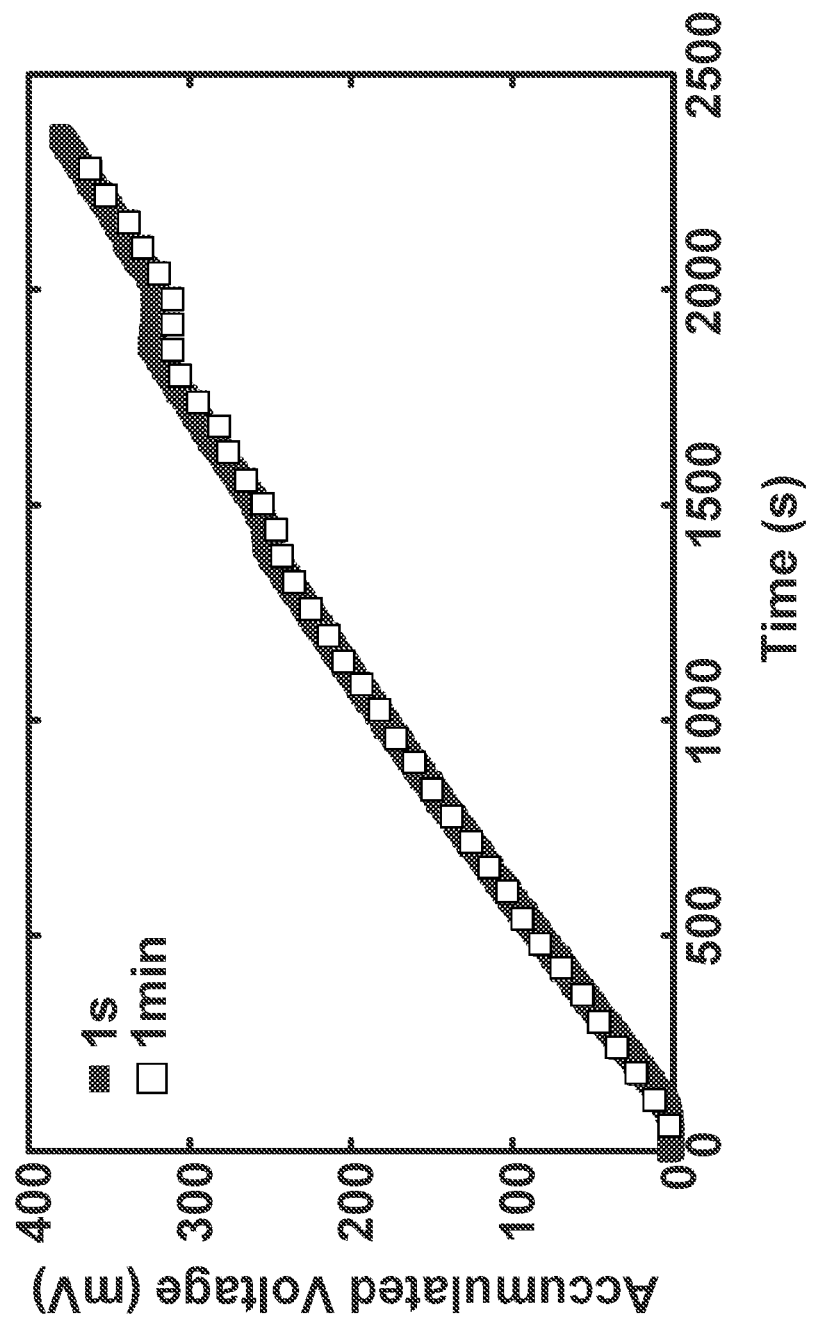
FIG. 2 shows accumulated voltage measurements ($V_{SC}$) for sampling period of 1 second and 1 minute for a UV sensor under a randomly simulated applied UV exposure profile over time.

Unlike conventional devices, our previously reported mm-NFC platform operates in an 'accumulation mode' and directly measures exposure dosage. The mm-NFC platform includes a fully passive sensing circuit and near field communication (NFC) protocol to enable continuous exposure dose monitoring without power. FIG. 1 shows the circuit schematic of the mm-NFC platform. A photodiode (PD) continuously generates photocurrent proportional to exposure intensity. The photocurrent accumulates in the supercapacitor (SC). The potential across the SC represents total exposure dose. This leads to direct measurements of total exposure dosage independent of sampling frequency. For 'instantaneous mode' dosimeters, the accuracy of indirect measurements of exposure dose degrades with low sampling rate of intensity (FIG. 2). Wireless activation of the MOSFET (MOS) drains the charge stored in SC and effectively resets the sensor. Due to increasing leakage of the SC at high potential (>200 mV), a reset is important for accurate measurement of total exposure dose.

The mm-NFC platform eliminated battery-recharging needs, miniaturized the system below the bulk of a coin cell battery, and achieved high level of water protection by hermetic encapsulation of the entire system with a UV transparent polymer. However, NFC devices require user scan action with a smartphone to actively collect/reset data. For uninvolved users, lack of scan actions may result in low density and low quality data.

In certain aspects of the invention, the systems provided herein are an 'accumulation mode' BLE dosimeter platform with a multiyear lifespan and automated data collection and reset to further reduce user burden while achieving frequent and accurate measurements during UV exposure.

Figure 3:
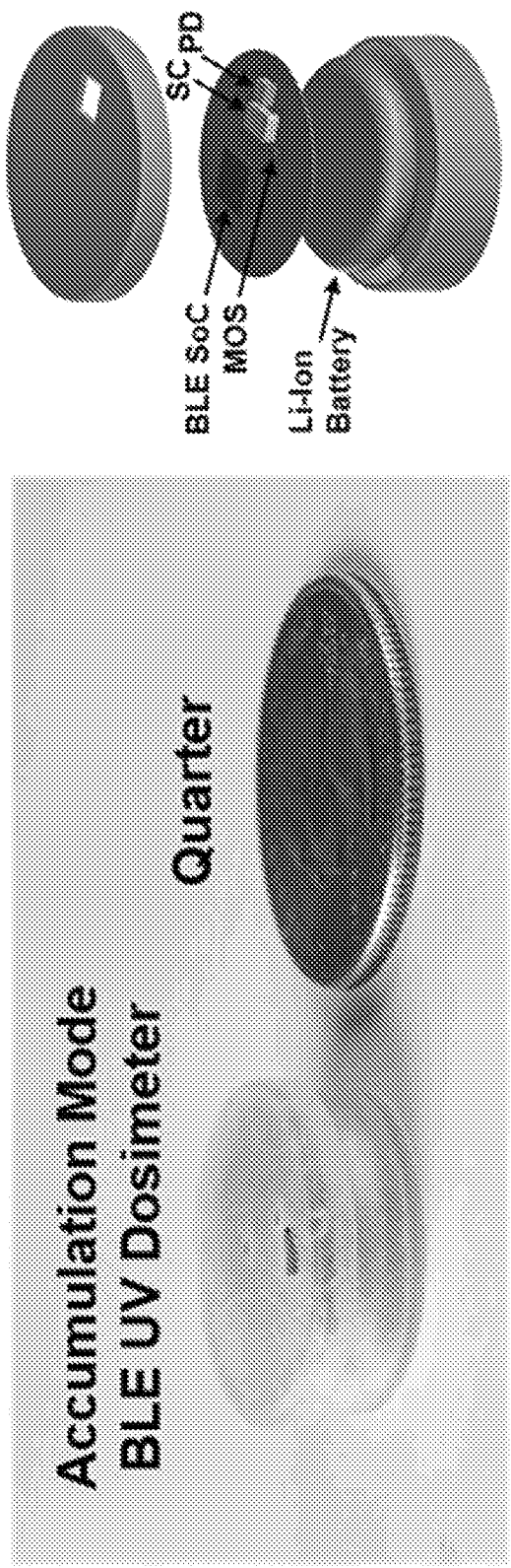
FIG. 3 shows pictures of an electronic system that is an 'accumulation mode' BLE dosimeter illustrating the size relative to a quarter and a schematic illustration of various components thereof, including encapsulation layer, power source, wireless communication module (BLE SoC), sensor, and related electronic circuitry, according to embodiments of the invention.
Figure 4:
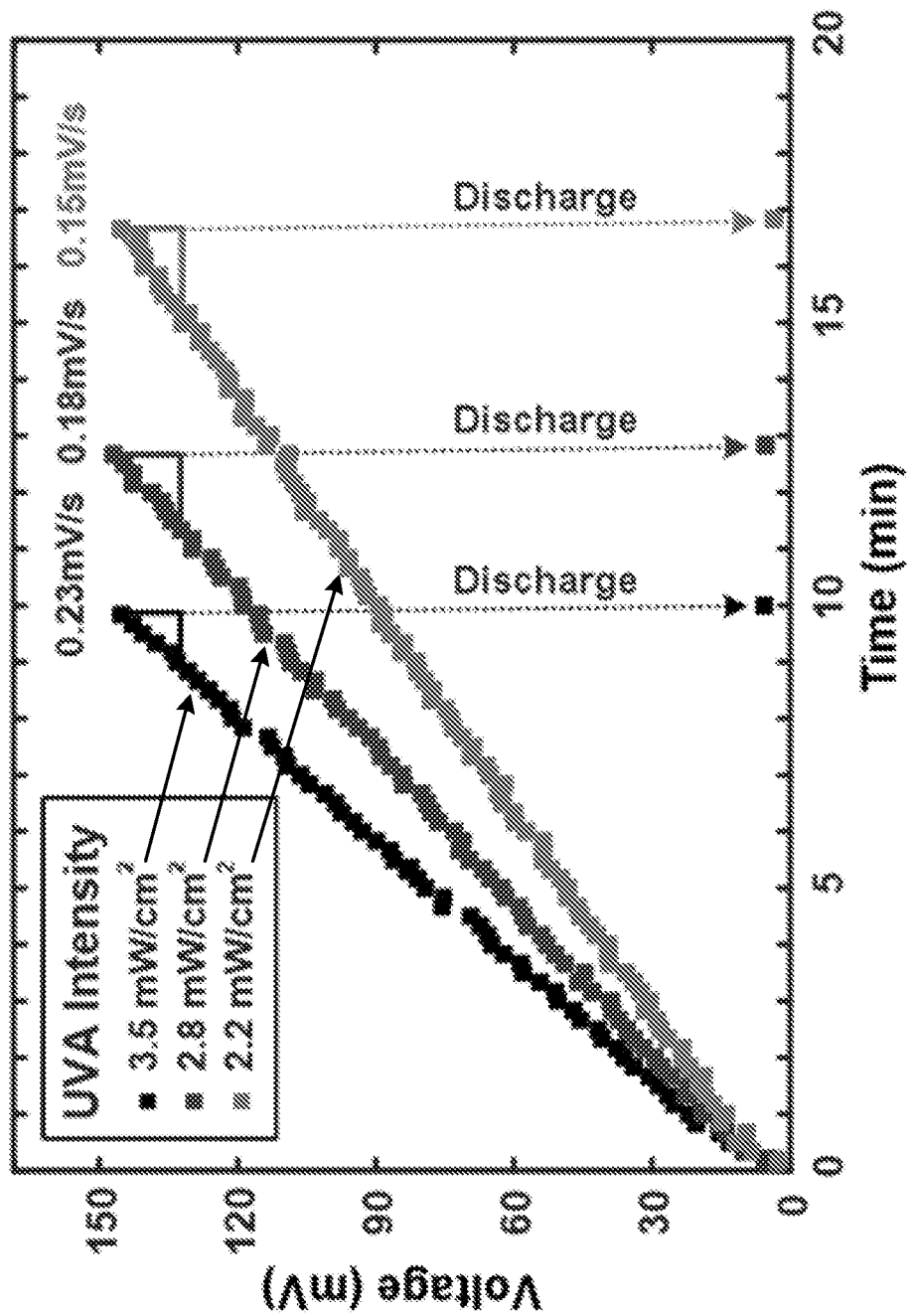
FIG. 4 shows voltage output as a function of exposure time for different UVA intensity of a battery-free dosimeter according to embodiments of the invention.

In some embodiments, as shown in FIG. 3, the 'accumulation mode' BLE UV dosimeter has dimensions, such as, the diameter and thickness of about 20.1 mm and about 5.8 mm, respectively. FIG. 4 shows voltage outputs of the dosimeter as a function of exposure time. UV lamp exposed the dosimeter with constant intensity at three different intensities, 2.2 mW/cm$^2$, 2.8 mW/cm$^2$, 3.5 mW/cm$^2$, corresponding to low to moderate UVA index conditions outdoors. As expected, the charging curve is linear and the slope, or the rate of SC charging, is proportional to the exposure intensity. The dosimeter is configured to automatically reset when the SC voltage rises above a preprogrammed reset voltage to ensure minimal SC leakage effects.

In some embodiments, the invented dosimeter comprises an 'accumulation mode' sensing circuit paired with an ultra-low power BLE operation scheme. A representative circuit diagram of the dosimeter 100 is shown in FIG. 5A. The only active component of the electronic system of the dosimeter 100 is the wireless communication module 110 (illustrated as a BLE system-on-chip) with minimized current consumption using a low-power sleep mode between measurements by the accumulation mode sensor 120. The invention takes advantage of the 'accumulation mode' detection and measures the UV dose at long time intervals (>10 minutes) to enable 2 plus years of operation from an on-board power source 130, e.g., a standard coin cell battery (CR1632) or equivalent thereto. Accordingly, some embodiments of the power source 130 may be described as a battery having a nominal voltage of 3 volts, typical capacity of 130 mAh, 2 grams or less weight, 0.5 or less cm$^3$, with a diameter less than or equal to 1.6 cm, and a thickness less than or equal to about 3.2 mm, while still providing multi-year lifetime operation.

Figure 6:
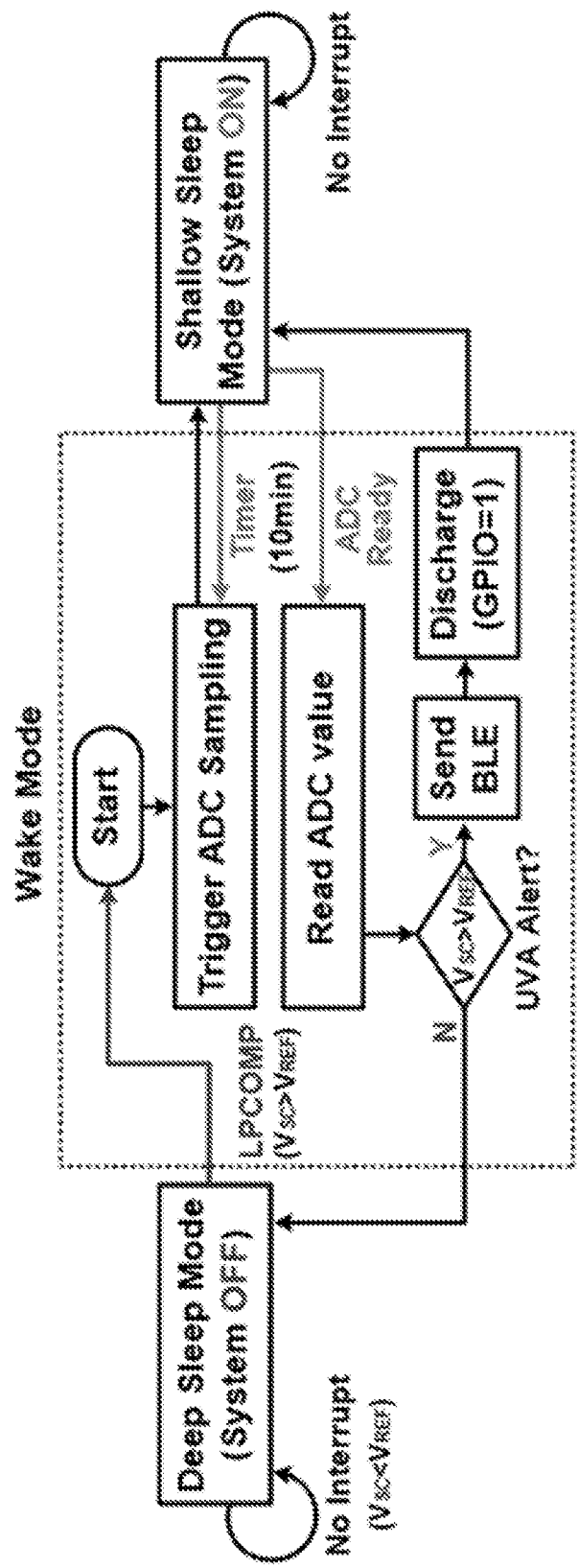
FIG. 6 shows a flowchart of an 'accumulation mode' BLE dosimeter having deep sleep, shallow sleep and wake modes, depending on sensor voltage output relative to reference voltage ($V_{ref}$), including for the dosimeter circuit of FIG. 5A, according to embodiments of the invention.

The flowchart of the system (e.g., the dosimeter 100 shown in FIG. 5A) utilizing two different sleep modes: system-on sleep (shallow sleep) and system-off sleep (deep sleep), is shown in FIG. 6 according to some embodiments of the invention. Referring to FIGS. 5 and 6, in operation, when BLE operation starts, the CPU triggers the ADC sampling and goes into the shallow sleep, which makes the entire BLE SoC, except the ADC and the Timer, wait in a halt status. When the ADC reports a ready interrupt, the CPU wakes up (e.g., activates), reads the ADC value and compares the SC voltage ($V_{SC}$) against a preprogrammed reference voltage ($V_{REF}$). At high UV conditions, $V_{SC} > V_{REF}$ (185 mV corresponding to exposure energy of 1.8 J/cm$^2$), the CPU alerts the user (e.g., Mobile Devices 190 of the user shown in FIG. 5A) by sending a BLE packet, discharges the SC and enters the shallow sleep again, which triggers the ADC sampling at a preprogrammed sampling interval (10 minutes). The average current consumption of the BLE SoC in the shallow sleep mode at different sampling rate is shown in Table 1. At low UV conditions, $V_{SC} < V_{REF}$, the CPU enables the low-power comparator (LPCOMP) to monitor $V_{SC}$ and goes into the deep sleep, which powers down the entire BLE SoC except the LPCOMP. The dosimeter system remains in the deep sleep in no UV conditions indoors or during nighttime. When $V_{SC}$ rises above $V_{REF}$, the CPU wakes up from the deep sleep and runs the program from the starting point. The average current consumption of BLE in the deep sleep mode is shown in Table 2. Constant exposure at a moderate UV intensity of 2 mW/cm$^2$ results in waking interval ($T_{WAKE}$) of 10 minutes with average current consumption of 4.5 μA and projected lifespan of 3+ years. For a minimal erythmal dose (MED) of 20 J/cm$^2$ relevant to Fitzpatrick skin type I, one alert is equivalent to 8.5% of MED; MED is reached after 11 alerts (11*1.8 J/cm$^2$).

TABLE 1

Shallow Sleep Mode

| $T_{WAKE}$(s) | $I_{AVG}$ (μA) | Life Span (year) |
|---|---|---|
| 1 | 22 | 0.7 |
| 4 | 14.1 | 1.1 |
| 8 | 12.7 | 1.2 |
| 16 | 11.2 | 1.3 |

TABLE 2

Deep Sleep Mode

| $T_{WAKE}$ (min) | $I_{AVG}$ (μA) | Life Span (year) |
|---|---|---|
| 20 | 3.2 | 4.6 |
| 15 | 3.6 | 4.1 |
| 10 | 4.5 | 3.3 |
| 5 | 6.9 | 2.1 |

According to the invention, among other things, the novelty of the UV sensing involves a self-powered current generating electronics unit (in this example, a UV photodiode (PD) run in reverse) coupled to a supercapacitor (SC) that holds charge continuously. This cumulative charge can then be translated back to the parameter of interest (in this example, UV irradiance) based on a calibration curve. An NFC or Bluetooth® unit can then sample the SC periodically and then also discharge the SC to allow for a reset. This functionality allows for continuous, ultra-low power operation with the system drawing significant current only when transmission and reading of the SC are required. This sensing modality can be translated to other self-powered sensing units that can generate current. Beyond a photodiode, piezoelectric crystals with deformation or physical activity can be used. Other sensors can be used to measure thermal flux and generate a current that is stored in the supercapacitor. Other sensors can be used to assess for ionizing radiation with wavelengths shorter than UVC (e.g., X-ray radiation, gamma radiation). Thus, this disclosure encompasses the ability to capture current continuously in a passive manner that is then transmitted to a mobile device or display unit at user prompting or at a set frequency to conserve power. Additional embodiments include the ability for the cumulative sensing mode to trigger an action—this action may be to transmit the data to a mobile device or activate a notification on the sensor itself (e.g., LED or vibrator). This can then allow the sensor to be fully passive and notify the user only when a critical threshold is reached. Thus, these sensors are "always-on" operating in a continuous mode with minimal current draw. Of course, the systems provided herein are compatible with an off-state, such as from a mobile device or switch in the circuit, to completely turn-off the systems, thereby providing maximum power savings.

Another key distinguishing feature is that these systems enable full, protective encapsulation with no ports, mechanically active parts, peripherals, or pegs allowing for significant protections against external damage such as water, heat, or humidity. Thus, these electronics are distinguished by having minimal to no mechanical discontinuities. This also requires no user maintenance (battery charging, cleaning, or preparation prior to use).

Further embodiments can include using UVA thresholds to trigger the activation, sensing, transmission of data from other sensing components (e.g., accelerometer, temperature, UVB, visible light). Similar thresholds can be used to trigger an onboard notification to the user on the sensor itself (e.g., a red LED turns on when a critical value of UV is reached) that is separate from any external device.

Further embodiments can enable mobile phone derived data (e.g., GPS, UV index, air pollution) to drive the sensor into a higher activity sampling in node instances where a user is in a geolocation that portends a high risk of sunburn (e.g., a high UV index location that is distinct from an individual's normal environment).

The underlying software of the Bluetooth® operation of the sensor system enables the deep sleep mode. The Bluetooth® layer is modified to broadcast the data (e.g., UVA/UVB dose) as part of the advertisement package instead of establishing a connection and communicating though characteristic notification in connection intervals.

Lower Power Consumption: Since the sensor's data transfer is based on the UVA/UVB exposure threshold, the data transfer interval is unpredictable. Depending on the location and time, the sensor might transfer the UVA/UVB data every 10 seconds or not at all for weeks. Establishing a connection requires a connection interval that is limited by manufacturers (about 4 s), resulting in additional radio events that consumes unnecessary power consumption. The current consumption is reduced from 4.5 µA to 0.56 µA when the data is transferred every 10 minutes.

Figure 12:
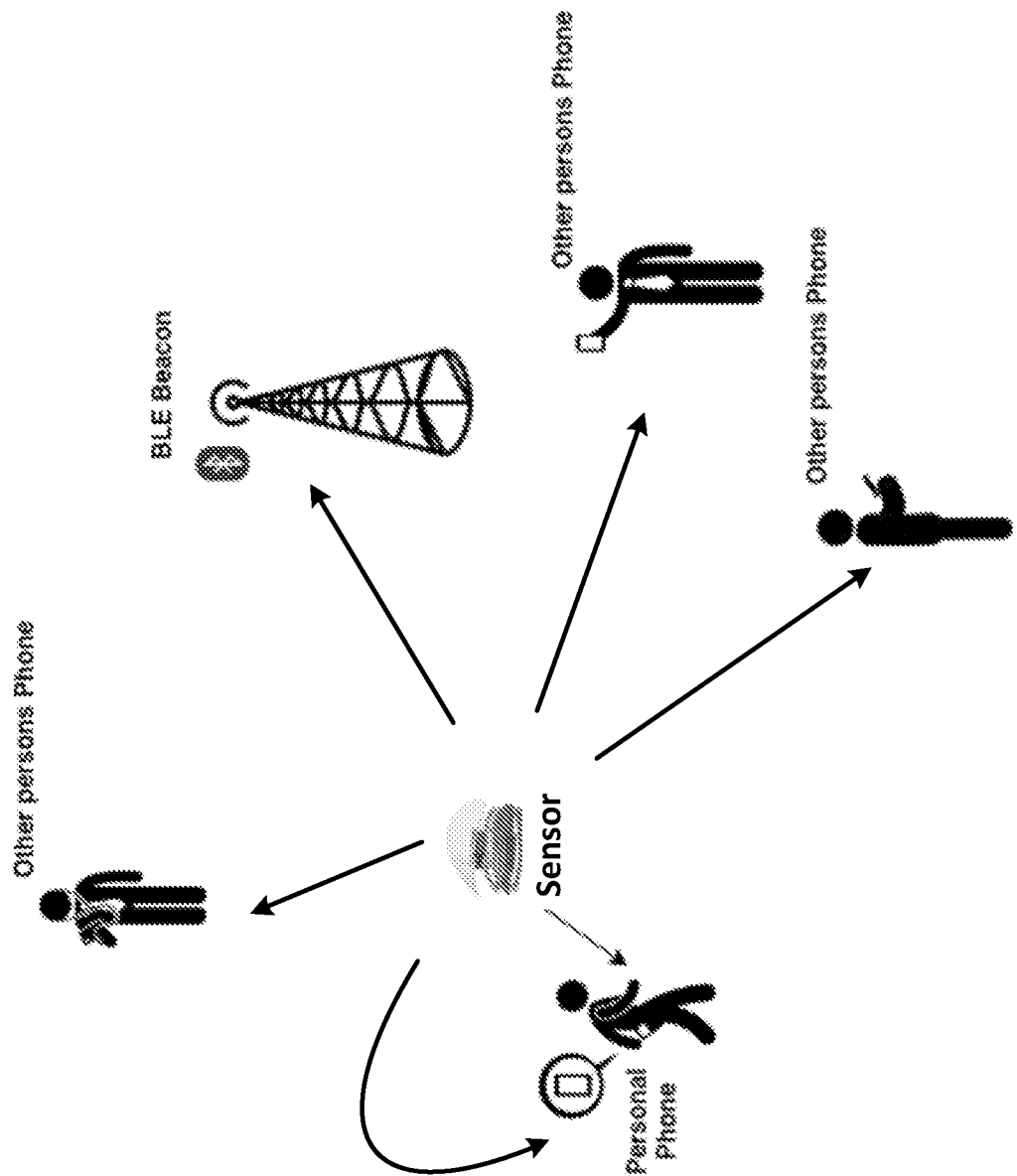
FIG. 12 illustrates the versatility of the wireless connection and ability to communicate relevant information to any of a variety of platforms, including the user's handheld, any of a multiple third-parties, or a BLE beacon, according to embodiments of the invention.
Figure 13A:
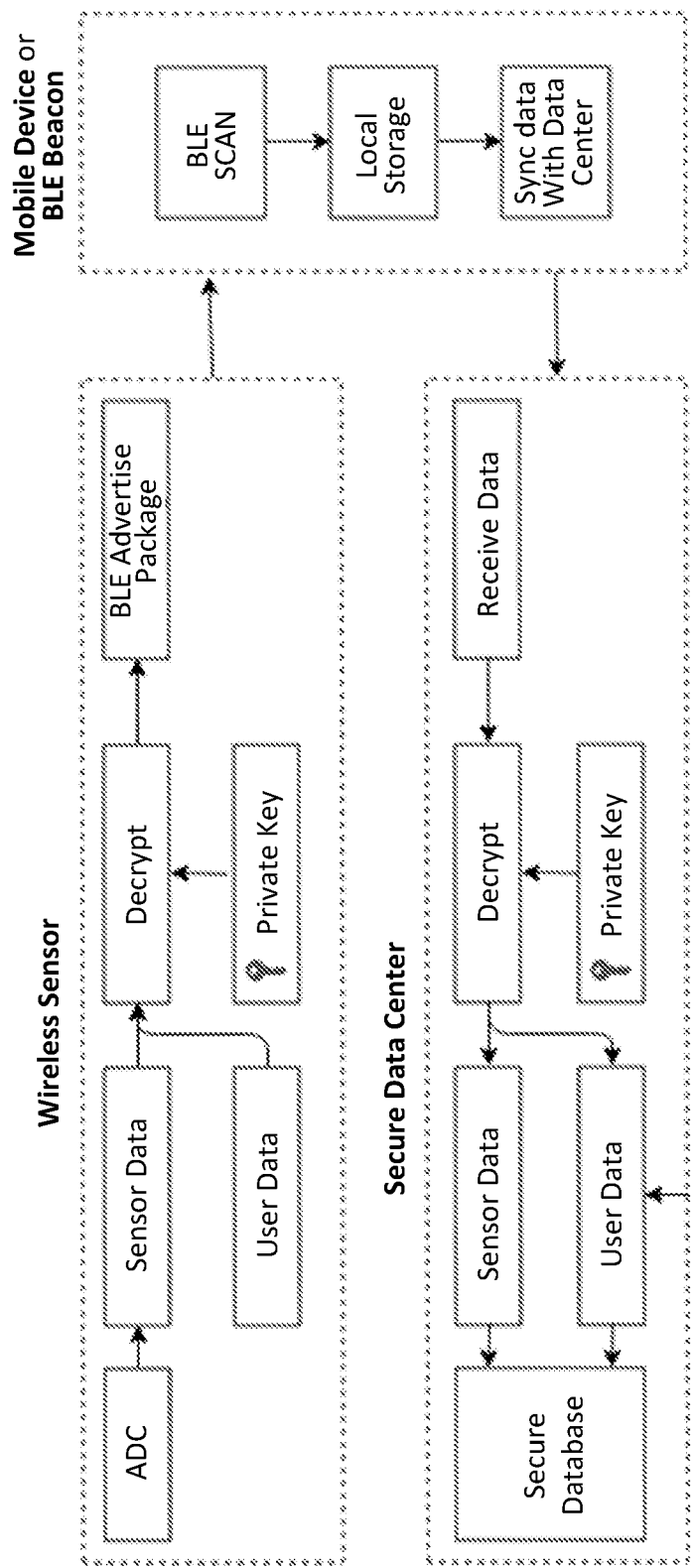
FIG. 13A is a flowchart schematic of the various components of the device, according to embodiments of the invention, including the wireless sensor portion, receiver (identified as "Mobile Device or BLE Beacon") and, depending on the application of interest, a secure data center.

Decentralized Sensor Network: Since there is no one to one relationship between the sensor and the handheld receiver/controller (e.g., phone), this allows any device that can scan for BLE advertisements to capture the data and transfer it to a central database. For example, a beacon may be located on beaches that collects the UV data from the sensors eliminating the need to carry a phone or have somebody else's phone collect your data that can later be synced to the cloud. Note that the data may be encrypted on the sensor side to ensure privacy. FIG. 12 illustrates the versatility of the wireless connection and ability to communicate relevant information to any of a variety of platforms, including the user's handheld, any of a multiple third-parties, or a BLE beacon. As shown in FIG. 13A, the sensor data of the wireless sensor (i.e., electronic system disclosed in the disclosure) and user data (e.g., user ID) are decrypted and transmitted to the receiver (identified as "Mobile Device or BLE Beacon") in the form of BLE advertise package. Once receiving the BLE advertise package, the receiver processes it and syncs the data with a data center and send it to the secure data center.

Figure 13B:
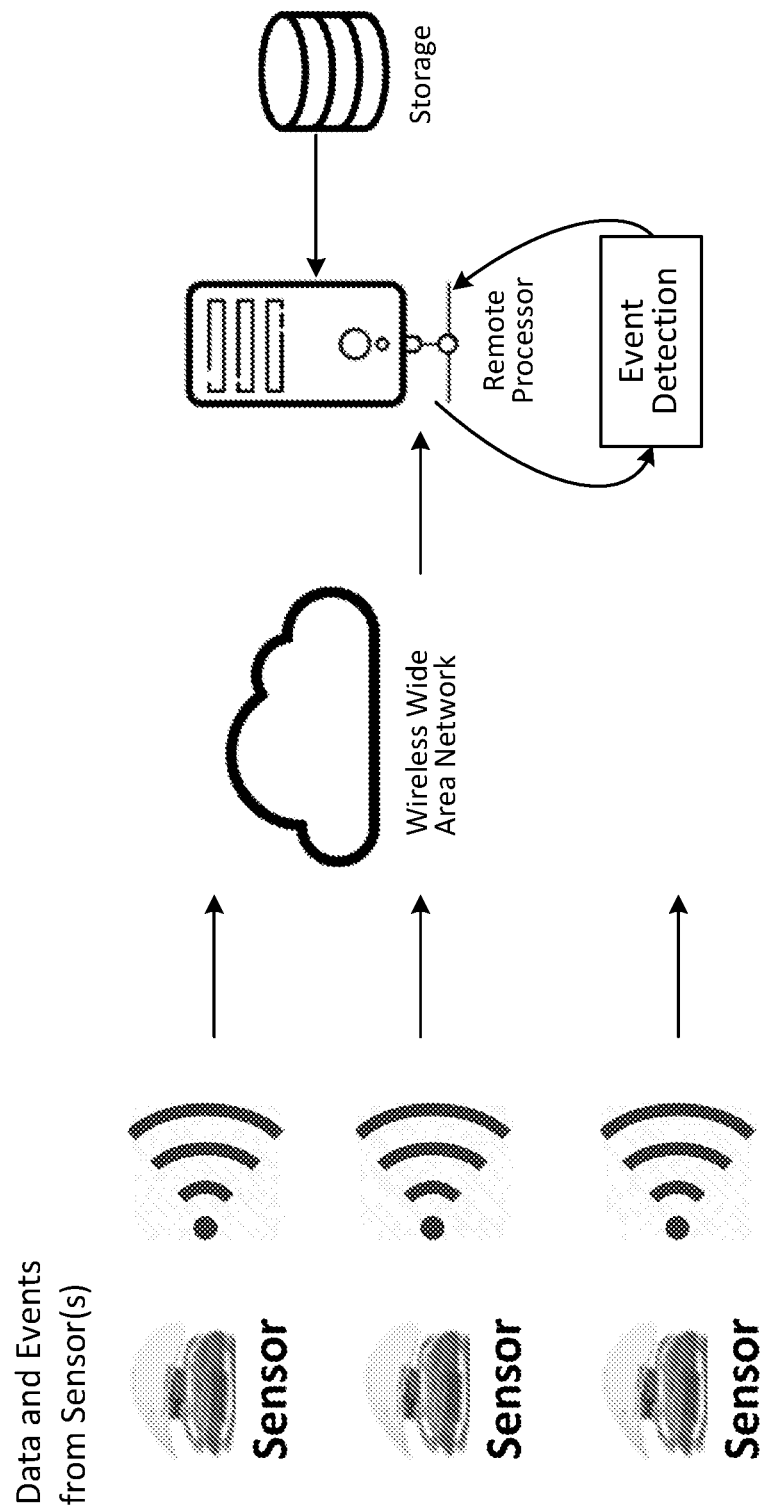
Figure 13B:
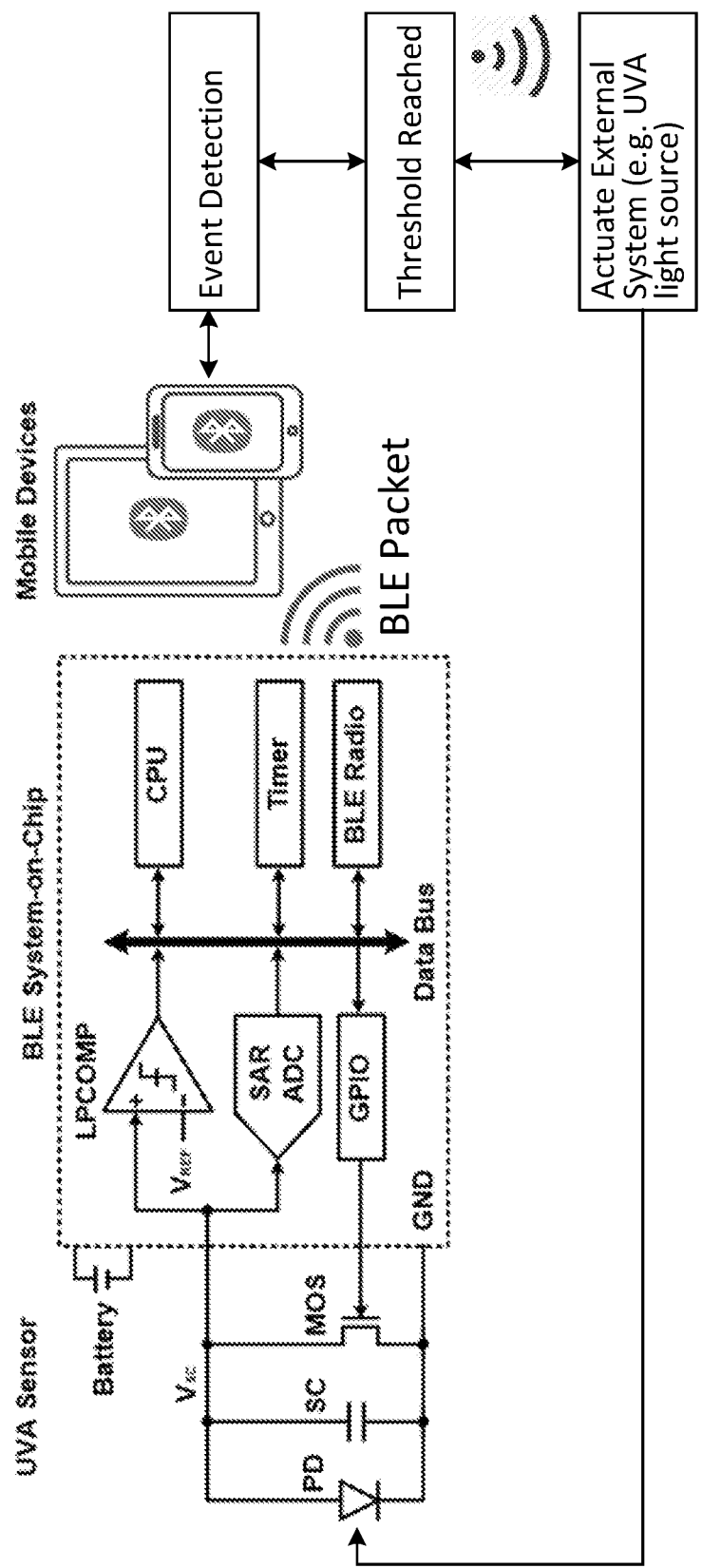

FIG. 13B describes how wireless communication protocols beyond BLE and NFC might work for a multiplex of sensors transmitting to an external remote processor via a cellular link. This leads to actuation of an external system (e.g. grow lights for agriculture) where it is brightened or darkened—leading to continued sensing by the sensors creating a closed feedback loop. In addition, it can also be used for UV sensing in areas of ozone degradation, and IR sensing in geographically isolated locations or thermally active locations, and so on.

Figure 13C:
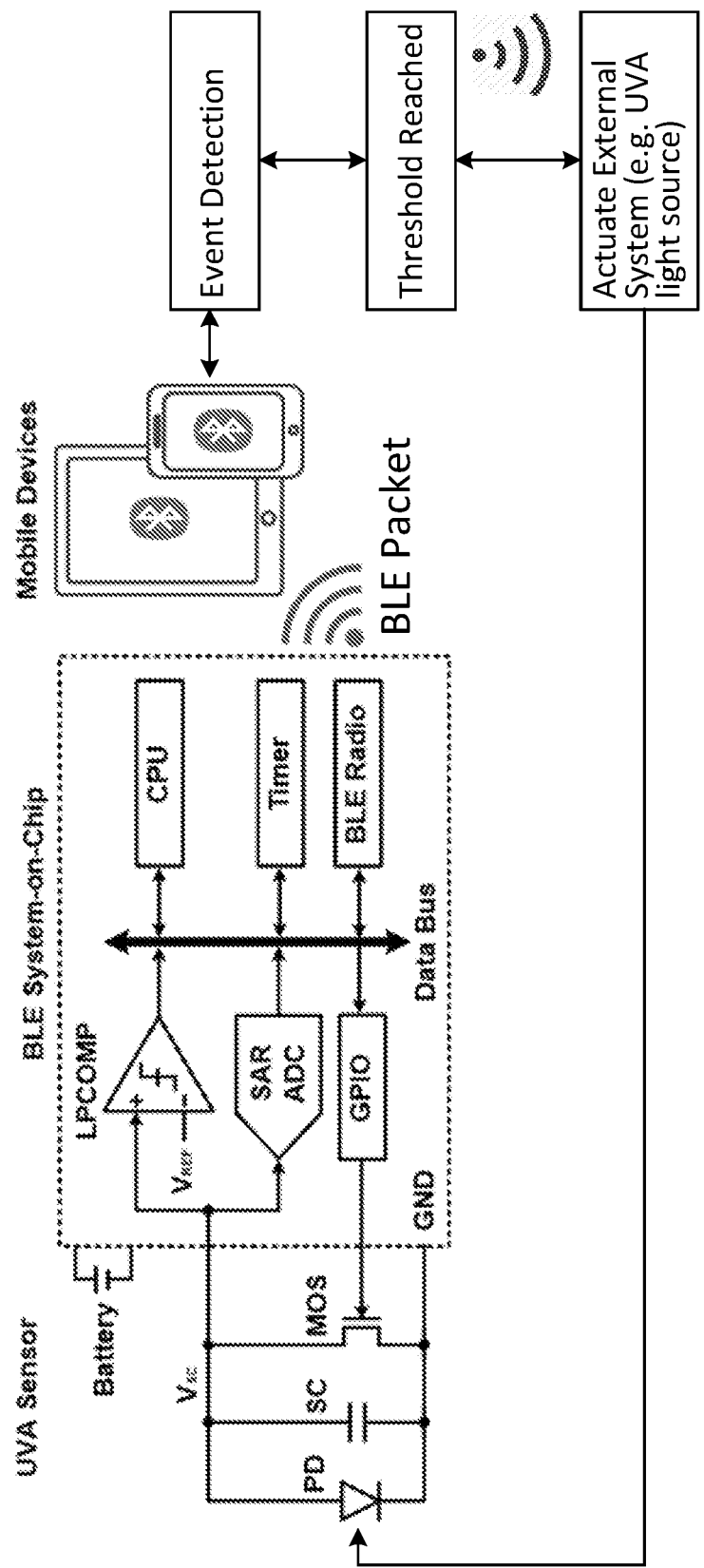
FIG. 13C shows an electronic system including a closed-feedback loop according to embodiments of the invention. A sensor communicates via Bluetooth to a base unit (does not necessarily need to be a mobile device) that then leads to event detection, thresholding and actuation of a separate external system. The actuation could mean a notification on a separate system, warning message, or change in light output. The sensor then continues to sense the parameter of interest (in this case UV).

Furthermore, this extends upon the agricultural application to more broadly include closed-feedback loop for the system. This can be accomplished vithe current BLE embodiment or the cellular communication embodiment, as shown in FIG. 13C. A sensor communicates via Bluetooth to a base unit (does not necessarily need to be a mobile device) that then leads to event detection, thresholding and actuation of a separate external system. The actuation could mean a notification on a separate system, warning message, or change in light output. The sensor then continues to sense the parameter of interest (in this case UV).

Figure 13D:
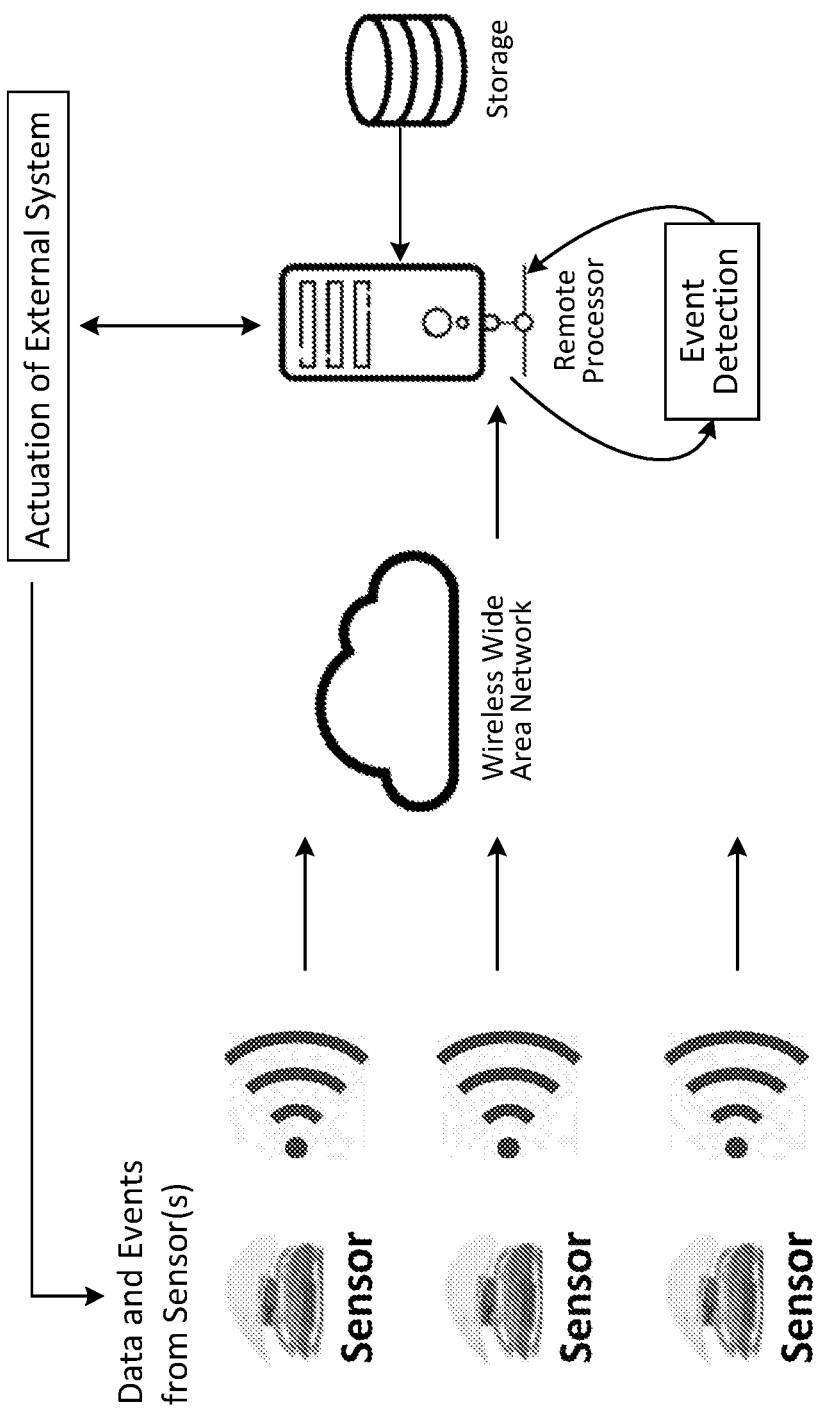
FIG. 13D describes a system for a multiplex of sensors transmitting to an external remote processor via a cellular link, according to embodiments of the invention. This leads to actuation of an external system (e.g. grow lights for agriculture) where it is brightened or darkened—leading to continued sensing by the sensors creating a closed feedback loop.

FIG. 13D describes how this might work for a multiplex of sensors transmitting to an external remote processor via a cellular link. This leads to actuation of an external system grow lights for agriculture) where it is brightened or darkened—leading to continued sensing by the sensors creating a closed feedback loop.

Improved Multi-Node BSN: Since the data capture is based on advertisement packages, there can be many more devices on the body (+20), as shown in FIG. 10. Multiple devices is otherwise a limitation if there is a connection to all the sensors (usually about 8).

Figure 7:
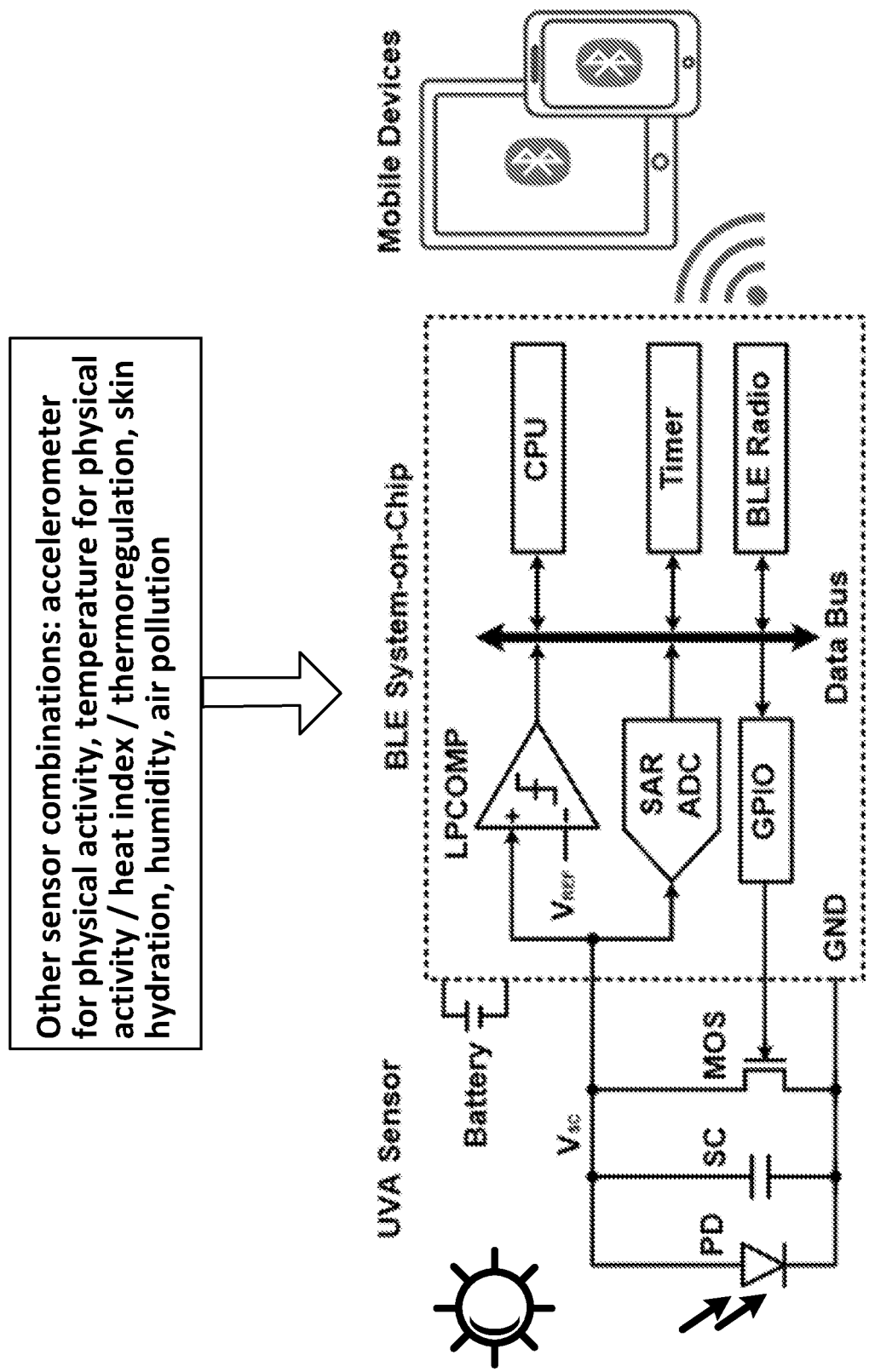
FIG. 7 shows ability to couple cumulative sensing modalities with other sensing modalities that may also be cumulative or instantaneous and continuous, according to embodiments of the invention.
Figure 8:
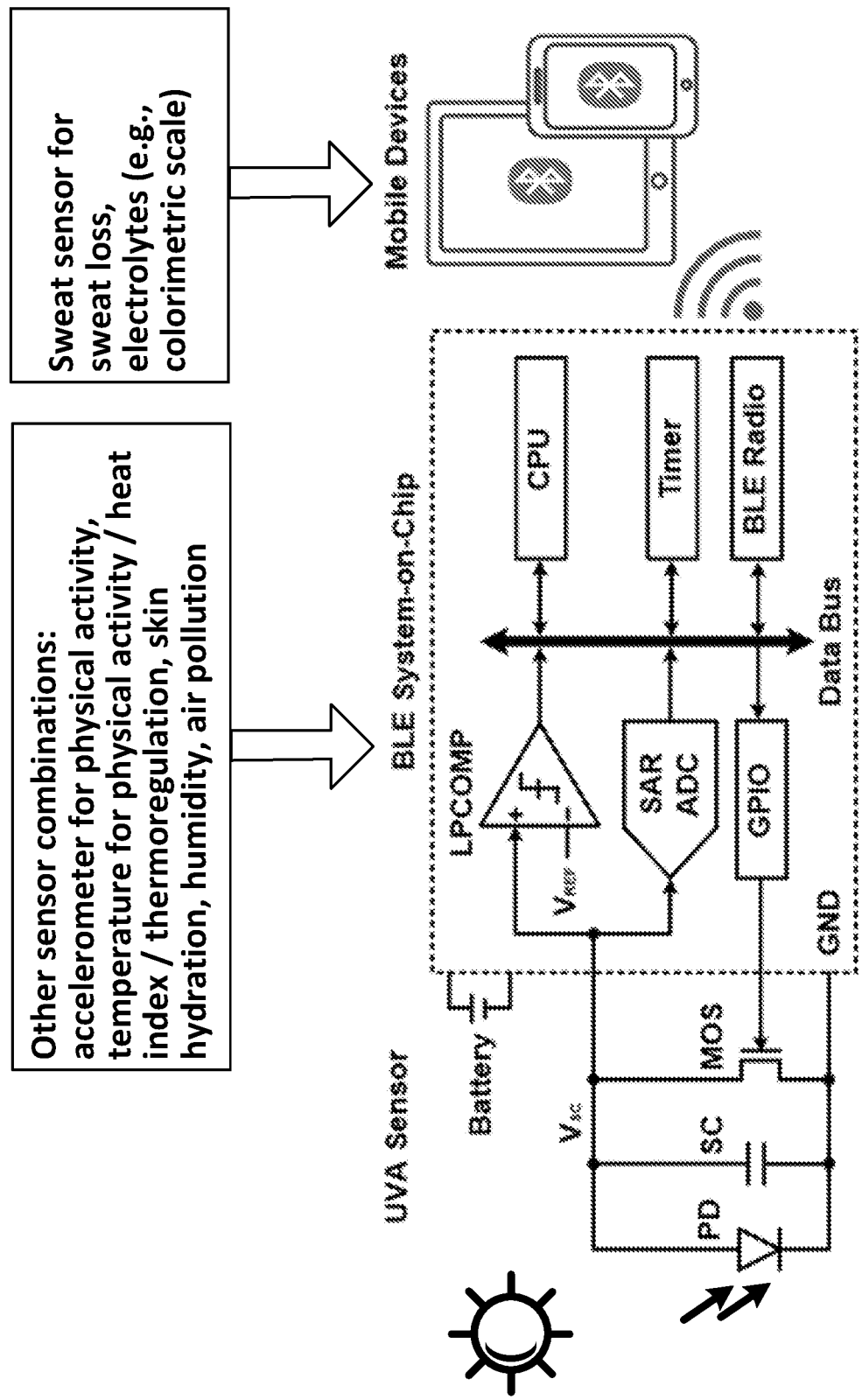
FIG. 8 shows ability to couple cumulative sensing modalities with other off-sensor measurement tools (e.g., sweat sensing patches), according to embodiments of the invention.

Other applications also include, but are not limited to, combinations of cumulative sensing modalities with other sensing modalities that may also be cumulative or instantaneous and continuous. Other sensor combinations include accelerometer for physical activity, temperature for physical activity/heat index/thermoregulation, skin hydration, humidity, air pollution, as shown in FIG. 7. In addition to the embodiment shown in FIG. 7, cumulative sensing modalities can also be combined with other off-sensor measurement tools, e.g., sweat sensor for sweat loss, and/or electrolytes (e.g. colorimetric scale), as shown in FIG. 8.

Figure 9:
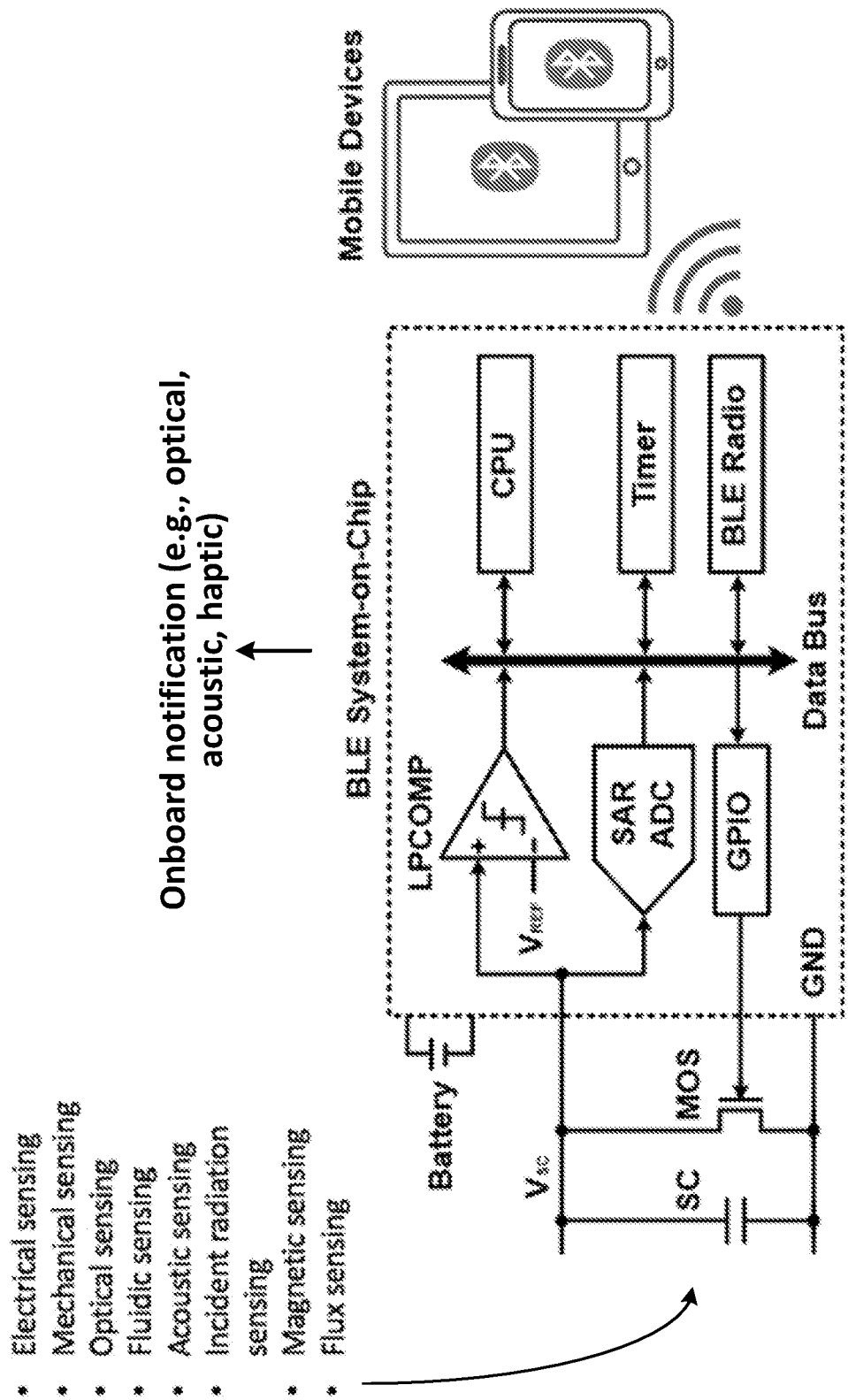
FIG. 9 shows that the PD for UV sensing can be replaced with a wide array of sensors capable of generating current as it relates to an externally or on body parameter (e.g., optical, electrical, mechanical signals), according to embodiments of the invention. This cumulative sensing modality enables deep sleep and ultra-low power consumption for any of a variety of sensors. This embodiment also allows for inclusion of onboard/on-sensor notification once a threshold is set.

Further, as shown in FIG. 9, the PD for UV sensing can be replaced with a wide array of sensors capable of generating current as it relates to an externally or on body parameter, e.g., optical, electrical, mechanical signals. This cumulative sensing modality enables deep sleep and ultra-low power consumption for any of a variety of sensors. This embodiment also allows for inclusion of onboard/on-sensor notification once a threshold is set.

Moreover, the pre-defined threshold that triggers activation of the sensor from deep sleep to read the values on the SC can be hard programmed on the sensor, or set through software on a mobile device, as shown in FIG. 10. The threshold can also be adaptive and personalized based on user inputs, such as on their skin type, behavior and other factors.

As shown in FIG. 11, the small form factor and passive nature of sensing allows for on-body, anatomical specific sensing, according to embodiments of the invention. This serves utility in research settings as well consumer health settings. The identification of high risk locations (e.g., face, hands, neck) can be identified by sensors placed strategically as jewelry (e.g., earrings, rings, necklaces). Sensors placed on the trunk, arms, or legs of a user can be located underneath clothing to identify instances where users may need to apply sunscreen or seek shade even with clothing on— clothing has variable amounts of UV protection. This embodiment allows a continuous stream of multi-sensor data which can then be displayed on the user interface of a mobile phone, such as a user's mobile phone or another person's handheld interested in the user (e.g., a parent, medical caregiver, or headquarter supervisor).

Furthermore, a detection event such as a threshold reached can be used to trigger changes of an environmental condition accordingly.

For example, a detected UV threshold can be used to trigger blinds to close over a structure until desired UV exposure reached, to trigger dimming or brightening of therapeutic phototherapy lights, and/or to trigger warning of potential risk of ocular damage for a welder. This external actuator could be a buzzer clipped to the belt or audio notification on the mobile device.

A detected blue light threshold can be used to trigger dimming of lights or blue light filter on a screen of a mobile device or computer, to trigger driving current of an external blue light phototherapy system for neonatal jaundice, and/or to trigger driving current of an external blue light phototherapy for photodynamic therapy.

A detected visible light threshold can be used to trigger brightening of white lights for seasonal affect disorder, to trigger dimming of lights for patients with migraines. Imagine someone wearing a sensor on their body with migraines. They walk into a room with bright lights that automatically dims due to the patient's condition, and/or to trigger dimming of lights or screen protection for a piece of high value art or any photosensitive decorative display.

A detected acoustic threshold can be used to trigger soften or increase volume of music.

A detected red/blue light threshold can be used to trigger dim or brighten agricultural grow lights.

Example 2

Miniaturized, Light-Adaptive, Wireless Dosimeters for Autonomously Monitoring Exposure to Electromagnetic Radiation Exposure to electromagnetic radiation (EMR) from the sun and from artificial lighting systems represents a modifiable risk factor for a broad range of health conditions including skin cancer, skin aging, sleep and mood disorders, and retinal damage. Technologies for personalized EMR dosimetry could guide lifestyles toward behaviors that ensure healthy levels of exposure. The most advanced approaches involve light-responsive colorimetric chemical reagents in analog platforms that cannot be reused and near field communication hardware in digital systems that require close proximity to a separate device for data extraction.

In this exemplary example, we report a millimeter-scale, ultra-low power digital dosimeter platform that provides continuous EMR dosimetry in an autonomous mode at one or multiple wavelengths simultaneously, with time-managed wireless, long-range communication to standard consumer devices. A single, small button cell battery supports a multi-year lifespan, enabled by the combined use of a light-powered, accumulation mode of detection and a light-adaptive, ultra-low power circuit design. Field studies demonstrate single- and multi-modal dosimetry platforms of this type, with a focus on monitoring short-wavelength blue light from indoor lighting and display systems, and ultraviolet/visible/infrared radiation from the sun.

EMR from the sun and from indoor lamps, emissive displays and other artificial sources have wavelength-specific and dose-dependent effects on underlying life processes that determine health status. The adverse influences of overexposure or underexposure to EMR accumulate over time and their consequences can be latent. Specifically, excessive exposure to ultraviolet radiation (UVR) and blue light from the sun or from sources of emission such as those in tanning beds and cellphones have varied associated risks. Repetitive keratinocyte damage from chronic exposure to UVR is the primary cause of skin cancer—the most commonly diagnosed form of cancer in the US. The shorter wavelengths of visible spectrum (VIS) generate reactive oxygen species in the skin, which can lead to DNA damage that causes inflammation as well as hyperpigmentation, and potentiates degradation of collagen and elastin, thereby contributing to photo-aging and skin wrinkling. Above certain thresholds, blue light can cause photochemical damage in retinal tissue and accelerate age-related maculopathy. Additional effects modulate retinal control of human circadian rhythms, including suppressed secretion of melatonin. On the other hand, moderate doses of UVR and VIS are essential for vitamin D production and for immunomodulation. Insufficient exposure can also lead to seasonal affective disorder (SAD), typically treated with bright light therapy.

Technologies that provide convenient, immediate access to personalized information on wavelength-specific exposure to EMR could guide behaviors to prevent adverse health outcomes, from sunburns and skin cancer to mood swings and sleep disorders. Previously reported approaches focus almost exclusively on UVR measurements using color-changing chemical reagents or digitally sampled outputs of UVR photodetectors. The former provides semi-quantitative information in platforms that cannot be re-used. The latter is susceptible to sampling errors, with operating lifetimes that are limited by battery capacities. The most recent schemes involve miniaturized, highly accurate dosimeters that exploit a light-powered, continuous mode of detection and battery-free operation. Here, current from a photodetector accumulates on a storage capacitor such that the resulting voltage corresponds directly to dose, via a calibration factor. In reported systems, a miniaturized loop antenna supports near field communication (NFC) protocols as digital, wireless interface to the phone for data acquisition. The main disadvantage of these millimeter-scale NFC (mm-NFC) devices is that they require active user engagement for data acquisition and device reset (capacitor discharge), via a 'swipe' of the phone.

An ideal platform would offer automatic and remote wireless updates, while retaining many of the other appealing attributes of the accumulation mode, mm-NFC approach. Certain aspect of this invention shown in the exemplary example discloses such a technology, based on the combined use of an advanced, light-adaptive electronic control circuits with an accumulation detection module (ADM) for dosimetry and a Bluetooth® Low Energy (BLE) system on a chip (SoC) for wireless communication. In certain embodiments, even some of the smallest button cell batteries (MS621F) can support more than 1.2 years of continuous operation in an 'always on' mode that functions autonomously, without requirements for any form of user engagement. The total size of the resulting device is only slightly larger than that of recently launched commercial mm-NFC dosimeter systems, thereby supporting a broad range of options for personal use, such as mounting on glasses, earphones, shoelaces, watchbands, bracelets, pendants or other accessories. Lack of interface ports, mechanical switches, and absence of need for battery replacement allows hermetic sealing of the device for waterproof, sweat-resistant, and wear-resistant capabilities.

The key feature of the ADM is that it directly measures exposure dose in a continuous fashion, without any power consumption. By contrast, conventional digital approaches approximate dose through computational time integration across a series of brief measurements of intensity, each performed using active, battery-powered electronics, where increasing the sampling frequency increases the accuracy, but decreases the battery life. The ADM eliminates this trade-off, to enable highly accurate dosimetry even with extremely long intervals between active measurements. The active, light-adaptive circuit design introduced in the exemplary example automatically adjusts the temporal frequency for interrogating the ADM in a manner that depends on the intensity of the irradiation. In the absence of light, the device remains in an ultra-low power sleep mode (about 0.4 μA) while continuously monitoring the dose vithe ADM. When the dose exceeds a set threshold value, the device briefly wakes-up (about 10 μA), wirelessly transmits exposure information using BLE protocols, resets the ADM and then quickly returns to sleep mode. The result is an exceptionally power-efficient dosimeter that automatically regulates its operation and communication to the phone on an adaptive, as-needed basis to enable a millimeter scale form factor with a battery life of many years, corresponding to a device that is both always on and effectively everlasting, without any user engagement. Some embodiments of the device's circuit designs, operating principles and key factors that determine lifetime and accuracy are described as follows. An application focus is on dosimetry of blue light and on multi-spectral measurements in the UVR, blue, infrared (IR) regions of the spectrum, with several examples in field trials studies.

Fabrication Procedures

A thin, flexible sheet (AP8535R, Pyralux) of copper (thickness, 18 μm)/polyimide (thickness, 75 μm)/copper (thickness, 18 μm) served as a substrate. A UV laser system (Protolaser U4, LPKF) ablated the copper to define conductive traces and through-hole vias. A galvanic pulsed electroplating system (Contac S4, LPKF) created conductive plugs of copper between the two patterned copper layers through the vias. In/Ag soldering paste (Ind. 290, Indium Corporation) heated at 90° C. served as solder joints for surface-mount components such as BLE, SC, UVA PD, UVB PD, blue PD, and MOSFET. Polydimethylsiloxane (PDMS) (sylgard 184, DOW corning) molded and cured at 70° C. formed a robust encapsulating structure.

Calibration of Outdoor Dosimeters

Calibration involved exposure to the outdoor sun with constant intensity on a clear day without clouds during the solar noon. Blue light (Visible Blue Light Meter, Solarmeter) and UVA photometers (Sensitive UVA Meter, Solarmeter) measured the intensity of incident solar light. Time integration of the measured intensity is the accumulated dose of blue light or of UVA exposure. A BLE-enabled phone (e.g., iPhone 6) wirelessly acquired voltage measurements of the dosimeters for all 'wake-up' events.

Real-Time Measurements of Current Consumption

The Power Profiler Kit (PPK) board (NRF6707, Nordic Semiconductor) served as a current measurement tool for the dosimeters. The PPK supplied power to BLE blue light dosimeter through the external device under test (DUT) connectors, and used its ADC to measure a voltage drop over a series of measurement resistors. The real-time current consumed by blue light dosimeter is I [A]=measured voltage drop [V]/resistor value [ohm]. The PPK provided current measurements with a resolution down to 0.2 μA and a real-time display with a resolution down to 13 μs to the desktop application. By mounting the PPK on an nRF52 development kit (DK) board (NRF52-DK, Nordic Semiconductor), the nRF52-DK provided the connection between the PPK and the computer with the PPK application. The PPK software was an app running in nRF Connect, a cross-platform development software for BLE.

BLE Communication Modalities

In a connected mode, the device must satisfy connection rules provided by the user interface to establish a connection link. The connection parameter that complies with Accessory Design Guide for Apple Devices (Release R8) is slave latency=3, and maximum connection interval=500 ms such that maximum connection interval×(slave latency+1)≤2 s. Devices under these connection rules exchange data packets with the user interface every 2 s to maintain connected status even when there is no need to transmit user data. This operation significantly degrades the overall power efficiency of the device. In an advertising mode, BLE devices send data to any listening user interface that knows the device ID without establishing any connection. This mode enables efficient BLE operations for low duty cycle applications such as those described herein.

Circuit Designs and Operating Principles

Figure 19:
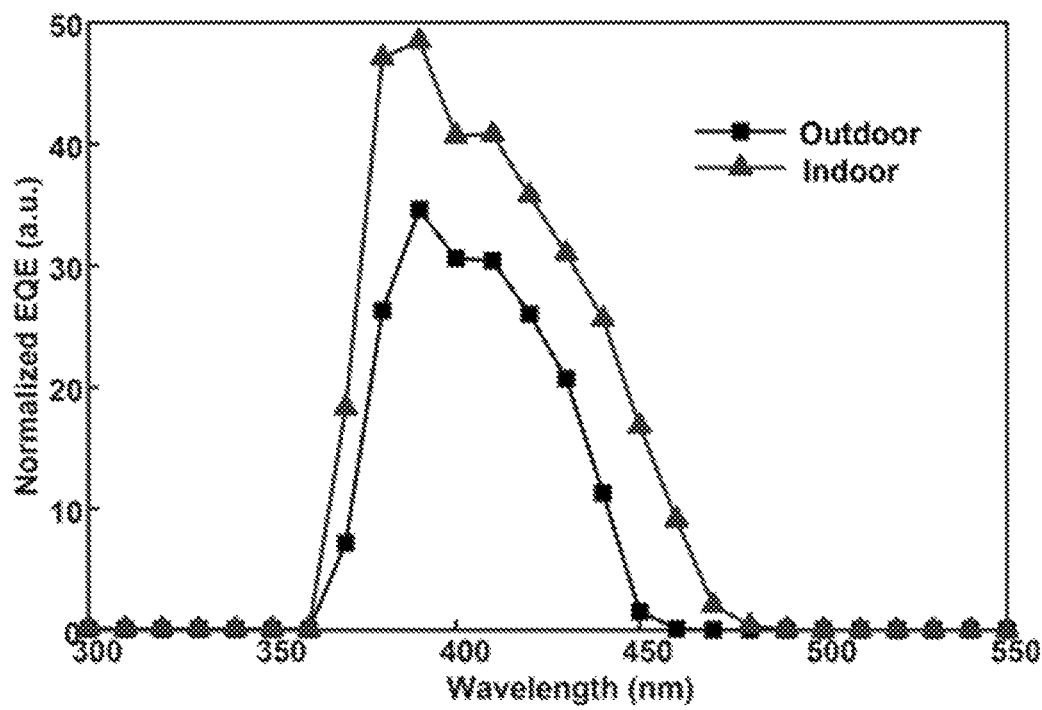
FIG. 19 shows external quantum efficiency (EQE) of a blue light PD, according to embodiments of the invention.

The device shown in FIG. 14A in one embodiment exploits the unique design features described above for dosimetry of blue light with an estimated operating lifetime of 1.2 years. The width (w), length (l), thickness, and weight are 8.1 mm, 10.9 mm, 3.2 mm, and 0.36 g, respectively. Two subsystems shown in FIG. 14B are key to efficient, ultra-low power operation and long lifetime in this miniaturized form factor: 1) the ADM, as a light-powered sensing system that continuously measures exposure dose in an accumulation mode, and 2) a BLE SoC configured with a light-adaptive circuit design to automatically switch between two operational states: 'run' and 'sleep', in response to changing irradiation conditions. The ADM includes a photodiode (PD), a supercapacitor (SC), and a MOSFET. The PD continuously and passively generates photocurrent with a magnitude that is directly and linearly proportional to the intensity of the exposure light. The SC, arranged in parallel with the PD, captures and stores the resulting accumulated charge. The corresponding voltage on the SC ($V_{SC}$) can be calibrated to the total exposure dose across a wavelength range defined by the external quantum efficiency (EQE) of the PD, as shown in FIG. 19. To prevent excessive charge buildup on the SC, the gate of a metal oxide semiconductor field-effect transistor (MOSFET) connects to a general-purpose input/output (GPIO) of the BLE SoC for programmable control of current flow between the source and the drain of the MOSFET, as means to trigger the discharge of the SC.

Figure 20:
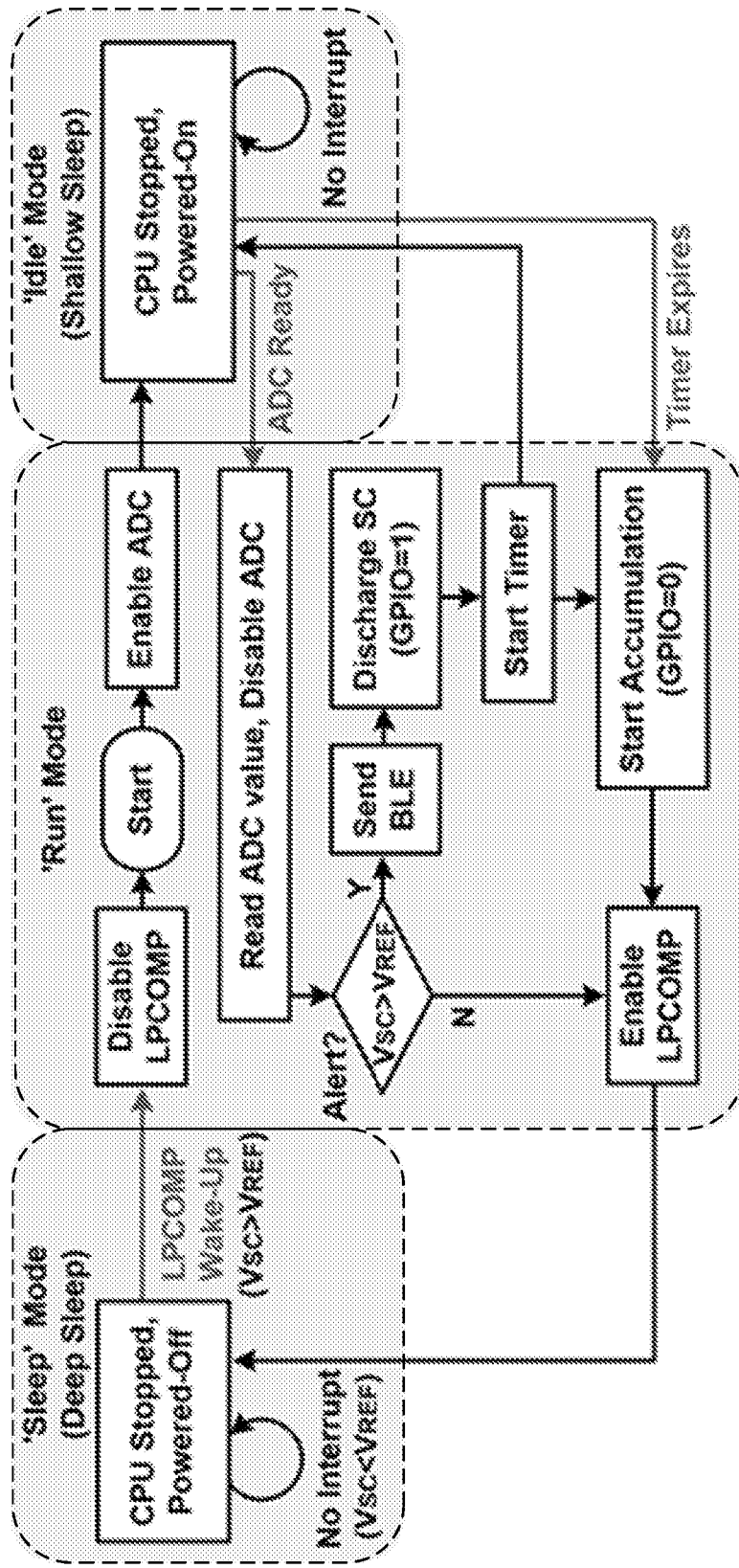
FIG. 20 shows a flowchart of a BLE blue light sensing system utilizing ultra-low power sleep/wake-up capability, according to embodiments of the invention. When BLE operation starts, CPU triggers ADC sampling and goes into 'idle' mode (shallow sleep mode), which makes the entire BLE SoC, except ADC and Timer, wait in a halt status. When the ADC reports a ready interrupt, the CPU wakes up, reads the ADC value and compares the SC voltage ($V_{SC}$) against a preprogrammed reference voltage ($V_{REF}$). At low blue-light conditions, $V_{SC}<V_{REF}$, CPU enables LPCOMP to monitor $V_{SC}$ and goes into 'sleep' mode (deep sleep mode), which powers down the entire SoC except LPCOMP. The device remains in deep sleep in no light conditions indoors or during nighttime. When $V_{SC}$ rises above $V_{REF}$, CPU wakes up and runs the program from the starting point. At high blue-light conditions ($V_{SC}>V_{REF}$), CPU alerts the user by sending BLE packets, starts discharging SC (sets GPIO as high voltage) and enters 'idle' mode. After a preprogrammed discharging duration (e.g., 5 s), CPU wakes up and finishes discharging (sets GPIO as low voltage) and goes in to 'sleep' mode.

In light-adaptive operation, a low-power comparator (LP-COMP) of the BLE SoC monitors $V_{SC}$ while the device is in an ultra-low power 'sleep' mode. When $V_{SC}$ exceeds a preprogrammed reference voltage ($V_{REF}$), the LPCOMP generates a 'wake-up' event that places the BLE SoC in a 'run' mode for about 6.5 s, with average current consumption of about 10.22 μA. In the exemplary embodiment, the central processing unit (CPU) is configured to wirelessly transmit the input voltage of the ADC that connects to the SC, activate the MOSFET to discharge the SC and then return the system to a 'sleep' mode. The time required to sample the input voltage of the ADC, transmit BLE packets, and discharge the SC (e.g., 5 s) determines the 'run' time. Unless the voltage on the SC exceeds $V_{REF}$, the device remains in the 'sleep' mode, where the CPU and all the peripherals except LPCOMP are deactivated, thereby reducing the average current consumption to about 0.43 μA, roughly twenty times less than that associated with the 'run' mode. FIG. 14C graphically illustrates the overall operation, where in the absence of light, the device remains in 'sleep' mode until the exposure dose determined by the ADM exceeds $V_{REF}$, at which time the CPU 'wakes-up', wirelessly transmits data, discharges the ADM and returns to 'sleep'. The 'wake-up' frequency increases with increasing irradiance in the wavelength range defined by the EQE of the PD. The purpose of this light-adaptive operation is two-fold: 1) to frequently alert users of their exposure doses during high intensity irradiation conditions, while remaining in 'sleep' for extended periods during conditions of low or no irradiation, and 2) to autonomously and efficiently manage power consumption based on the need for detection. The flowchart of the device operations is shown in FIG. 20. As an additional option to avoid unexpected data loss due to disruption of the wireless connection to the phone, the device can be programmed to write dosage data into memory available on the BLE SoC, as described in detail subsequently.

Figure 14D:
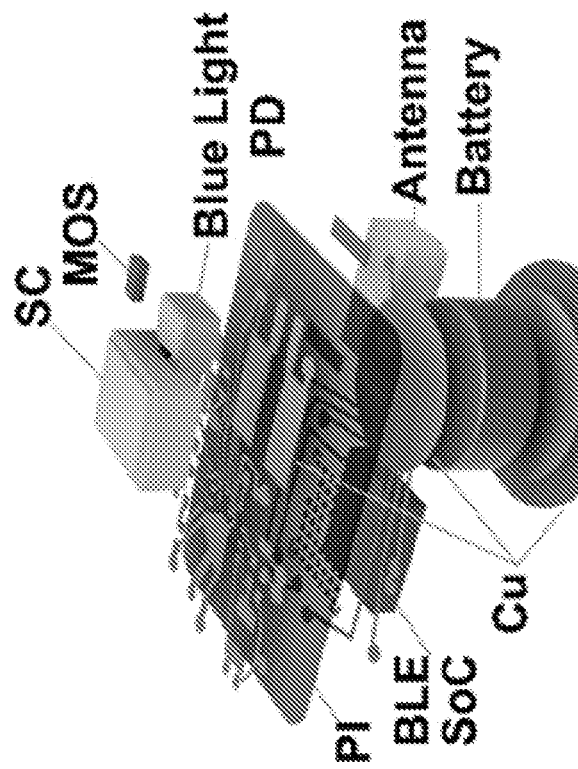
Figure 14C:
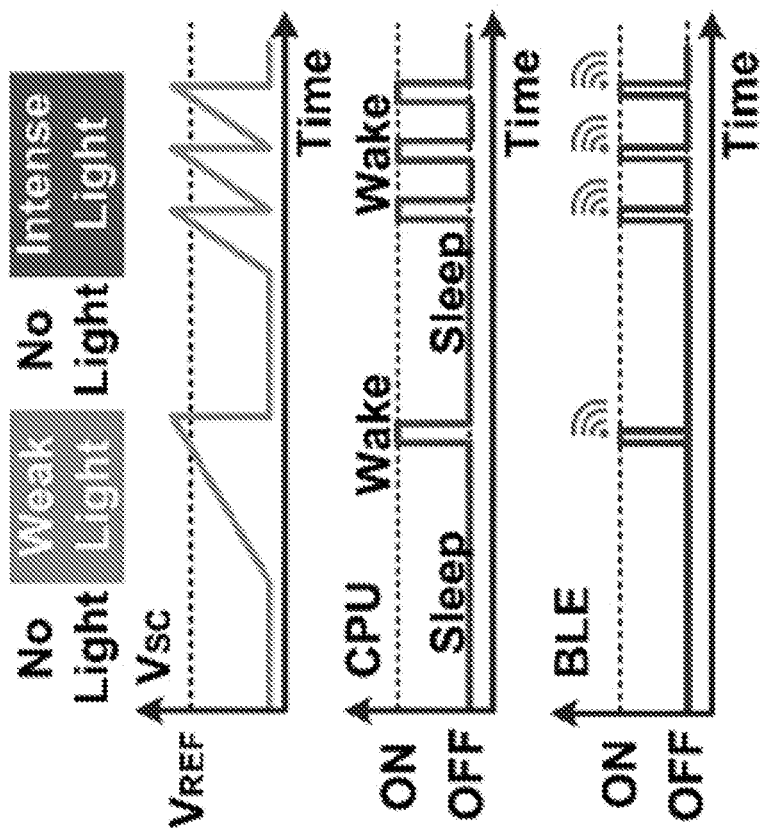
Figure 14E:
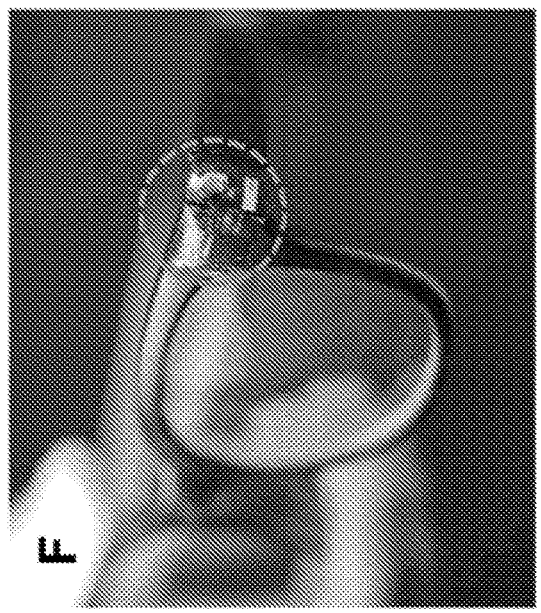
Figure 14F:
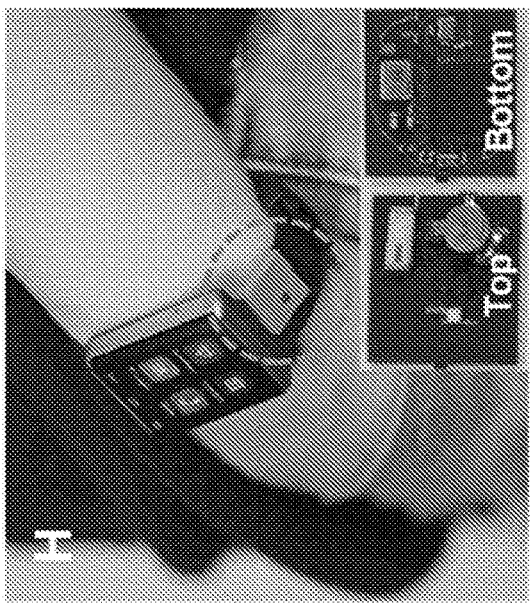
Figure 14G:
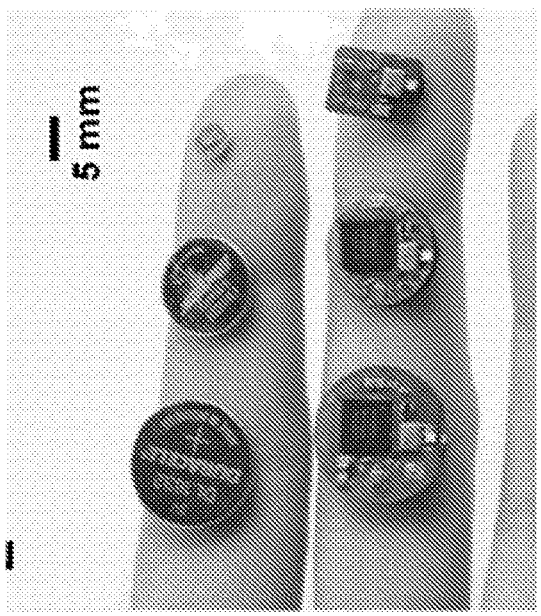
Figure 14H:
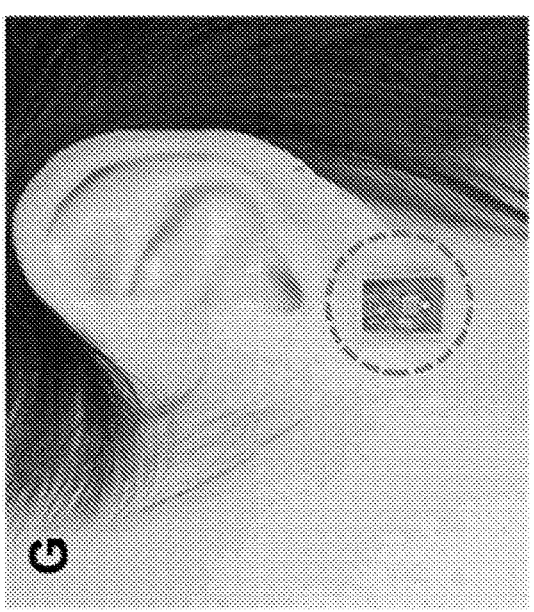

The devices use thin (112 μm thickness) copper-clad polyimide sheets processed with a laser cutting tool to define interconnecting traces of Cu and support pads for bonding off-the-shelf, surface-mount components by soldering, as shown in FIG. 14D. The battery is a key factor in determining the overall size and weight, as well as the operating lifetime. FIG. 14E shows different blue light dosimeters built with coin cell batteries that have capacities of 140 mAh, 40 mAh, and 5.5 mAh, where the device diameters (d) are 16.6 mm and 13.5 mm, and the length and width (l×w) are 8.1 mm×10.9 mm, respectively. With assumptions that (i) blue light exposure from the sun occurs at a constant intensity of 7.8 mW/cm² (moderate level outdoors), and (ii) exposure at this level occurs for a total of 6 hours in a typical day, the estimated operating lifetimes of these dosimeters are, in the order of decreasing sizes, greater than 30.9 years, 8.8 years, and 1.2 years. The miniaturized form factors allow many options and modes of use. Examples include sunglass clips as shown in FIG. 14F, earrings as shown in FIG. 14G and wristband accessories as shown in FIG. 14H. The devices in hermetic housings of different designs (FIGS. 14F-14H) enhance the operational reliability from environmental and mechanical influences.

Blue Light Dosimeters Designed for Use Outdoors

Seasonal Affective Disorder (SAD) is a relatively common condition in North America and a widespread cause of depression in the winter months. The treatment for the SAD involves regular phototherapy using light from natural sources, or a bright white-LED or blue-LED illumination panels. Information from personal blue light dosimeters can help to guide behaviors that meet recommended daily doses of exposure to prevent mood disorders. This section demonstrates the use of devices with designs outlined in the previous sections, tailored for monitoring sun exposure at varying irradiance levels. Measurements of current consumption allow estimations of battery life for these use cases. The devices use a blue PD with peak responses at 390 nm, as shown in FIG. 19 and a SC with a capacitance of 11.5 mF.

Figure 15B:
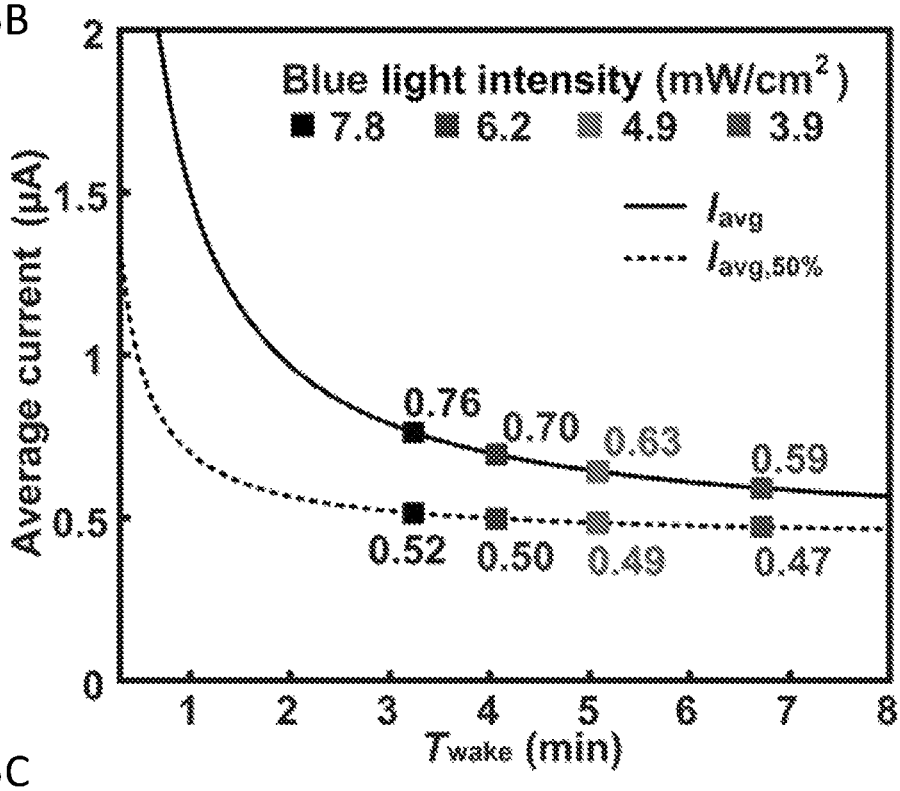
Figure 15C:
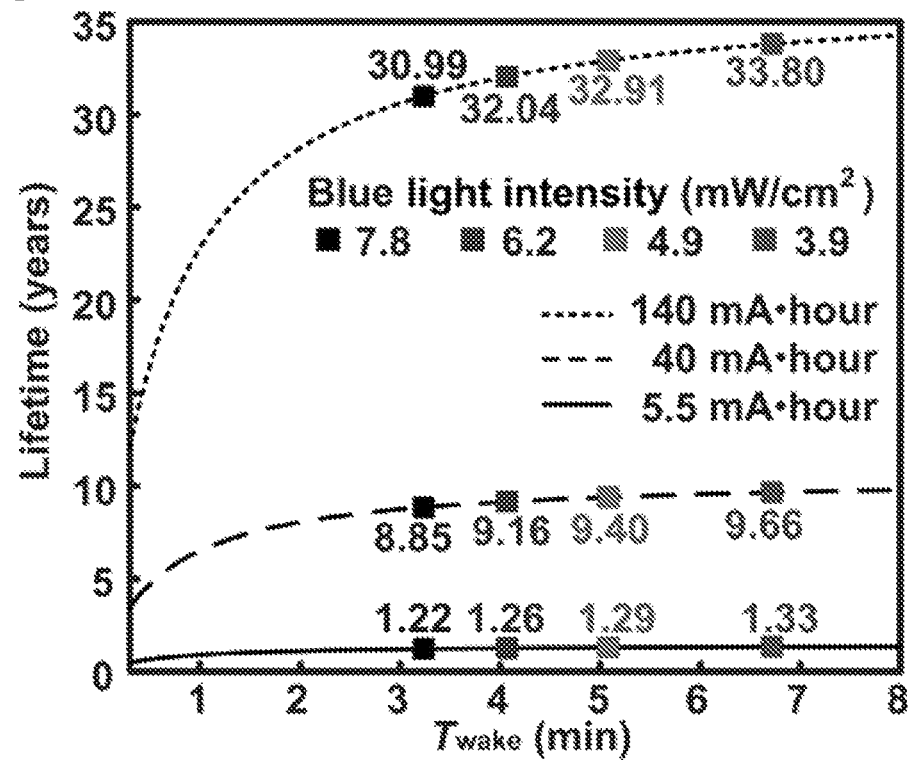
Figure 21:
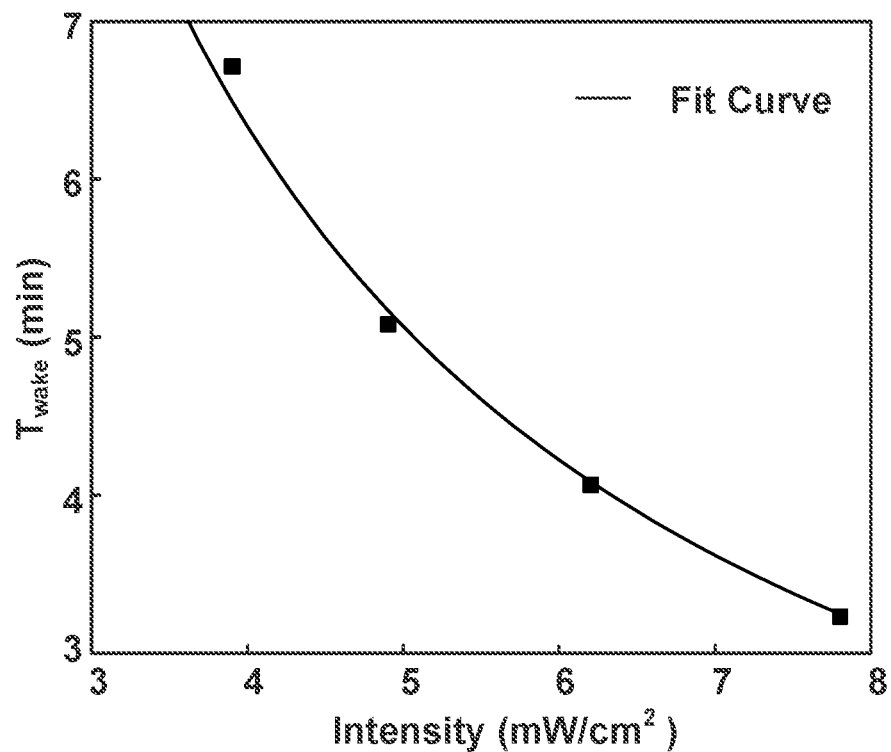
FIG. 21 shows measured time intervals ($T_{wake}$) between 'wake-up' events as a function of exposure intensity, according to embodiments of the invention. Fit Curve: Intensity [W/cm²]×$T_{wake}$ [s]=Exposure dose ($D_{tot}$)=1.52 J/cm².
Figure 22A:
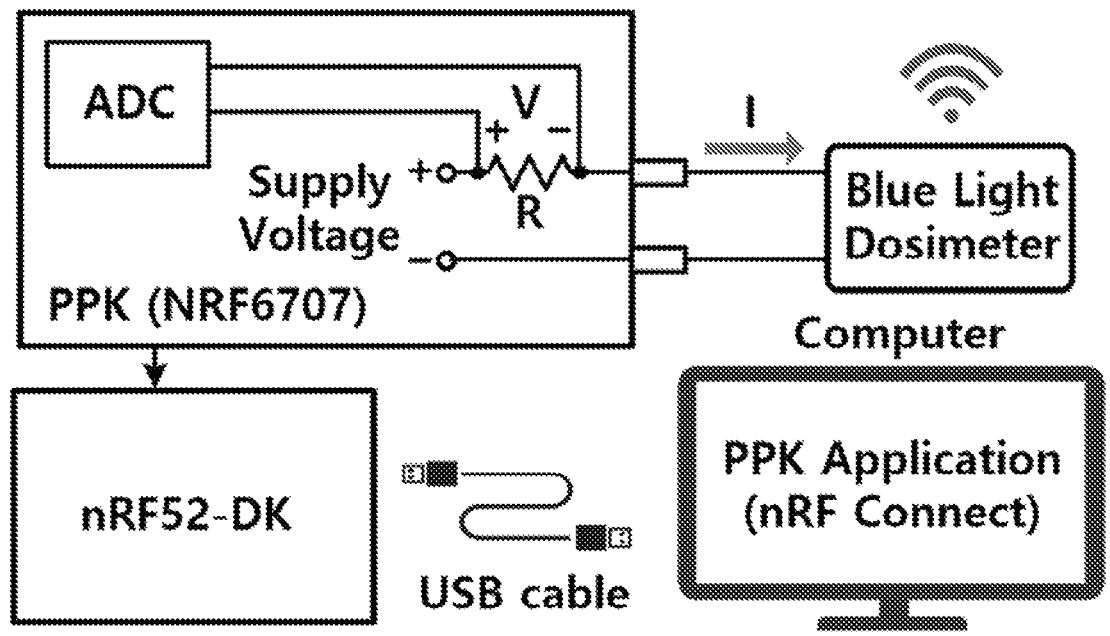
FIGS. 22A-22D show real-time current measurements of BLE blue light dosimeters, according to embodiments of the invention.
Figure 22B:
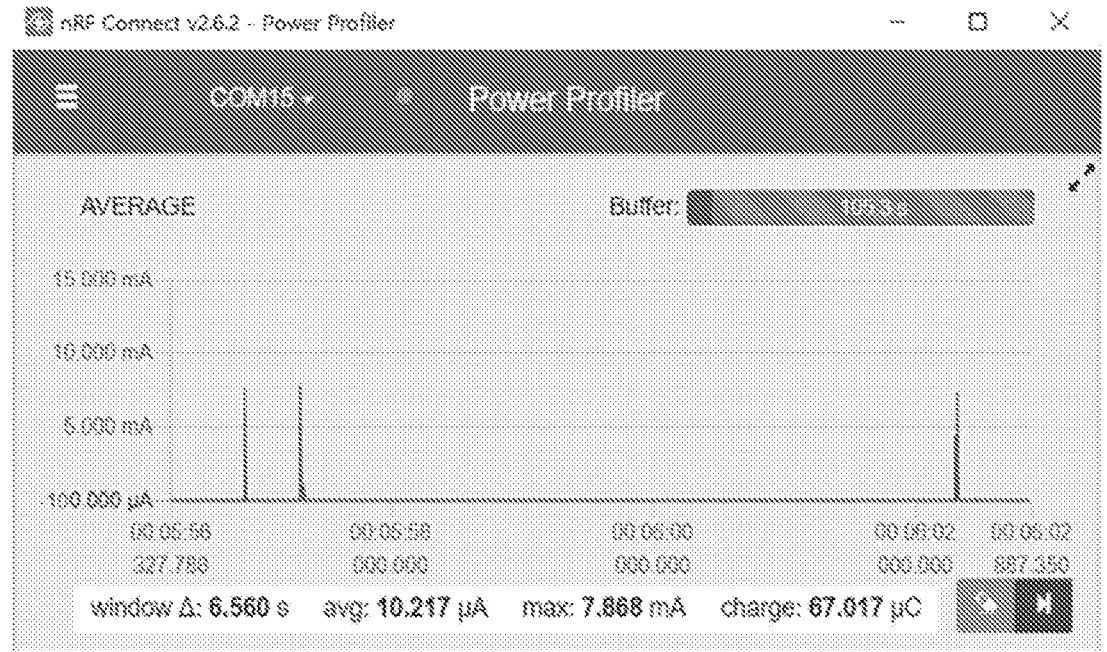
Figure 22C:
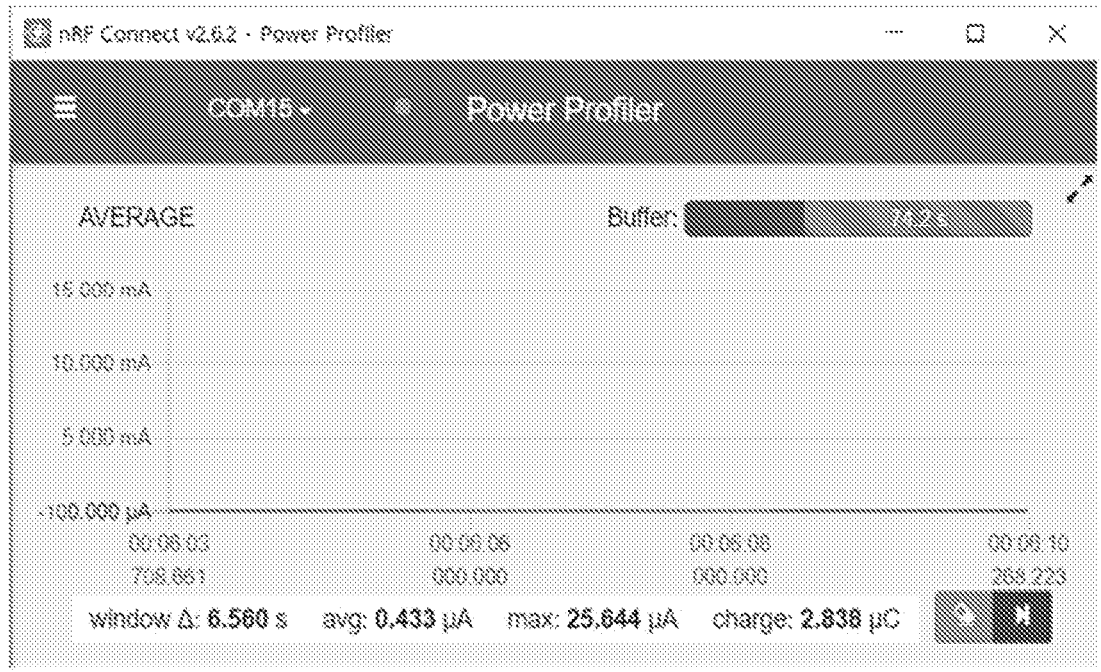
Figure 22D:
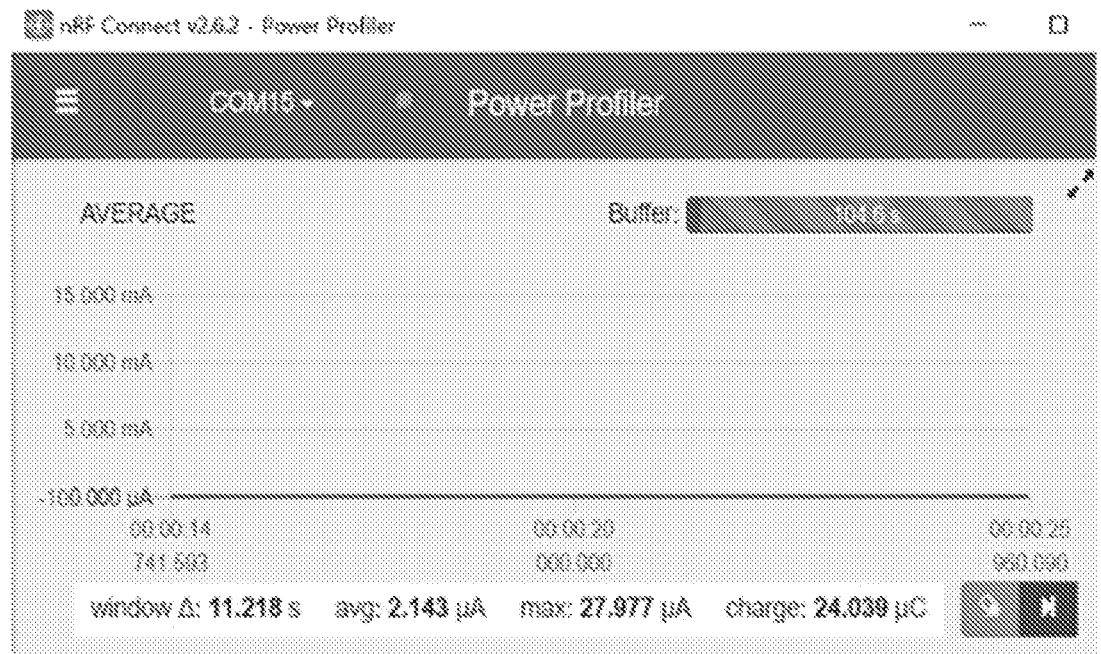
Figure 23B:
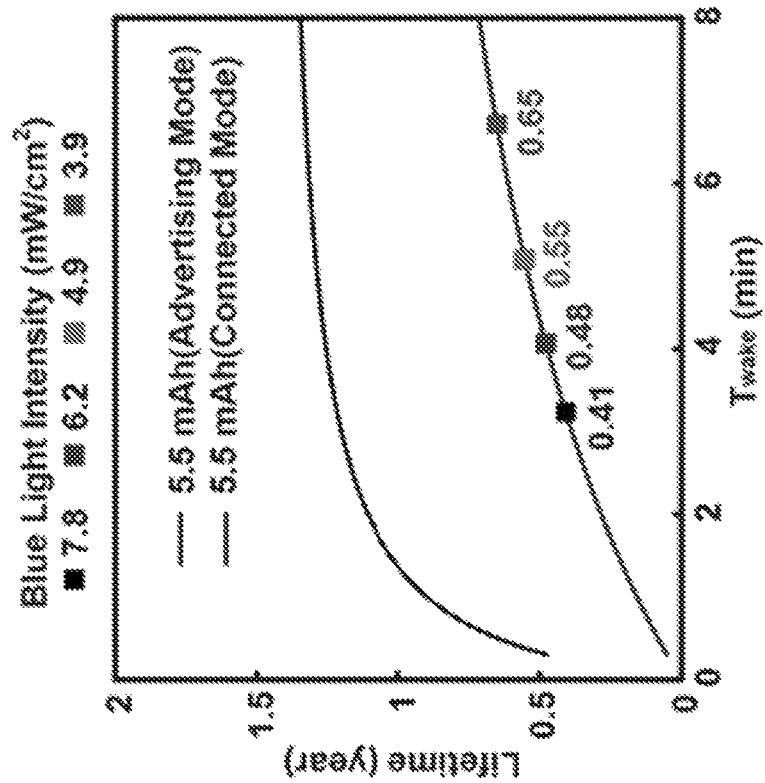
FIGS. 23A-23B show power consumption and expected lifetime of BLE dosimeters in connected mode, according to embodiments of the invention.
Figure 23A:
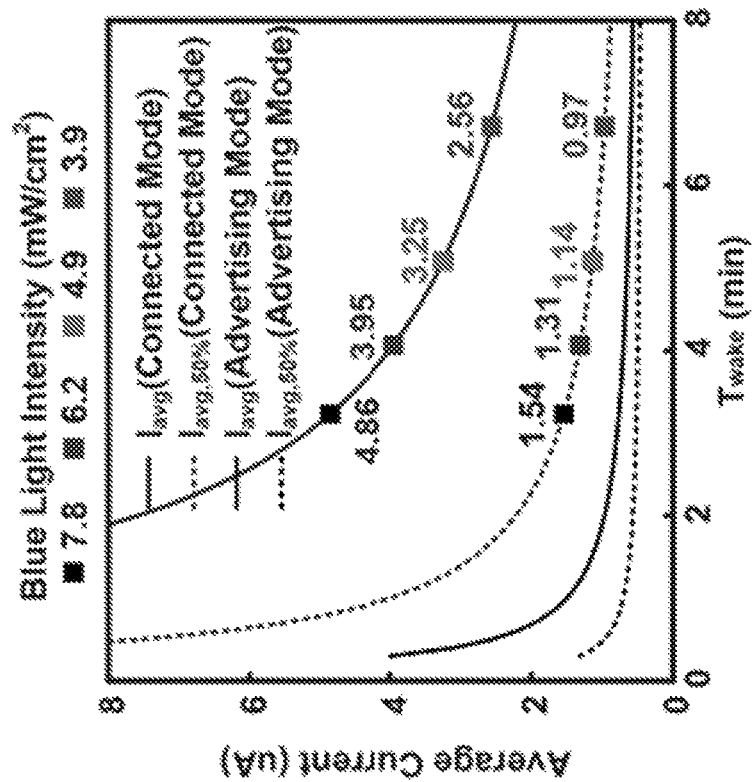

Calibrations involved exposure of the device to the sun on a clear day and to the sun attenuated 80%, 63%, 50% by neutral density filters, corresponding to high to low irradiation conditions. A commercial blue-light radiometer (Visible Blue Light Meter, Solarmeter) measured the reference exposure intensity. The time integration of reference exposure intensity over $T_{wake}$ is the reference exposure dose. A BLE-enabled smartphone wirelessly receives alerts at each 'wake-up' event. For constant reference exposure intensities of 7.8 mW/cm², 6.2 mW/cm², 4.9 mW/cm², and 3.9 mW/cm², the time intervals between 'wake-up' events ($T_{wake}$) are 3.2 min, 4.1 min, 5.1 min, and 6.7 min, respectively, as shown in FIG. 15A. As the reference irradiation intensity decreases, $T_{wake}$ increases proportionally, as shown in FIG. 21, such that the exposure dose ($D_{tot}$) of blue light at each 'wake-up' event is $D_{tot}$=Intensity [W/cm²]×$T_{wake}$ [s]=1.52±0.03 J/cm². $T_{wake}$ is a determining factor in computing the average current ($I_{avg}$) consumption of the device: $I_{avg}=[I_{run,avg} \times T_{run} + I_{sleep,avg} \times (T_{wake}-T_{run})]/T_{wake}$. Methods for measuring real-time current consumption are described in the section of methods below and shown in FIGS. 22A-22D. BLE dosimetry can occur in two wireless BLE transmission modalities: connected and advertising modes. The devices measured here operates in the advertising mode. The current measurements for the connected mode are shown in FIGS. 23A-23B. The average current consumption shown in FIGS. 22A-22D in the 'sleep' mode is $I_{sleep,avg}$=0.43 μA and in the 'run' mode is $I_{run,avg}$=10.22 μA. The runtime after wake-up events is $T_{run}=T_{ADC}+T_{BLE}+T_{DSC}$=6.56 s, where $T_{ADC}$ and $T_{BLE}$ is the time required to sample the ADC input voltage and to transmit the sampled data via BLE, respectively, and $T_{DSC}$ is a preprogrammed time (e.g., 5 s) to fully discharge the SC. In light-adaptive operation, as the irradiation intensity increases, $T_{wake}$ decreases proportionally and $I_{avg}$ increases. For constant exposure intensities of 7.8 mW/cm², 6.2 mW/cm², 4.9 mW/cm², and 3.9 mW/cm², the $I_{avg}$ are 0.76 μA, 0.70 μA, 0.63 μA, and 0.59 μA, respectively, as shown in FIG. 15B. The average current for 365×6 hours of use per year corresponding to 50% of the available daylight is $I_{avg,50\%}=I_{avg} \times 6$ [h]/24 [h]+$I_{sleep,avg} \times 18$ [h]/24 [h]. In the 50% exposure condition, the device lifetime is lifetime [h]=battery capacity [mAh]/$I_{avg,50\%}$ [mA]. As an illustrative example, a device powered by a button cell battery with a capacity of 5.5 mAh, continuously exposed at a constant intensity of 7.8 mW/cm², has an expected lifetime of 1.2 years, as shown in FIG. 15C, with an average current of $I_{avg,50\%}$=0.52 μA for 50% of the available daylight. With assumptions that (i) blue light exposure from the sun occurs at a constant intensity of 7.8 mW/cm² (moderate level outdoors), and (ii) exposure at this level occurs for a total of 6 hours in a typical day, the estimated operating lifetimes of these dosimeters are, in the order of decreasing sizes, more than 30.9 years, 8.8 years, and 1.2 years.

On-chip data retention capabilities can be used to prevent data loss upon loss of a wireless connection to the phone. The BLE SoC (nRF5283, Nordic Semiconductor) supports 4 KB static random access memory (SRAM) that can be used for this purpose. As a specific example of this mode of operation, the device can be programmed to store the latest 10 measurement events (10×2 Bytes) in the SRAM. Transmission of the entire data set then occurs upon each 'wake-up' event. When the phone is within the communication range of the device, the application reads and compares the acquired data array to the data history stored on the phone and performs updates with any new data, as necessary. With the SRAM used in this manner, the average current consumption in the 'sleep' mode increases to $I_{sleep,avg}$=0.788 μA, roughly two times greater than that associated with operation without the SRAM. For transmission of the data set, the average current consumption in 'run' mode is $I_{run,avg}$=10.459 µA, and the runtime after wake-up events is $T_{run}$=7 s. Devices with SRAM data retention in the 50% exposure condition at an intensity of 7.8 mW/cm² consume an average current of $I_{avg,50\%}$=0.88 µA, roughly 1.7 times greater than operation without the SRAM; the corresponding lifetimes are therefore smaller by a factor of 0.59.

Conventional BLE dosimeters numerically integrate values of intensity measured in a fixed schedule (e.g., once per 30 s) that balances accuracy and power consumption, in a manner described previously. Between measurements, the CPU remains powered on but in an 'idle' mode (shallow 'sleep' mode) that does not involve execution of any instructions. In this example, the average current ($I_{idle,avg}$) is about 2.14 µA, as shown in FIG. 22D, roughly five times more than that associated with the 'sleep' mode. Device designs with SRAM data retention like those described in the previous paragraph in the 50% exposure condition at an intensity of 7.8 mW/cm² offer operating lifetimes of 0.72 years with a 5.5 mAh battery, compared to only 8.02 weeks for an otherwise similar device with a conventional, instantaneous-mode of operation with a typical value of $T_{wake}$=30 s.

As an alternative to the 'analog' accumulation-mode sensing of the ADM described above, BLE devices can be programmed to operate in an equivalent 'digital' accumulation-mode that involves frequently sampling the intensity from the PD, computing the corresponding dose and then storing this information locally in SRAM. When the digitally accumulated dose exceeds a certain level, wireless transmission occurs. Between measurement and transmission, device remains in an 'idle' mode until the sampling timer expires. The average current consumption in 'run' mode for data sampling/storage and for BLE transmission are $I_{run,data}$=2.64 µA and $I_{run,BLE}$=4.89 µA, respectively, and the runtime is $T_{run}$=5.28 s. The average current consumed with $T_{wake}$=30 s and $T_{BLE}$=3.2 min as in an exposure scenario involving daylight at a constant intensity of 7.8 mW/cm² is $I_{avg,50\%}$=2.21 µA. The projected lifetime is 14.8 weeks, roughly two times more than that associated with a conventional, instantaneous-mode device at a typical value of $T_{wake}$=30 s, but still far less than that enabled by the ADM and light-adaptive mode highlighted in this paper.

Blue Light Dosimeters Designed for Use Indoors

Figure 24A:
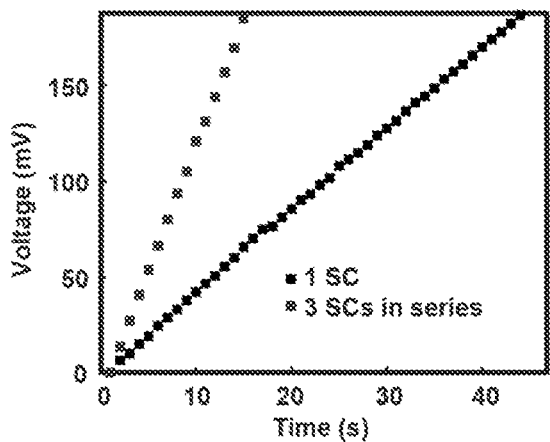
FIGS. 24A-24F show blue light dosimeters with high detection sensitivity for monitoring short-wavelength blue light from indoor lighting and display systems, according to embodiments of the invention.
Figure 24B:
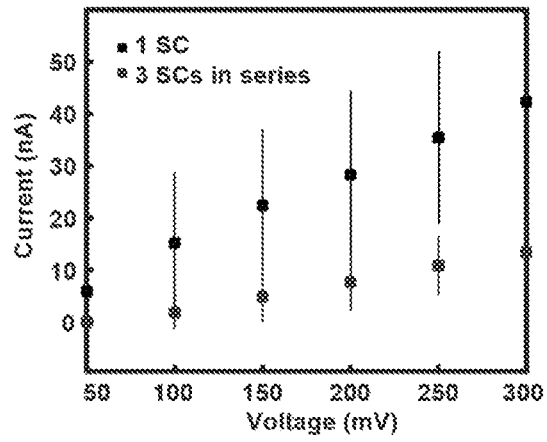

Artificial lights and electronic displays emit blue light at much lower intensities than those associated with daylight outdoors. Nevertheless, the close proximity of the screens to the eyes, together with the long exposure times late into the evening and nighttime, lead to health risks. Blue light dosimeters for indoor use, as shown in FIGS. 16A-16B, adopt designs similar to those for outdoors, but with a collection of ten blue PDs in parallel and three 7.5 mF SCs in series, as shown in FIG. 16C, to increase the photocurrent and decrease the storage capacitance, for increased sensitivity, as shown in FIGS. 24A-24B. The off-the-shelf, blue PDs for indoor monitoring dosimeters have peak response at 390 nm and higher effective responsivity than those used for outdoor applications, as shown in FIG. 19. The resulting devices powered by a standard coin cell battery with a capacity of 40 mAh have diameters and thicknesses of 13.5 mm and 3.9 mm, respectively.

Figure 24C:
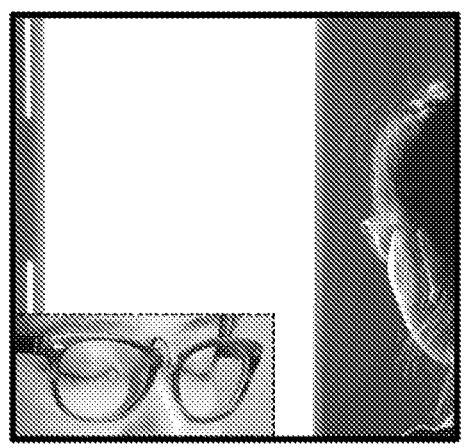
Figure 24D:
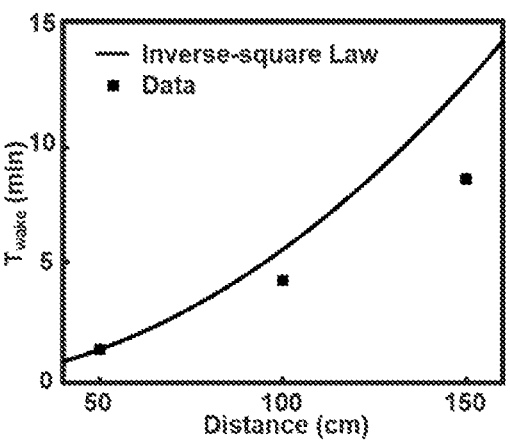
Figure 24E:
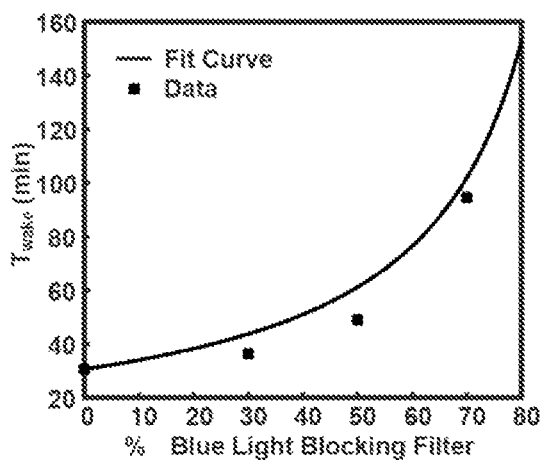
Figure 24F:
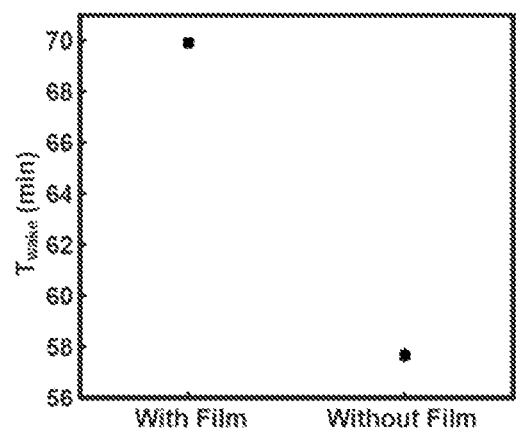

Representative results from exposure to various indoor light sources including a white light phototherapy lamp, different types of artificial light bulbs, and various electronic displays are shown in FIGS. 16D-16G. Measurements at distances (d) 50 cm, 100 cm, and 150 cm from a white light source used for treatment of SAD, as shown in FIG. 24C, indicate $T_{wake}$ values of 1.38 min, 4.24 min, and 8.47 min, respectively, as shown in FIG. 16D. Based on the inverse-square law for light propagation from a point source, the exposure intensities roughly scale inversely proportional to d². $T_{wake}$ as a function of the inverse square of d is shown in FIG. 24D. The measured exposure dose is equivalent over each $T_{wake}$, such that $T_{wake}$ is linearly related to the exposure intensity. Variation from linearity shown in FIG. 24D occurs because the light source in this case includes an array of LEDs, which cannot be accurately approximated as a point source. $T_{wake}$ of a device at 50 cm from LED, fluorescent, and incandescent light sources are 12.72 min, 22.48 min, and 43.63 min, respectively, as shown in FIG. 16E. These results are in agreement with the relative emission spectra of LED, fluorescent, and incandescent bulbs near the blue region of the spectrum. Values of $T_{wake}$ for a device at a distance of 10 cm from a television, a computer monitor, a laptop screen, a tablet computer display, and a smartphone display are 23.75 min, 26.73 min, 30.07 min, 34.19 min, and 51.78 min, respectively, as shown in FIG. 16F. All the computers displayed an identical white screen during exposure. As expected, the results show that the largest display screen, the television, emits the most amount blue light and the smallest display screen, the smartphone, radiates the least amount of blue light. A tablet display equipped with a blue-light blocking filter with settings of 0%, 30%, 50%, and 70%, as shown in FIG. 16G, yield $T_{wake}$ 30.60 min, 36.32 min, 49.00 min, and 94.62 min, respectively. A plot of $T_{wake}$ as a function of attenuation percentage is shown in FIG. 24E. The mismatch between the detection spectrum of the PD and the filtered spectrum of the tablet partly contributes to the deviation from linearity shown in FIG. 24E. Additional exposure experiment with and without a commercial anti-blue light film is shown in FIG. 24F. The $T_{wake}$ with and without anti-blue light film are 69.91±0.06 min and 57.66±0.24 min, respectively. The experiment reveals that the commercial blue-light film (ZOVER) blocks approximately 17.52% of radiation near 390 nm.

Blue Light Dosimeters Designed for Adaptive Use Both Outdoors and Indoors

Blue light dosimeters capable of use in scenarios that involve tracking of exposure both indoors and outdoors can be realized using an automated, wireless scheme for switching between parallel sensing circuits based on the presence (outdoors) or absence (indoors) of UVA irradiation, as shown in FIG. 17A. The width (w), length (l), thickness, and weight are 12.32 mm, 14.78 mm, 4.21 mm, and 1.09 g, respectively, with a 40 mAh battery. The circuit shown in FIG. 17B includes separate ADMs configured for monitoring outdoors (1 blue PD, 1 SC, 1 MOS) and indoors (10 blue PDs, 3 SCs, 1 MOS) paired with an UVA PD and a MOS. The BLE SoC is configured to automatically switch between the two ADMs for low (outdoor) and high (indoor) detection sensitivity based on the voltage input from the UVA PD ($V_{UVA}$) via a 2:1 multiplexer (MUX) based on a selection signal (S). A GPIO connected to UVA PD is set to HIGH ('1') or LOW ('0') in the presence or absence of UVA radiation, respectively. The GPIO read value serves as the selection signal. Under solar exposure, $V_{UVA}$ is HIGH, S is '1', and the 2:1 MUX output switches to the outdoor ADM which connects to an LPCOMP and an ADC for light-adaptive operation using $V_{REF}$ as described above. In this state, the MOS paired with the UVA PD continuously discharges the indoor ADM to prevent excessive charge buildup on the corresponding SC. In the absence of UVA radiation ($V_{UVA}$=LOW, S='0'), the 2:1 MUX output switches to the indoor ADM. An edge detector monitors the GPIO value and generates a wake-up signal (WuS) upon a rising (when the input goes from '0' to '1') or falling (when the input goes from '1' to '0') edge, corresponding to indoor-to-outdoor and outdoor-to-indoor switches, respectively. At every indoor/outdoor switching, a GPIO 'wake-up' event causes the CPU to discharge both ADMs, to update a 1-bit flag value (0' for indoor and '1' for outdoor) that is passed to the user interface as an indicator of activation of the indoor or outdoor ADM, and to enter 'sleep' mode again. When a LPCOMP 'wake-up' event occurs, the CPU operates in the same manner as described in previous sections, and additionally transmits the first 1-bit of a flag value to the user interfaces. User interfaces check whether the most significant bit (MSB) of the received BLE data is '0' or '1' and project the exposure dose indoor (MSB='0') and outdoor (MSB='1'), respectively.

Figure 17C:
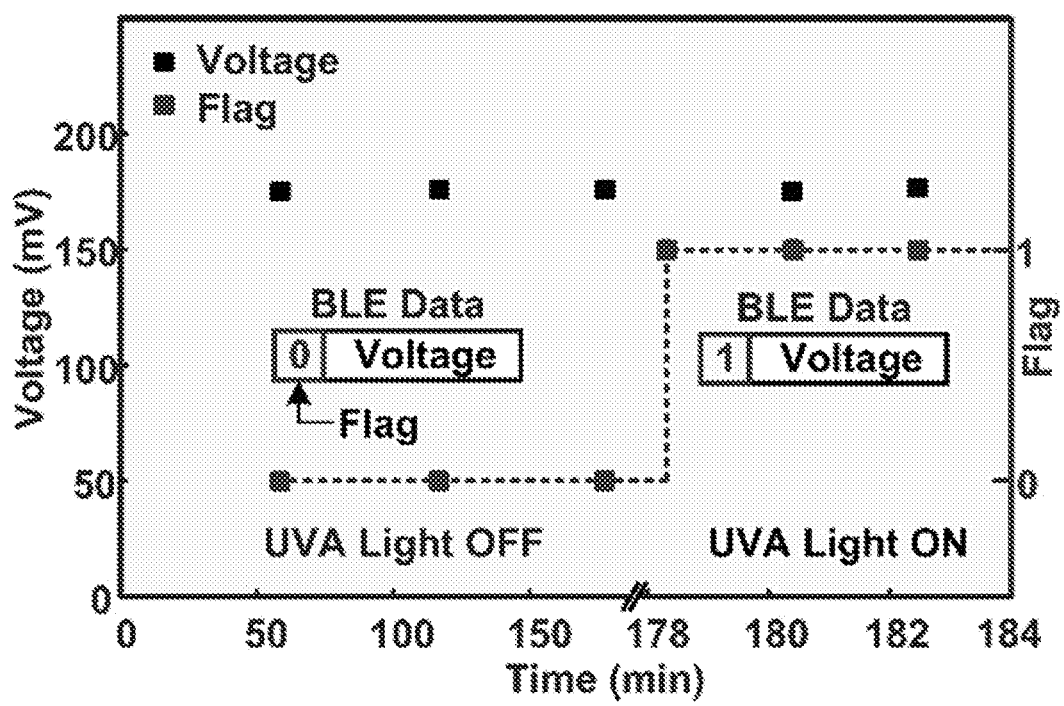
Figure 17D:
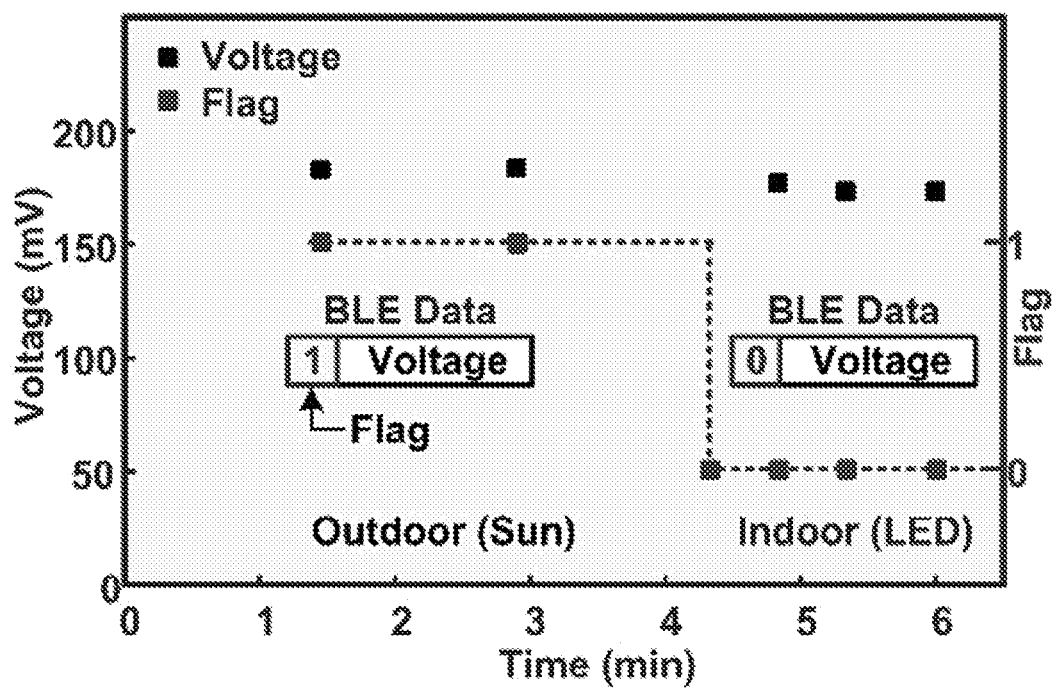

The voltage and MSB as a function of time without UVA exposure and with UVA exposure are shown in FIG. 17C. Here, dosimeters used the same blue PD for both outdoor and indoor circuits (FIG. 19) in order to illustrate the switching operation between ADMs of high or low detection sensitivity. In these experiments, a blue light lamp (Giraffe Blue Spot PT, GE Healthcare) exposes the devices to a constant intensity with and without UVA light (UVL-26, Analytik Jena). During periods without UVA, the device 'wakes-up' when the voltage output of the indoor ADM ($V_{SC0}$) exceeds 175.77±0.58 mV with a flag value of '0', and the $T_{wake}$ is 59.21±1.44 min. With the introduction of UVA, the device 'wakes-up' and updates the flag value of '1' to the user interface. During periods of UVA exposure, the device 'wakes-up' when the voltage output of the indoor ADM ($V_{SC1}$) exceeds 175.95±1.06 mV with a flag value of '1', and the $T_{wake}$ is 2.07 min. This operation is consistent with a 29 times higher sensitivity for the indoor ADM compared to the outdoor ADM. Demonstration of a blue light dosimeter with automated switching in real-life exposure conditions is shown in FIG. 17D. Here, sunlight outdoors and a 60-LED ring light indoors serve as sources of exposure, as a BLE-enabled phone wirelessly acquires $V_{SC0}$ or $V_{SC1}$ and a 1-bit flag output. Blue light/UVA intensity from the sun and from the LED lights measured with photometers are 9.8/3.6 mW/cm$^2$ and 2.5/0 mW/cm$^2$, respectively. During outdoor testing, the device 'wakes-up' when $V_{SC1}$ exceeds 183.13±0.38 mV with a flag value of '1' and a constant $T_{wake}$ of 1.45 min for an exposure dose of 853 mJ/cm$^2$. When indoors, UVA is absent and the device wakes up and updates the flag value of '0'. During indoor testing, the device wakes up when $V_{SC0}$ exceeds 174.57±2.19 mV with a flag value of '0' and shows $T_{wake}$ of 29.67±0.58 s for an exposure dose of 74 mJ/cm$^2$. The results show 11.5 times higher sensitivity for indoor ADM compared to outdoor ADM. This discrepancy is attributed to the drastic differences in the emission spectra near 390 nm between the two exposure sources.

Figures 18A, 18B:
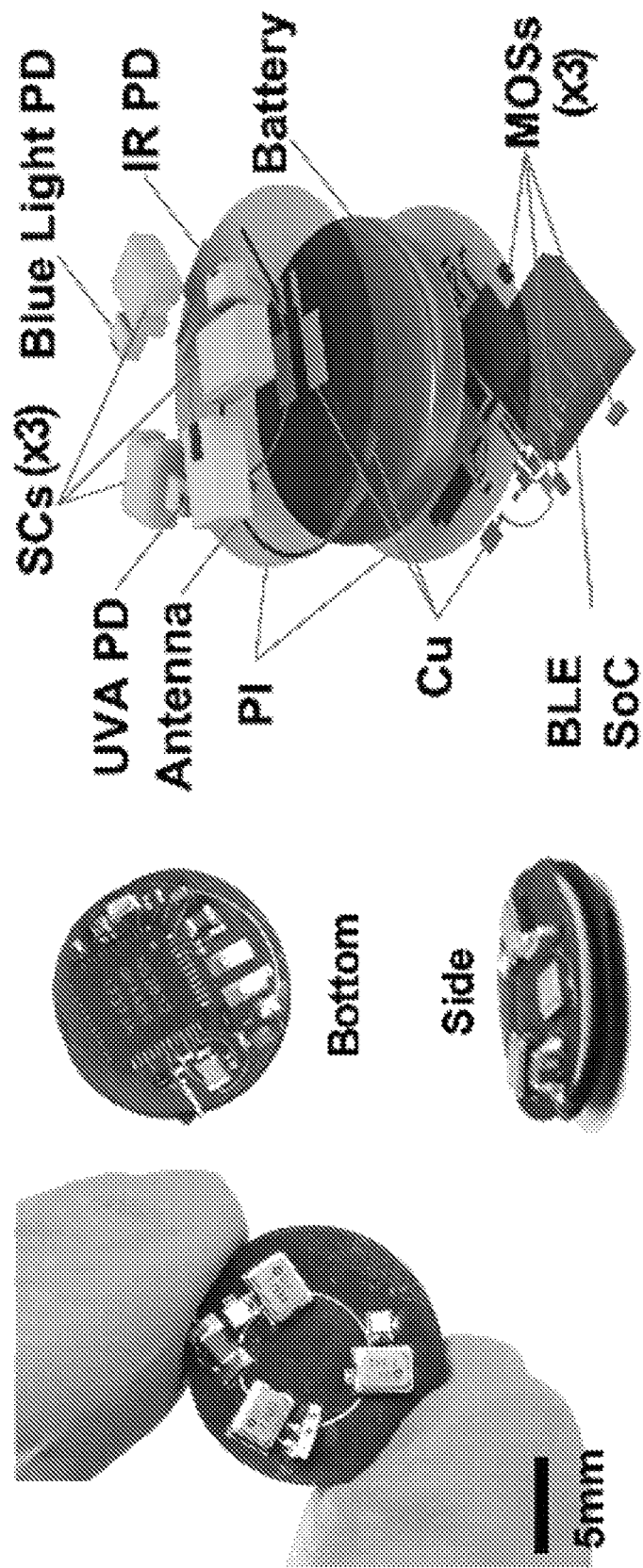
FIGS. 18A-18G show multichannel system: dosimeters with capabilities for simultaneous measurements in the UVA, blue, and IR, according to embodiments of the invention.
Figure 18C:
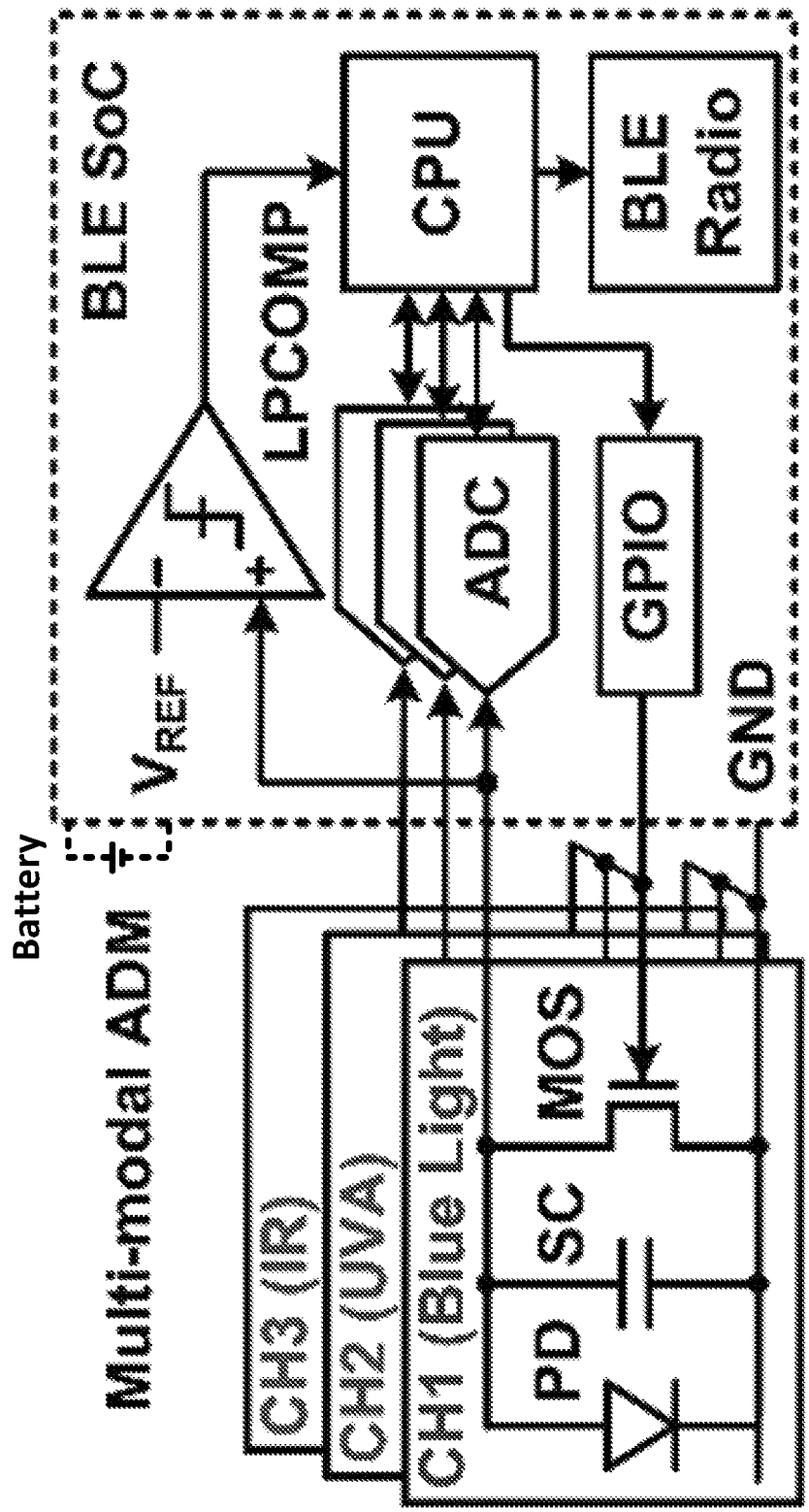
Figure 25:
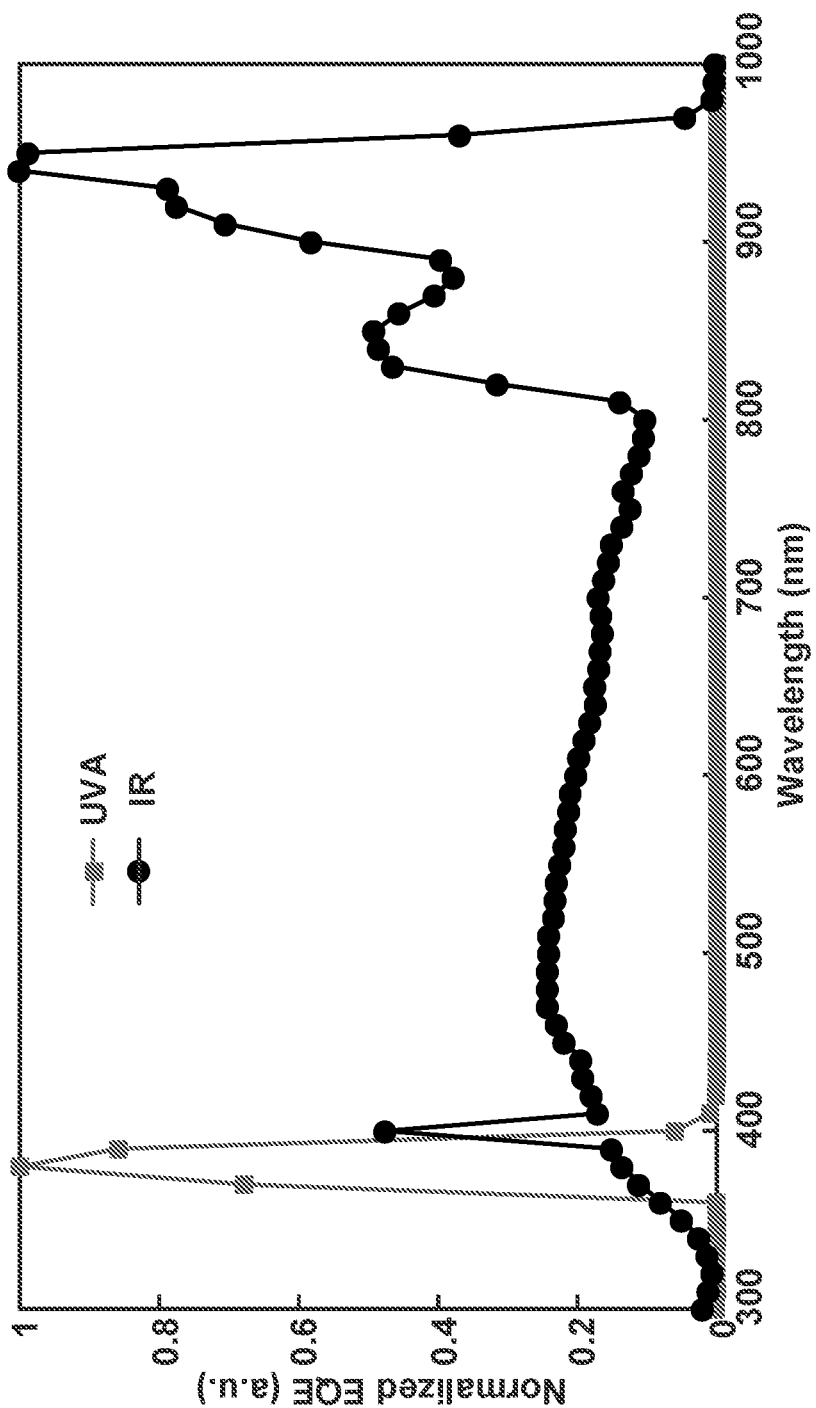
FIG. 25 shows external quantum efficiency (EQE) of UVA PD and IR PD, according to embodiments of the invention.
Figures 26A, 26B, 26C, 26D:
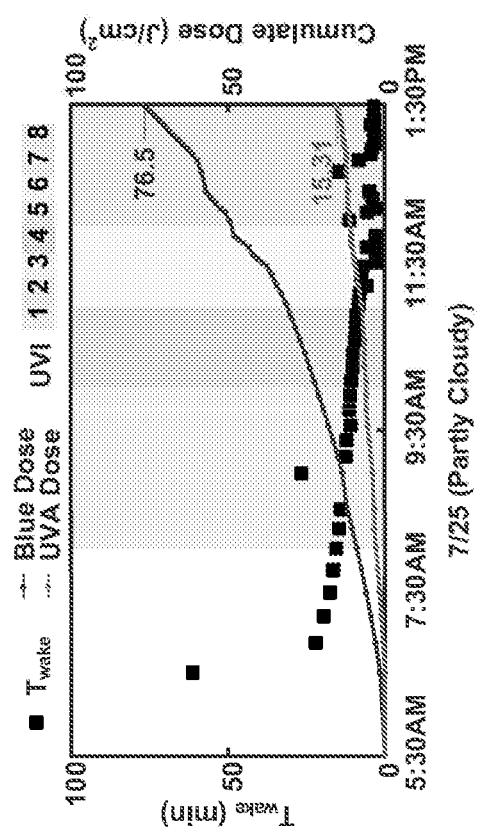
FIGS. 26A-26D show respectively daily outdoor exposure over two cloudy days (07/25-07/26; Evanston, Ill.) and two sunny days (7/31-8/1; Evanston, Ill.) from 5:30 AM to 1:30 PM using a 2-channel blue/UVA dosimeter, according to embodiments of the invention. The cumulate doses of UVA/blue light over testing periods are labeled. Hourly UV index (UVI) provided by the Environmental Protection Agency (EPA).

Multichannel Dosimeters for Wavelengths in UVA, Blue and IR Regions of Solar Spectrum The underlying designs and operating principles can be easily extended to allow simultaneous dosimetry at up to seven different wavelength bands across the solar spectrum, from the UV to VIS and infrared (IR). A 3-channel device shown in FIG. 18A measures exposure dose at UVA, blue, and IR with an estimated operating lifetime of 8.8 years for outdoors using the same exposure assumptions previously. Here, the diameter and thickness are 13.5 mm and 3.92 mm, respectively. The components include a UVA PD, a blue PD, an IR PD, three 11.5 mF SCs, three MOSFETs, a BLE SoC, and a 40 mAh battery (FIG. 18B). The peak response wavelengths of UVA and IR PDs are 380 nm and 940 nm, respectively (FIG. 25). The circuit configuration (FIG. 18C) exploits three separate ADCs on the BLE SoC, each connected to separate ADMs. Here, the LPCOMP monitors the ADC associated with the blue light sensing system (CH1), such that device enters 'run' mode and wirelessly transmits all three ADC values when $V_{SC}$ of CH1 exceeds $V_{REF}$. Blue light is chosen as a parameter to trigger a 'wake-up' event. The gates of the three MOSFETs connect to a single GPIO to allow simultaneous discharge of all three SCs following a 'wake-up' event. An example of a three-channel dosimeter mounted on earphones is shown in FIG. 18D.

Figure 18E:
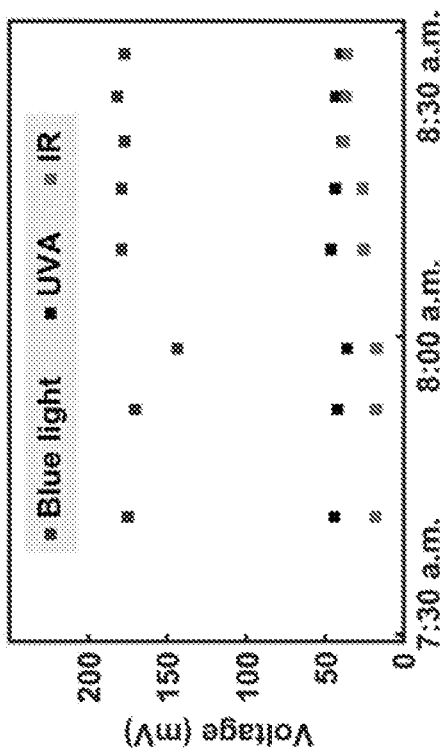
Figure 18G:
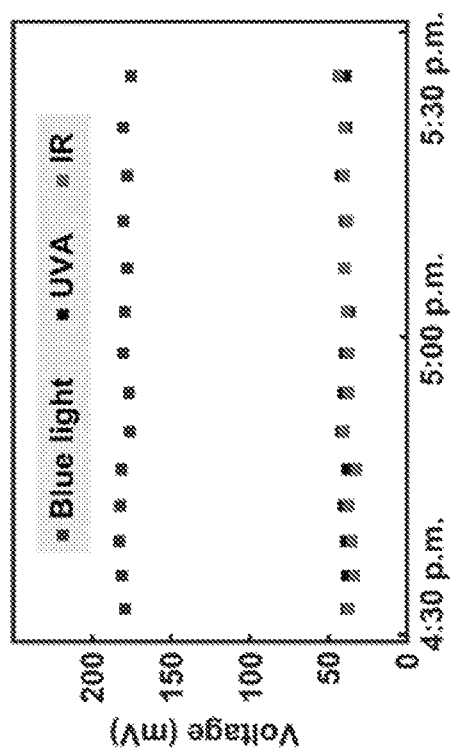
Figure 18D:
Figure 18F:
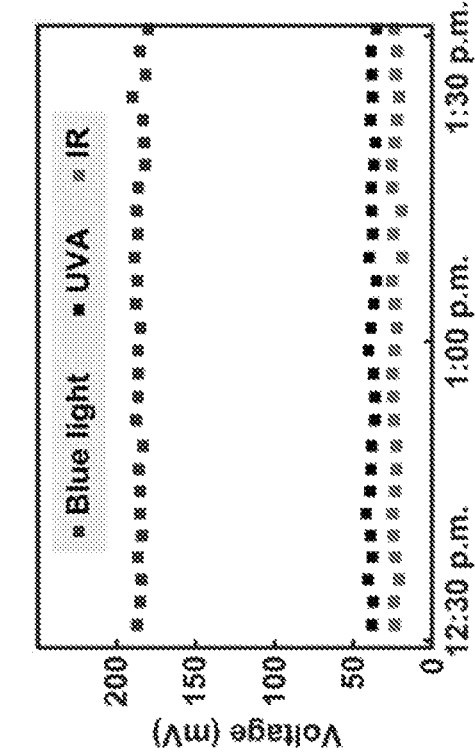

Data collected under these conditions and wirelessly transmitted to a smartphone are shown in FIGS. 18E-18G. Nine 'wake-up' events occur in the morning, and $T_{wake}$ decreases from 12.28 min to 4 min during sunrise. The measured doses of blue and UVA during the morning exposure are 13.5 J/cm$^2$ and 4.5 J/cm$^2$, respectively. Measurements around noon involve 27 'wake-up' events, and $T_{wake}$ remains approximately constant at 2.16±0.07 min. The exposure doses of blue and UVA during noon are 40.5 J/cm$^2$ and 11.8 J/cm$^2$, respectively. In the afternoon, there are 15 'wake-up' events. The $T_{wake}$ increases from 3.25 min to 5.45 min during sunset with total blue and UVA doses of 22.5 J/cm$^2$ and 7.1 J/cm$^2$, respectively. See FIGS. 26A-26D for results from a field-test using a 2-channel device to measure UVA and blue light exposure outdoors over 4 days (7/25-7/26, 7/31-8/1; Evanston, Ill.). The cumulate doses of UVA/blue light on 7/25, 7/26, 7/31, and 8/1 from 5:30 AM to 1:30 PM are 15.31/76.5 J/cm$^2$, 13.02/61.5 J/cm$^2$, 34.64/123.0 J/cm$^2$, and 33.02/115.5 J/cm$^2$, respectively.

The combined use of adaptive circuit designs and accumulation detection schemes provide the foundations for compact, wireless digital platforms capable of continuous monitoring of EMR exposure at a personalized level, across one or multiple wavelengths in an autonomous mode that adjusts continuously to surrounding conditions. These highly accurate, millimeter-scale systems function in an always-on state, with multi-year lifetimes that can be considered, in a practical sense, to be everlasting for most envisioned applications. Automatic reporting of exposure data via far-field wireless links to standard consumer electronic devices serves as the basis for information that can be used to guide healthy behaviors. These technical capabilities, taken together with a negligible user burden associated with data acquisition, power management, battery replenishment and wearability, represent an ideal collection of features. Alignment with low-cost, volume manufacturing suggest a potential for scaled deployment to help prevent risks of skin cancer, mood disorders, ocular damage and other conditions associated with EMR exposure.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LISTING OF REFERENCES

[1]. A. C. Green, S. C. Wallingford, P. McBride, Childhood exposure to ultraviolet radiation and harmful skin effects: epidemiological evidence. *Progress in Biophysics and Molecular Biology* 107, 349-355 (2011).

[2]. B. K. Armstrong, A. Kricker, The epidemiology of UV induced skin cancer. *J. Photochemistry and Photobiology B: Biology* 63, 8-18 (2001).

[3]. J. D'Orazio, S. Jarrett, A. Amaro-Ortiz, T. Scott, UV radiation and the skin. *Int. J. Molecular Sci.* 14, 12222-12248 (2013).

[4]. G. P. Guy Jr, S. R. Machlin, D. U. Ekwueme, K. R. Yabroff, Prevalence and costs of skin cancer treatment in the US, 2002-2006 and 2007-2011. *American J. Preventive Med.* 48, 183-187 (2015).

[5]. F. Liebel, S. Kaur, E. Ruvolo, N. Kollias, M. D. Southall, Irradiation of skin with visible light induces reactive oxygen species and matrix-degrading enzymes. *J. Investigative Dermatology* 132, 1901-1907 (2012).

[6]. Y. Nakashima, S. Ohta, A. M. Wolf, Blue light-induced oxidative stress in live skin. *Free Radical Biology and Med.* 108, 300-310 (2017).

[7]. C. Regazzetti, L. Sormani, D. Debayle, F. Bernerd, M. K. Tulic, G. M. De Donatis, B. Chignon-Sicard, S. Rocchi, T. Passeron, Melanocytes sense blue light and regulate pigmentation through opsin-3. *J. Investigative Dermatology* 138, 171-178 (2018).

[8]. W. Noell, W. Walker, B. Kang, S. Berman, Retinal damage by visible light. *Invest Ophthalmol* 5, 450-473 (1966).

[9]. W. K. Noell, Possible mechanisms of photoreceptor damage by light in mammalian eyes. *Vision Res.* 20, 1163-1171 (1980).

[10]. F. Behar-Cohen, C. Martinsons, F. Viénot, G. Zissis, A. Barlier-Salsi, J. P. Cesarini, O. Enouf, M. Garcia, S. Picaud, D. Attia, Light-emitting diodes (LED) for domestic lighting: Any risks for the eye? *Progress in Retinal and Eye Res.* 30, 239-257 (2011).

[11]. A. King, E. Gottlieb, D. G. Brooks, M. P. Murphy, J. L. Dunaief, Mitochondria-derived reactive oxygen species mediate blue light-induced death of retinal pigment epithelial cells. *Photochemistry and Photobiology* 79, 470-475 (2004).

[12]. B. F. Godley, F. A. Shamsi, F. Q. Liang, S. G. Jarrett, S. Davies, M. Boulton, Blue light induces mitochondrial DNA damage and free radical production in epithelial cells. *J. Biological Chemistry* 280, 21061-21066 (2005).

[13]. C. I. Eastman, Natural summer and winter sunlight exposure patterns in seasonal affective disorder. *Physiology & Behavior* 48, 611-616 (1990).

[14]. Y. Shi, M. Manco, D. Moyal, G. Huppert, M. Araki, A. Banks, H. Joshi, R. McKenzie, A. Seewald, G. Griffin, E. Sen-Gupta, D. Wright, P. Bastien, F. Valceschini, S. Seité, J. A. Wright, R. Ghaffari, J. Rogers, G. Balooch, R. M. Pielak, Soft, stretchable, epidermal sensor with integrated electronics and photochemistry for measuring personal UV exposures. *PloS one* 13, e0190233 (2018).

[15]. J. Heydenreich, H. C. Wulf, Miniature personal electronic UVR dosimeter with erythema response and time-stamped readings in a wristwatch. *Photochemistry and Photobiology* 81, 1138-1144 (2005).

[16]. S. Y. Heo, J. Kim, P. Gutruf, A. Banks, P. Wei, R. Pielak, G. Balooch, Y. Shi, H. Araki, D. Rollo, C. Gaede, M. Patel, J. W. Kwak, A. E. Peña-Alcántara, K.-T. Lee, Y. Yun, J. K. Robinson, S. Xu, J. A. Rogers, Wireless, battery-free, flexible, miniaturized dosimeters monitor exposure to solar radiation and to light for phototherapy. *Sci. Transl. Med.* 10, eaau1643 (2018).

[17]. A. Magnusson, D. Boivin, Seasonal affective disorder: an overview. *Chronobiology Int.* 20, 189-207 (2003).

[18]. G. Glickman, B. Byrne, C. Pineda, W. W. Hauck, G. C. Brainard, Light therapy for seasonal affective disorder with blue narrow-band light-emitting diodes (LEDs). *Biological Psychiatry* 59, 502-507 (2006).

[19]. D. F. Kripke, Light treatment for nonseasonal depression: speed, efficacy, and combined treatment. *J. Affective Disorders* 49, 109-117 (1998).

[20]. C. E. Remé, A. Wirz-Justice, M. Terman, The visual input stage of the mammalian circadian pacemaking system: I. Is there a clock in the mammalian eye? *J. Biological Rhythms* 6, 5-29 (1991).

[21]. A. Wirz-Justice, P. Graw, K. Kräuchi, A. Sarrafzadeh, J. English, J. Arendt, L. Sand, 'Natural' light treatment of seasonal affective disorder. *J. Affective Disorders* 37, 109-120 (1996).

[22]. S. Banerjee, E. G. Hoch, P. D. Kaplan, E. L. P. Dumont, A comparative study of wearable ultraviolet radiometers, 2017 *IEEE Life Sciences Conference (LSC)*, Sydney, NSW, Australia, Dec. 3-15, 2017.

[23]. W. Zou, A. Gonzalez, D. Jampaiah, R. Ramanathan, M. Taha, S. Walia, S. Sriram, M. Bhaskaran, J. M. Dominguez-Vera, V. Bansal, Skin color-specific and spectrally-selective nakedeye dosimetry of UVA, B and C radiations, *Nature Communications,* 9:3743 (2018).

[24]. J. A. Rogers, A. R. Banks, X. Wang, G. Brown, Alternative approach to UV sensing, PCT Publication No. WO2016196673, (2016).

What is claimed is:

1. An electronic system for monitoring a physical parameter, comprising:
   an accumulation detection module (ADM) for continuously measuring the physical parameter in terms of exposure dose in an accumulation mode, wherein the ADM is a light-powered sensing system comprising at least one photodiode (PD) for continuously generating photocurrent with a magnitude that is proportional to an intensity of electromagnetic radiation in response to exposure to the electromagnetic radiation (EMR), at least one capacitor connected to the at least one PD in parallel for storing charges accumulated from the generated photocurrent of the at least one PD, and at least one transistor having a source and a drain respectively connected to two terminals of the at least one capacitor;
   a power source for operably providing power; and
   a system on a chip (SoC) coupling with the ADM and the power source and operably in a sleep mode, or in a run mode, wherein the SoC comprises a wireless communication module, at least one signal converter and a comparator coupled to the source of the at least one transistor, and a controller coupled to the at least one signal converter, the comparator and the wireless communication module, and is configured such that in operation, the comparator monitors a voltage across the at least one capacitor when the SoC operates in the sleep mode, and when the voltage is equal to or greater than a pre-defined threshold, generates a wake-up event that triggers the SoC to operate in the run mode in which the controller wirelessly transmits a signal of the voltage converted by the at least one signal converter to a receiver through the wireless communication module, activates the at least one transistor to discharge the at least one capacitor and then returns the SoC to the sleep mode.

2. The electronic system of claim 1, wherein the SoC further comprises at least one general-purpose input/output (GPIO) coupled between a gate of the at least one transistor and the controller for operably activating the at least one transistor to discharge the at least one capacitor.

3. The electronic system of claim 1, wherein the at least one PD comprises a plurality of PDs, and each PD of the plurality of PDs is responsive to a respective wavelength region of the electromagnetic radiation, wherein the ADM is characterized with a plurality of channels, and each channel has a respective PD of the plurality of PDs, the at least one capacitor coupled to said respective PD and the at least one transistor coupled to said at least one capacitor, for measuring the exposure dose of said respective wavelength region of the electromagnetic radiation.

4. The electronic system of claim 3, wherein the plurality of PDs comprises an UVA PD, a blue PD, and an infrared (IR) PD.

5. The electronic system of claim 3, wherein the at least one signal converter comprises a plurality of analog-to-digital converters (ADCs), and each ADC is electrically couple to said each channel of the plurality of channels, and wherein the comparator is configured to monitor the voltage in said each channel of the plurality of channels, such that when the voltage is equal to or greater than the pre-defined threshold, the SoC enters the run mode and wirelessly transmits signals output from the plurality of ADCs and simultaneously discharges said at least one capacitor of the plurality of channels.

6. The electronic system of claim 1, wherein the at least one PD comprises a plurality of PDs, the at least one capacitor comprises a plurality of capacitors and the at least one transistor comprise a first transistor and a second transistor, wherein the ADM is characterized with an outdoor ADM and an indoor ADM for monitoring the exposure to EMR outdoors and indoors, respectively, wherein the outdoor ADM has one of the plurality of PDs, one of the plurality of capacitors coupled to said at least one PD and the first transistor coupled to said at least one capacitor, and wherein the indoor ADM has remaining PDs of the plurality of PDs arranged in parallel, remaining capacitors from the plurality of capacitors arranged in parallel and coupled to the remaining PDs and the second transistor coupled to the remaining capacitors.

7. The electronic system of claim 6, wherein the indoor ADM and the outdoor ADM are paired with a UVA PD and a third transistor and operably switchable based on presence or absence of UVA radiation, wherein the presence or the absence of the UVA radiation results in a high value or a low value of a voltage, Vuva, output from the UVA PD, respectively.

8. The electronic system of claim 7, wherein the SoC is configured to automatically switch between the indoor ADM and the outdoor ADM through a two-to-one multiplexer, wherein the two-to-one multiplexer is configured to switch the ADM to the outdoor ADM when the voltage VUVA is in the high value, and to the indoor ADM when the voltage VUVA is in the low value.

9. The electronic system of claim 8, wherein a source and a drain of the third transistor are coupled to a source and a drain of the second transistor, respectively, and the UVA PD is coupled between a gate and the drain of the third transistor, such that in the outdoor ADM, the third transistor continuously discharges the indoor ADM to prevent excessive charge buildup on the plurality of capacitors.

10. The electronic system of claim 9, wherein the SoC further comprises an edge detector coupled between the controller and the UVA PD for monitoring the high value or the low value of the voltage Vuva and generating a wake-up signal upon a rising edge when the high value or the low value goes from the low value to the high value, or a falling edge when the high value or the low value goes from the high value to the low value, corresponding to indoor-to-outdoor or outdoor-to-indoor switches, respectively, and wherein at each and every indoor-to-outdoor or outdoor-to-indoor switch, the wake-up signal causes the controller to discharge both the indoor ADM and the outdoor ADM, to update a 1-bit flag value with '0' for indoor and '1' for outdoor that is passed to an user interface as an indicator of activation of the indoor ADM or the outdoor ADM, and then to enter the sleep mode.

11. The electronic system of claim 1, being a first dosimeter for monitoring exposure dose indoors, a second dosimeter for adaptively monitoring exposure dose outdoors and the exposure dose indoors, or a multichannel dosimeter for simultaneously monitoring exposure dose in different wavelength regions of the electromagnetic radiation.

12. The electronic system of claim 1, wherein the ADM operably measures the exposure dose in a continuous fashion, without power consumption from the power source.

13. The electronic system of claim 1, wherein the controller is a central processing unit (CPU) or a microcontroller.

14. The electronic system of claim 1, wherein the wireless communication module comprises at least one of a Bluetooth® low energy (BLE) module, cellular communication module, and a near-field communication (NFC) module.

15. The electronic system of claim 14, wherein the wireless communication module automatically and periodically transmits a measured dose of the physical parameter to the receiver without an active user intervention.

16. The electronic system of claim 1, wherein the sleep mode is characterized with a deep sleep mode and a shallow sleep mode, wherein when the voltage or a stored electrical energy is less than the pre-defined threshold, the SoC operates in the deep sleep mode in which only a low-power comparator is energized a deep sleep sampling interval, and when the voltage or the stored electrical energy is sampled with a shallow sleep sampling interval and compared to the pre-defined threshold, and the wake-up event is generated when the voltage or the stored electrical energy is equal to or greater than the pre-defined threshold, the SoC operates in the shallow sleep mode in which the low-power comparator, an ADC sampler and a processor timer are energized.

17. The electronic system of claim 16, wherein the deep sleep mode has an average deep sleep current in the electronic system that is less than or equal to 10 μA.

18. The electronic system of claim 16, wherein the deep sleep sampling interval is greater than the shallow sleep sampling interval, wherein the shallow sleep sampling interval is less than or equal 5 minutes.

19. The electronic system of claim 16, wherein the deep sleep sampling interval and the shallow sleep sampling interval are dynamically controllable and changeable depending on operating parameters including a geographic location of the electronic system, time of day, magnitude of the physical parameter being measured and/or a user characteristic.

20. The electronic system of claim 19, wherein the user characteristic is one or more of skin type, sun protection parameter, age of user, ingestion of a sensitizing agent, and user sensitivity.

21. The electronic system of claim 20, wherein the geographic location is a field of agriculture, a museum, a beach, an outdoor venue, a sporting competition, adjacent to an industrial plant, energy plant, an agricultural grow region, UV water purification, UV sterilization, a sauna, a spa, a workout facility, a gymnasium, a gameroom, a hospital, or a rehabilitation facility.

22. The electronic system of claim 16, wherein the pre-defined threshold that triggers the SoC to operate from the sleep mode to the run mode is hard programmed on the SoC, or remotely set through the receiver.

23. The electronic system of claim 22, wherein the receiver is configured to receive an input of the user characteristic to dynamically vary the pre-defined threshold that controls a switch between the deep sleep mode and the shallow sleep mode.

24. The electronic system of claim 1, wherein the receiver is one or more of a mobile device including a smart phone and a laptop or tablet, and a fixed receiver including a Bluetooth® low energy (BLE) system or beacon, cellular data transmission stations, a computer and a data center.

25. The electronic system of claim 1, wherein the SoC further comprises a memory for storing the physical parameter to avoid unexpected data loss due to disruption of the wireless communication module to the receiver.

26. The electronic system of claim 1, further comprising a user-controllable switch to switch the electronic system to a power-off state, wherein the user-controllable switch is a mechanical switch or a wirelessly-controllable switch.

27. The electronic system of claim 1, further comprising an on board actuator to alert a user to a risk condition, wherein the actuator is one or more of a mechanical vibrator, an electric stimulator, and an optical light source.

28. The electronic system of claim 27, wherein the alert is communicated to the receiver.

29. The electronic system of claim 1, having an instantaneous mode for short term monitoring of the physical parameter.

30. The electronic system of claim 1, having a form factor that allows for a surface area profile of less than 3 cm.

31. The electronic system of claim 30, having an effective diameter less than 2.5 cm and a thickness less than 1 cm.

32. The electronic system of claim 1, being partially or completely encapsulated by one or more encapsulation layers for thermal isolation, pressure isolation, pollutant isolation, electrical isolation and/or high external radiation isolation.

33. The electronic system of claim 1, further comprising means for awaking the electronic system from a deep sleep mode.

34. The electronic system of claim 33, wherein the awaking means comprises at least one light emitting diode (LED) or capacitor.

35. The electronic system of claim 1, being configured to operate for 2 months or more without replacing or recharging the power source, preferably, 1 year or more without replacing or recharging the power source.

36. The electronic system of claim 1, being configured to operate with a power consumption that is at least 25% lower than that of a comparable system that incorporates a sensor that does not offer the accumulation mode in the operation; and/or with an accuracy that is at least 25% better than that of the comparable system that incorporates the sensor that does not offer the accumulation mode in the operation.

37. The electronic system of claim 1, being configured to be wearable by a person and/or affixed to a skin surface.

38. The electronic system of claim 37, being incorporated into a piece of jewelry, an accessory, a watch, a piece of clothing, and/or to be worn underneath the piece of clothing.

39. The electronic system of claim 1, wherein the physical parameter is one or more of exposure to UV radiation, physical motion, temperature, heat index, thermoregulation, skin hydration, sweat loss, electrolyte level, humidity, air pollution, chemical exposure, acoustic level, magnetic exposure, radiation exposure, visible light, heat, heat flux, metabolic expenditure, vibratory motion, mechanical shock, and rates of change thereof.

40. An electronic system for monitoring a physical parameter, comprising:
an accumulation detection module (ADM) comprising at least one accumulation mode sensor for measuring the physical parameter by generating electrical energy associated with the physical parameter in response to a surrounding condition, at least one energy storing device connected to the at least one accumulation mode sensor in parallel for accumulatively storing the electrical energy, and at least one transistor having a source and a drain respectively connected to two terminals of the at least one energy storing device for operably discharging the at least one energy storing device;
a power source for operably providing power; and
a system on a chip (SoC) coupling with the ADM and the power source, configured such that the electrical energy stored in the at least one energy storing device is monitored, and when the stored electrical energy is equal to or greater than a pre-defined threshold, a wake-up event is generated to trigger the SoC to operates in a run mode in which the physical parameter associated with the stored electrical energy is wirelessly transmitted to a receiver and the stored electrical energy in the energy storing device is discharged, and then the SoC returns to a sleep mode in which a minimal power is consumed.

41. The electronic system of claim 40, wherein the SoC comprises a wireless communication module, a low-power comparator coupled to the at least one transistor, and a controller coupled to the low-power comparator and the wireless communication module, such that in operation, the low-power comparator monitors the stored electrical energy, and when the stored electrical energy is equal to or greater than pre-defined threshold, generates the wake-up event that triggers the SoC to operate in the run mode in which the controller wirelessly transmits a signal associated with the stored electrical energy to the receiver through the wireless communication module, activates the at least one transistor to discharge the at least one energy storing device and then returns the SoC to the sleep mode.

42. The electronic system of claim 40, wherein the at least one accumulation mode sensor comprises one or more of optical sensors, piezoelectric crystals, triboelectric sensors, acoustic sensors, mechanical sensors, pressure sensors, thermoelectric sensors, temperature sensors, temperature gradient sensors, humidity sensors, air pollution sensors, sweat or fluid sensors, electrocardiogram (ECG), Electromyography (EMG), pulse oximetry, accelerometers, and electromagnetic energy sensors for selected wavelengths including from radio wavelengths to gamma ray wavelengths.

43. The electronic system of claim 40, wherein the at least one energy storing device comprises one or more of capacitors, accumulators, and rechargeable and dischargeable batteries.

44. The electronic system of claim 40, wherein the surrounding condition includes one or more of electromagnetic radiation from the Sun and/or artificial sources, air quality, weather, sounds, movements, and environmental changes.

45. An electronic system for monitoring of one or more physical parameters comprising:
at least one accumulation detection module (ADM) for sensing the one or more physical parameters that are accumulatively stored in a form of electrical energy based on a magnitude of the one or more physical parameters, wherein the at least one ADM comprises:
at least one photodiode (PD) for continuously generating photocurrent;
at least one capacitor connected to the at least one PD in parallel for storing the electrical energy accumulated from the generated photocurrent of the at least one PD; and
at least one transistor having a source and a drain respectively connected to two terminals of the at least one capacitor;
a wireless communication module electronically coupled to the at least one ADM;
a controller electronically couple to the at least one ADM module and the wireless communication module; and
a power source electronically coupled to the wireless communication module, the controller and/or the at least one ADM to power the wireless communication module, the controller, and/or the at least one ADM,
configured such that the stored electrical energy is monitored, and when the stored electrical energy is equal to or greater than a pre-defined threshold, a wake-up event is generated to trigger the electronic system to transmit the one or more physical parameters wirelessly to a receiver and discharge the stored electrical energy, and then return to a sleep mode in which a minimal power is consumed.

46. A system for monitoring one or more physical parameters, comprising a plurality of electronic systems deployed in a plurality of spatial-apart locations of interest, wherein each electronic system is claim 1.

47. The system of claim 46, wherein the plurality of electronic systems is worn on or connected to skin of a user at a plurality of distinct skin locations.

48. The system of claim 46, wherein the plurality of spatial-apart locations of interest is in a field of agriculture, a museum, a beach, an outdoor venue, a sporting competition, adjacent to an industrial plant, energy plant, an agricultural grow region, UV water purification, UV sterilization, a sauna, a spa, a workout facility, a gymnasium, a gameroom, a hospital, or a rehabilitation facility.

49. A method of monitoring the physical parameter with the electronic system of claim 40, comprising:
continuously measuring the physical parameter with the at least one accumulation mode sensor by generating the electrical energy associated with the physical parameter in response to the surrounding condition, and accumulatively storing the electrical energy in the at least one energy storing device that is coupled to the at least one accumulation mode sensor;
periodically comparing the stored electrical energy to the pre-defined threshold; and
entering the electronic system in the sleep mode when the stored electrical energy is less than the pre-defined threshold;
otherwise generating the wake-up event to trigger the electronic system to wirelessly transmit the physical parameter associated with the stored electrical energy to the receiver and to discharge the stored electrical energy in the at least one energy storing device, and then to return to the sleep mode.

50. The method of claim 49, wherein when the stored electrical energy is equal to or greater than the pre-defined threshold, the electronic system is in a shallow-sleep mode in which all electronic components in the electronic system, except for an analog-to-digital convertor (ADC) and a timer, wait in a halt status, the method further comprising:
evaluating from the ADC a ready interrupt condition, thereby waking a controller to read a value, Vsc, of the ADC and compare the Vsc to the pre-defined threshold (Vref) and for Vsc>Vrer send the physical parameter to the receiver, reset the at least accumulation mode sensor by discharging the at least one energy storing device, trigger the shallow sleep mode and provide a shallow sleep sampling interval; for Vsc<Vrer enter in the deep sleep mode in which only a low power comparator is energized with a deep sleep sampling interval that is greater than the shallow sleep sampling interval.

51. The method of claim 49, further comprising: providing an instantaneous monitoring mode in which sensor output is continuously and instantaneously communicated to the receiver for short-term monitoring.

52. The method of claim 51, wherein the short-term monitoring is manually triggered by a user or is automatically triggered by the measured physical parameter that is greater than or equal to a user-selected reference level physical parameter.

53. The method of claim 49, wherein the electronic system is a first dosimeter for monitoring exposure dose indoors, a second dosimeter for adaptively monitoring exposure dose outdoors and the exposure dose indoors, or a multichannel dosimeter for simultaneously monitoring exposure dose in different wavelength regions of electromagnetic radiation.

54. The method of claim 49, wherein the electronic system is attached on a skin surface or incorporated into an article of clothing or an accessory worn on a body.

55. The method of claim 49, further comprising alerting a user wearing the electronic system as to exceeding a safe physical parameter exposure.

56. The method of claim 55, wherein the user wears a plurality of electronic systems over specific distinct skin locations.

57. The method of claim 56, wherein the alert comprises time to burn on different skin locations.

58. The method of claim 49, further comprising providing a user-characteristic to the receiver, wherein the user-characteristic is used to automatically determine the pre-defined threshold Vrer tailored to a user.

59. A non-transitory tangible computer-readable medium storing instructions which, when executed by one or more processors, cause the method of claim 49 to be performed.

60. An electronic system for monitoring a physical parameter, comprising:
an accumulation detection module (ADM) having:
at least one photodiode (PD) for continuously generating photocurrent;

at least one capacitor connected to the at least one PD in parallel for storing charges accumulated from the generated photocurrent of the at least one PD; and at least one transistor having a source and a drain respectively connected to two terminals of the at least one capacitor; and a system on a chip (SoC) coupling with the ADM and operably in a sleep mode or in a run mode, having:

at least one signal converter;

a comparator coupled to the source of the at least one transistor; and a controller coupled to the at least one signal converter and the comparator, wherein in operation, the comparator monitors a voltage across the at least one capacitor when the SoC operates in the sleep mode; and when the voltage is equal to or greater than a pre-defined threshold, the comparator generates a wake-up event that triggers the SoC to operate in the run mode in which the controller wirelessly transmits a signal of the voltage converted by the at least one signal converter to a receiver, thereby activating the at least one transistor to discharge the at least one capacitor and then returning the SoC to the sleep mode.

61. An electronic system for monitoring a physical parameter, comprising:

an accumulation detection module (ADM) having:

at least one accumulation mode sensor for measuring the physical parameter by generating electrical energy associated with the physical parameter in response to a surrounding condition;

at least one energy storing device connected to the at least one accumulation mode sensor in parallel for accumulatively storing the electrical energy; and a switching device connected to the at least one energy storing device for operably discharging the at least one energy storing device; and a system on a chip (SoC) coupling with the ADM, configured such that the electrical energy stored in the at least one energy storing device is monitored, and when the stored electrical energy is equal to or greater than a pre-defined threshold, a wake-up event is generated to trigger the SoC to operates in a run mode in which the physical parameter associated with the stored electrical energy is wirelessly transmitted to a receiver and the switching device is activated to discharge the stored electrical energy in the at least one energy storing device, and then the SoC returns to a sleep mode in which a minimal power is consumed.

* * * * *